United States Patent [19]
Cragoe, Jr. et al.

[11] 4,066,692
[45] Jan. 3, 1978

[54] 11,12-SECOPROSTAGLANDINS

[75] Inventors: Edward J. Cragoe, Jr.; John B. Bicking; Robert L. Smith, all of Lansdale, Pa.

[73] Assignee: Merck & Co., Inc., Rahway, N.J.

[21] Appl. No.: 669,118

[22] Filed: Mar. 22, 1976

Related U.S. Application Data

[63] Continuation-in-part of Ser. No. 571,038, April 23, 1975, abandoned, which is a continuation-in-part of Ser. No. 389,901, Aug. 23, 1973, abandoned, which is a continuation-in-part of Ser. No. 302,365, Oct. 30, 1972, abandoned.

[51] Int. Cl.² .............................................. C07C 59/00
[52] U.S. Cl. .................................. 424/312; 260/560; 260/266; 260/261; 260/190; 260/405; 260/405.5; 260/408; 260/410.912; 260/412; 260/535 R; 260/501.15; 260/501.17; 260/521 B; 260/535 H; 260/638 B; 260/561 B; 260/593 H; 260/611 A; 424/318
[58] Field of Search ................. 260/535 R, 535 H, 484

[56] References Cited
PUBLICATIONS

Derwent Abst. 44724 w/27, DT2458-911, Merck & Co., Inc.

*Primary Examiner*—Paul J. Killos
*Attorney, Agent, or Firm*—Thomas E. Arther; Harry E. Westlake, Jr.; Rudolph J. Anderson, Jr.

[57] ABSTRACT

This invention relates to 11,12-secoprostaglandins and processes for their manufacture. These compounds have prostaglandin-like biological activity and are particularly useful as renal vasodilators, for the treatment of hypertension, for the prevention of thrombus formation, in preventing gastric secretion, and as regulators of the immune response.

43 Claims, No Drawings

11,12-SECOPROSTAGLANDINS

RELATIONSHIP TO OTHER APPLICATIONS

This application is a continuation-in-part application of copending U.S. Ser. No. 571,038 filed Apr. 23, 1975, abandoned; which in turn is a continuation-in-part of U.S. Ser. No. 389,901 filed Aug. 23, 1973 and now abandoned; which in turn is a continuation-in-part of U.S. Ser. No. 302,365 filed Oct. 30, 1972 and now abandoned.

SUMMARY OF THE INVENTION

This invention relates to novel 11,12-secoprostaglandins which can be represented by the following formula:

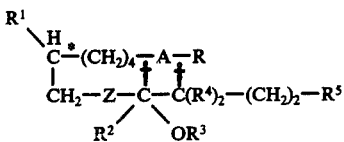

wherein R is selected from the group consisting of carboxy and a carboxy salt which incorporates a pharmaceutically acceptable cation, such as metal cations derived from alkali metals, alkaline earth metals, and amines such as ammonia, primary and secondary amines, and quaternary ammomium hydroxides. Especially preferred metal cations are those derived from alkali metals, e.g., sodium, potassium, lithium, and the like, and alkaline earth metals, e.g., calcium, magnesium, and the like and other metals, ie., aluminum, iron and zinc.

Pharmaceutically acceptable cations can be formed from primary, secondary, or tertiary amines, or quaternary ammonium hydroxides such as mthylamine, dimethylamine, trimethylamine, ethylamine, N-methylhexylamine, benzylamine, α-phenethylamine, ethylenediamine, piperidine, morpholine, pyrrolidine, 1,4-dimethylpiperazine, ethanolamine, diethanolamine, triethanolamine, tris(hydroxymethyl)aminomethane, N-methylglucamine, N-methylglucosamine, ephedrine, procaine, tetramethylammonium hydroxide, tetraethylammonium hydroxide, benzyltrimethylammonium and the like.

R is also selected from alkoxycarbonyl (—COOY) wherein Y is alkyl having 1-10 carbon atoms, 1-succinimidoethyl, 1-(pivaloyloxy)ethyl, 2-acetamidoethyl or diloweralkylaminoloweralkyl; carbamoyl (—CONH$_2$); substituted carbamoyl (—CONR$^6$R$^7$) wherein R$^6$ and R$^7$ are selected from the group consisting of hydrogen, lower alkyl having 1-4 carbon atoms and diloweralkylaminoalkyl having 4-7 carbon atoms; and carbazoyl (—CONHNH$_2$).

A is selected from the group consisting of ethylene (—CH$_2$CH$_2$), trimethylene (—CH$_2$CH$_2$CH$_2$—), α-methylethylene (—CH$_2$CH(CH$_3$)—), β-methylethylene (—CH$_2$CH(CH$_3$)CH$_2$), α,α-dimethylethylene (—CH$_2$C(CH$_3$)$_2$—), β,β-dimethylethylene (—C(CH$_3$)$_2$CH$_2$—) and oxymethylene (—O—CH$_2$—). (Note that when A consists of a two carbon bridge, the term "α" refers to the carbon adjacent to R, while "β" refers to the other carbon atom.)

R$^1$ is selected from the group consisting of formyl, acetyl, propionyl, acryloyl, hydroxyacetyl, 3-hydroxypropionyl, hydroxymethyl, 1-hydroxyethyl, 1,2-dihydroxyethyl, 1,3-dihydroxypropyl, and 1-hydroxy-1-methylethyl.

Z is selected from the group consisting of methylene, ethylene, trimethylene tetramethylene, vinylene (—CH=CH—), and ethynylene (—C≡C—).

R$^2$ is independently selected from the group consisting of hydrogen and methyl.

R$^3$ is selected from the group consisting of hydrogen, and lower alkanoyl of 1-5 carbon atoms, e.g., formyl, acetyl, propionyl, butyryl, isobutyryl, valeryl, pivaloyl, and the like.

R$^4$ is selected independently from the group consisting of hydrogen and methyl.

R$^5$ is selected from the group consisting of hydrogen, lower alkyl of 1-4 carbon atoms, either straight or branched (e.g., methyl, ethyl, propyl, isopropyl, butyl, tert-butyl), vinyl, and 2,2,2-trifluoroethyl.

In addition, when R$^5$ is lower alkyl and R$^2$ is methyl, they can be joined together (with abstraction of hydrogen) to form a carbocyclic ring with from 6 to 9 members.

Also, when R$^5$ is lower alkyl and R$^2$ is hydrogen, R$^5$ can be joined to the carbon atom bearing R$^2$ and OR$^3$ to form a carbocyclic ring with from 5 to 8 members.

It is to be recognized that the carbon atom marked by an asterisk (*) and, in some instances, the carbon atoms marked by a dagger (†) are chiral. In addition, certain carbon atoms included in R$^5$ are also chiral. The compounds of this invention are understood to include the individual stereoisomers and mixtures of stereoisomers, the biological activity of which will vary but which may readily be determined in the in vitro and in vivo assays described hereinbelow.

A preferred embodiment of this invention relates to the 11,12-secoprostaglandins having the following general formula:

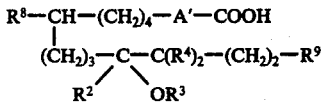

wherein A' is ethylene or oxymethylene; R$^8$ is acetyl, propionyl, 1-hydroxyethyl or 1-hydroxy-1-methylethyl; R$^2$, R$^3$, and R$^4$ are as defined above and R$^9$ is lower alkyl of 1-4 carbon atoms. In addition, when R$^2$ is methyl, R$^9$ and R$^2$ can be joined together to form a carbocyclic ring with from 6 to 9 members. Also, when R$^2$ is hydrogen, R$^9$ can be joined to the carbon bearing R$^2$ and OR$^3$ to form a carbocyclic ring with from 5 to 8 members.

BACKGROUND OF THE INVENTION

The compounds of Formula I are described as 11,12-secoprostaglandins because of their structural relationship to the naturally-occurring prostaglandins.

The prostaglandins constitute a biologically prominent class of naturally-occurring, highly-functionalized C$_{20}$ fatty acids which are anabolized readily in a diverse array of mammalian tissues from three essential fatty acids; namely, 8,11,14-eicosatrienoic acid, 5,8,11,14-eicosatetraenoic acid, and 5,8,11,14,17-eicosapentaenoic acid. Each known prostaglandin is a formal derivative of the parent compound, termed "prostanoic acid"; the latter is a C$_{20}$ fatty acid covalently bridged between carbons 8 and 12 such as to form a trans, vicinally-substituted cyclopentane in which the carboxy-bearing side chain is "alpha" or below the plane of the ring, and the other side chain is "beta" or above the plane of the ring as depicted in formula III:

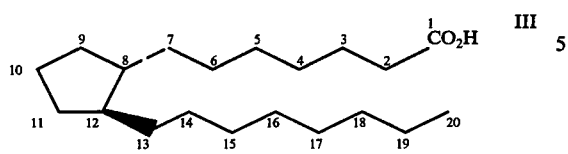

Prostaglandins have been shown to occur extensively in low concentrations in a myriad of mammalian tissues where they are both rapidly anabolized and catabolized and to exhibit a vast spectrum of pharmacological activities including prominent roles in (a) functional hyperemia, (b) the inflammatory response, (c) the central nervous system, (d) transport of water and electrolytes, and (e) regulation of cyclic AMP. Further details concerning the prostaglandins can be found in recent reviews of their chemistry [J. E. Pike, Fortschr. Chem. Org. Naturst., 28, 313 (1970) and G. F. Bundy, A. Rep. in Med. Chem., 7, 157 (1972)]; biochemistry [J. W. Hinman, A. Rev. Biochem., 41, 161 (1972)]; pharmacology [J. R. Weeks, A. Rev. Pharm., 12, 317 (1972)]; physiological significance [E. W. Horton, Physiol. Rev., 49, 122 (1969)]; and general clinical application [J. W. Hinman, Postgrad. Med. J., 46, 562 (1970)].

The potential application of natural prostaglandins as medicinally useful therapeutic agents in various mammalian disease states is obvious but suffers from three formidable major disadvantages, namely, (a) prostaglandins are known to be rapidly metabolized in vivo in various mammalian tissues to a variety of metabolites which are devoid of the desired original biological activities, (b) the natural prostaglandins are inherently devoid of biological specificity which is requisite for a successful drug, and (c) although limited quantities of prostaglandins are presently produced by both chemical and biochemical processes, their production cost is extremely high; and consequently, their availability is quite restricted.

Our interest has, therefore, been to synthesize novel compounds structurally related to the natural prostaglandins, but with the following unique advantages: (a) simplicity of synthesis leading to low cost of production; (b) specificity of biological activity which may be either of a prostaglandin-mimicking or prostaglandin-antagonizing type; (c) enhanced metabolic stability. The combination of these advantages serves to provide effective, orally and parenterally active therapeutic agents for the treatment of a variety of human and animal diseases. Included are applications in renal, cardiovascular, gastrointestinal, respiratory, and reproductive systems, and in the control of lipid metabolism, inflammation, blood clotting, skin diseases, growth hormone release, selected cancers, and certain autoimmune diseases.

The compounds of the present invention are useful as pharmaceutically active compounds. Thus, these compounds are orally active in the treatment of conditions which are responsive to the actions of the natural prostaglandins. It is, of course, necessary to determine by routine laboratory testing which of the compounds of the present invention are most suitable for a specific end use. Some of the compounds of the invention have prostaglandin-like activity in that they mimic the effect of prostaglandin $E_1$ in stimulating the formulation of cyclic AMP in the mouse ovary in vitro.

Examples of compounds which are useful in stimulating the formation of cyclic AMP in the mouse ovary are:

a) 8-acetyl-12-hydroxyheptadecanoic acid
b) 8-acetyl-13-hydroxyheptadecanoic acid
c) 8-acetyl-14-hydroxyheptadecanoic acid
d) 8-acetyl-11-hydroxyheptadecanoic acid
e) 8-acetyl-12-hydroxy-(E)-10-heptadecenoic acid
f) 8-propionyl-12-hydroxyheptadecanoic acid
g) 8-(3-hydroxypropionyl)-12-hydroxyheptadecanoic acid
h) 8-(1-hydroxyethyl)-12-hydroxyheptadecanoic acid
i) 8-hydroxymethyl-12-hydroxyheptadecanoic acid
j) 8-acetyl-12-hydroxy-16-methylheptadecanoic acid
k) 8-acetyl-12-hydroxynonadecanoic acid
l) 8-(1,3-dihydroxypropyl)-12-hydroxyheptadecanoic acid
m) 9-acetyl-12-hydroxyheptadecanoic acid
n) 8-acetyl-12-acetoxyheptdecanoic acid
o) (5-acetyl-9-hydroxytetradecyloxy)acetic acid
p) methyl 8-acetyl-12-hydroxyheptadecanoate
q) 8-glycoloyl-12-hydroxyheptadecanoic acid
r) 8-acetyl-12-hydroxy-13,13-dimethylheptadecanoic acid
s) 8-acetyl-12-hydroxy-10-heptadecynoic acid
t) 8-(1-hydroxy-1-methylethyl)-12-hydroxy-12-methylheptadecanoic acid
u) 8-acetyl-11-(1-hydroxycyclohexyl)-10-undecynoic acid
v) 8-(1-hydroxyethyl)-12-hydroxy-(E)-10-heptadecenoic acid
w) 8-(1-hydroxyethyl)-12-hydroxy-12-methylheptadecanoic acid Certain of the compounds of the invention which do not mimic the effect of prostaglandin $E_1$ are active as antagonists of prostaglandin $E_1$ in certain smooth muscle tissues, such as intestinal and uterine tissue. Such compounds would be useful in the prevention of abortion and in the treatment of diarrhea.

An example of the compounds of our invention active in antagonizing the effect of prostaglandin $E_1$ in uterus and intestinal tissue are compounds which have additional methyl substituents in the alpha position relative to the carboxy group, as for example, 2-methyl-8-acetyl-12-hydroxyheptadecanoic acid.

In addition, certain of the compounds of the present invention mimic the effects of prostaglandin $E_1$ in producing renal vasodilation in laboratory animals. Thus, they can be used to improve renal function in animals with poorly-functioning kidneys. Examples of such compounds are:

a) 8-acetyl-12-hydroxyheptadecanoic acid
b) 8-acetyl-13-hydroxyheptadecanoic acid
c) 8-acetyl-14-hydroxyheptadecanoic acid
d) 8-acetyl-11-hydroxyheptadecanoic acid
e) 8-acetyl-12-hydroxy-(E)-10-heptadecenoic acid
f) 8-propionyl-12-hydroxyheptadecanoic acid
g) 8-(1-hydroxyethyl)-12-hydroxyheptadecanoic acid
h) 8-hydroxymethyl-12-hydroxyheptadecanoic acid
i) 8-acetyl-12-hydroxynonadecanoic acid
j) 8-acetyl-12-acetoxyheptadecanoic acid
k) (5-acetyl-9-hydroxytetradecyloxy)acetic acid
l) 8-acetyl-12-hydroxy-13,13-dimethylheptadecanoic acid
m) 8-acetyl-11-(1-hydroxycyclohexyl)undecanoic acid Also, certain of the compounds of this invention have antihypertensive activity as shown by the fact that they lower blood pressure in a strain of laboratory rats which have blood pressure higher than that observed in normal rats, and thus are useful in the treatment of hypertension. An example of such a compound is 8-acetyl-12-hydroxyheptadecanoic acid.

In addition, certain of the compounds of this invention are effective in inhibiting the aggregation of platelets in blood stimulated with collagen to cause platelet aggregation. Thus, in inhibiting platelet aggregation, they are useful in preventing thrombus formation. Examples of compounds of this type are:
 a) 8-acetyl-12-hydroxyheptadecanoic acid
 b) 8-(1-hydroxyethyl)-12-hydroxyheptadecanoic acid
 c) (5-acetyl-9-hydroxytetradecyloxy)acetic acid Also, certain of the compounds of our invention, for example 8-acetyl-12-hydroxyheptadecanoic acid, may have utility as antiulcer agents in that they are active in inhibiting gastric secretion in laboratory animals. In one test used to establish this activity, dogs with a chronic gastric fistula are treated with pentagastrin, a substance which ordinarily evokes secretion in such animals. Activity in the test compound is shown when the secretion caused by the test compound is inhibited to some degree.

The compounds of this invention are also indicated to be useful in therapy as regulators of the immune response. The basis for their activity in this area is their ability to stimulate cyclic-AMP formation in cells. Agents, including the E prostaglandins, that increase cellular cyclic-AMP concentration, interfere with the cell-mediated immune response by inhibiting lymphocyte expression in response to antigen, by inhibiting release of pathological mediators from sensitized lymphocytes, and by inhibiting the killing of target cells by such lymphocytes. Various assays which depend upon the measurement of some function of the immunologically competent lymphocyte can be used to demonstrate that the prostaglandin analogs of this invention are similarly active. For example, the release of lymphokines (proteins that are agents of inflammation and tissue destruction) from sensitized lymphocytes in culture is strongly inhibited by these analogs in low concentrations. Thus, it is apparent that the compounds of this invention are applicable to the treatment of those autoimmune diseases in whose pathogenesis a cell-mediated immune reaction is involved. Such diseases range from contact dermatitis to such chronic destructive diseases as rheumatoid arthritis and possibly multiple sclerosis and systemic lupus erythematosus.

The present prostaglandin analogs are also effective in preventing the rejection of transplanted organs. The biochemical basis for this action is the same as outlined in the preceding paragraph, for the rejection of organ grafts is considered to be predominantly a cell-mediated immune phenomenon and the hallmark of organ rejection is the infiltration of cytotoxic lymphocytes into the graft. Direct evidence that the compounds of this invention can retard or prevent transplant rejection has been obtained in the rat renal allograft model; in this system, administration of the compounds of the present invention prevents the rejection of the transplanted kidney and the subsequent death of the host rat, which events invariably occur in the cases of untreated rats or those treated with immunosuppressants. An example of a compound which is an effective regulator of immune responses of the types described above is 8-acetyl-12-hydroxyheptadecanoic acid.

Because of their biological activity and ready accessibility, the compounds of the invention are also useful in that they permit large scale animal testing useful and necessary to understanding of these various disease conditions such as dwarfism caused by poorly-functioning pituitary glands, stroke (thrombus formation), and the like. It will be appreciated that not all of the compounds of this invention have these biological activities to the same degree but the choice of any particular ones for any given purpose will depend upon several factors including the disease state to be treated.

The compounds of this invention can be administered either topically or systemically, i.e., intravenously, subcutaneously, intramuscularly, orally, rectally, or by aerosolization in the form of sterile implants for long action. They can be formulated in any of a number of pharmaceutical compositions and non-toxic carriers to this end.

The pharmaceutical compositions can be sterile, injectable suspensions or solutions, or solid orally-administrable, pharmaceutically-acceptable tablets or capsules; the compositions can also be intended for sublingual administration, or for suppository use. It is especially advantageous to formulate compositions in dosage unit forms for ease and economy of administration and uniformity of dosage. "Dosage unit form" as a term used herein refers to physically discrete units suitable as unitary dosages for animal and human subjects, each unit containing a predetermined quantity of active material calculated to produce the desired biological effect in association with the required pharmaceutical means.

Illustratively, a sterile injectable composition can be in the form of aqueous or oleagenous suspensions or solutions.

The sterile injectable composition can be aqueous or oleagenous suspension or solution. Suspensions can be formulated according to the known art using suitable dispersing and wetting agents and suspending agents. Solutions are similarly prepared from the salt form of the compound. For the laboratory animals, we prefer to use incomplete Freund's adjuvant or sterile saline (9%) as carrier. For human parenteral use, such as intramuscularly, intravenously, or by regional perfusion, the diluent can be a sterile aqueous vehicle containing a preservative; for example, methylparaben, propylparaben, phenol, and chlorobutanol. The aqueous vehicle can also contain sodium chloride, preferably in an amount to be isotonic; as well as a suspending agent, for example, gum arabic, polyvinyl pyrrolidone, methyl cellulose, acetylated monoglyceride (available commercially as Myvacet from Distillation Products Industry, a division of Eastman Kodak Company, monomethyl glyceride, dimethyl glyceride or a moderately high molecular weight polysorbitan (commercially available under the tradenames Tween or Span from Atlas Powder Company, Wilmington, Del.). Other materials employed in the preparation of chemotherapeutic compositions containing the compound may include glutathione, 1,2-propanediol, glycerol and glucose. Additionally, the pH of the composition is adjusted by use of an aqueous solution such as tris(hydroxymethyl)aminomethane (tris buffer).

Oily pharmaceutical carriers can also be used, since they dissolve the compound and permit high doses. Many oily carriers are commonly employed in pharmaceutical use, such as, for example, mineral oil, lard, cottonseed oil, peanut oil, sesame oil, or the like.

It is preferred to prepare the compositions, whether aqueous or oils, in a concentration in the range of from 2-50 mg./ml. Lower concentrations require needless qualities of liquid. Higher concentrations than 50 mg./mg. are difficult to maintain and are preferably avoided.

Oral administration forms of the drug can also be prepared for laboratory animals or human patients provided that they are encapsulated for delivery in the gut. The drug is subject to enzymatic breakdown in the acid environment of the stomach. The same dosage levels can be used as for injectable forms; however, even higher levels can be used to compensate for biodegradation in the transport. Generally, a solid unit dosage form can be prepared containing from 0.5 mg. to 25 mg. active ingredient.

Whatever the mode of administration, doses in the range of about 0.10 to 20 milligrams per kilogram of body weight administered one to four times per day are used. The exact dose depending on the age, weight, and condition of the patient, and the frequency and route of administration.

The low cost and ready accessibility of the compounds of this invention make them particularly promising for applications in veterinary medicine in which field their utilities are comparable to those in human medicine.

In preparing the new chemical compounds with which this invention is concerned, we have found it desirable to use as starting materials compounds which are readily available commercially in any desired amounts.

There are a number of inter-related processes useful in preparing the compounds of formula I. These can all be described as the sub-synthesis of each of the three main moieties of the molecule (i.e., the $(CH_2)_4$A-R chain,

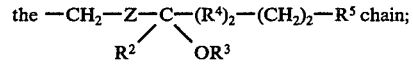

and the R' group; all attached to the asymmetric carbon atom

and then their reaction(s) to form the desired end product. Although not all compounds can be prepared by each process, there is much overlapping so that many compounds can be prepared by one, two, or three of these processes. Certain variant processes are involved and each variant of the main processes will be discussed in relation to the specific compound or compounds produced.

ACETOACETIC ACID PROCESS

One major process which can be used to prepare the compounds of this invention is the "acetoacetic ester process".

This is used to yield compounds of formula I when R' is acetyl or (following optional variant procedures) 1-hydroxyethyl and 1-hydroxy-1-methylethyl, and R, A, Z, $R^2$, $R^3$, $R^4$, and $R^5$ are as defined in formula I.

The starting material is a lower alkyl ester of acetoacetic acid,

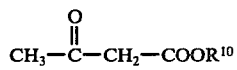                                                       IV wherein $R^{10}$ is a lower alkyl group having 1-5 carbon atoms and is preferably tert-butyl. However, when reagents VII B or VII C are employed, as discussed infra, to prepare compounds of formula I wherein Z is vinylene or ethynylene, $R^{10}$ must be methyl or ethyl.

The starting compound IV is then treated with an equivalent of base such as sodium hydride, sodium ethoxide, sodium amide, or the like. The enolate anion thus produced is alkylated with a compound of the formula:

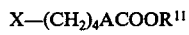                                                       V wherein X is a halogen atom, preferably bromine or chlorine, A is as defined in formula I, and $R^{11}$ is lower alkyl having 1-5 carbon atoms, preferably ethyl. The reaction of the anion from IV with V is conducted in an inert solvent or solvent system such as dimethylformamide, dimethylformamide-benzene (1:1) or diglyme, at a temperature ranging from 40° to 120° C. The reactants are employed in approximately equimolar amounts. The reaction is complete in 2-4 hours. After IV and V have reacted, the intermediate compound

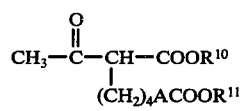                                                       VI is isolated.

Compound VI can then be treated with an equimolar amount of base such as NaH, $NaOC_2H_5$, or $NaNH_2$ and then alkylated with any one of the following reagents VII A, VII B, VII C or VII D:

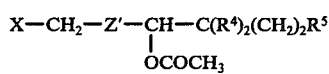   VII A

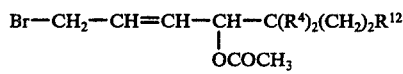   VII B

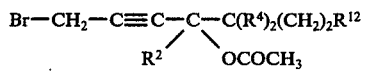   VII C

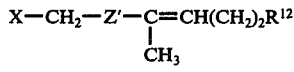   VII D wherein X is halogen, preferably chlorine or bromine, Z' is methylene, ethylene, trimethylene, and tetramethylene, $R^4$ and $R^5$ are as defined for formula I, $R^{12}$ is hydrogen, lower alkyl of 1-4 carbon atoms, straight or branched, and 2,2,2-trifluoroethyl. In intermediates VII C, when $R^{12}$ is lower alkyl and $R^2$ is methyl, they can be joined together to form a carbocyclic ring with from 6 to 9 members. Also in VII C, when $R^{12}$ is lower alkyl and $R^2$ is hydrogen, $R^{12}$ can be joined to the carbon atom bearing $R^2$ to form a carbocyclic ring with from 5 to 8 members.

Whichever of the four reagents VII are employed, the reactant compounds are employed in approximately equimolar amounts. A solvent is employed such as dimethylformamide, dimethylformamide-benzene (1:1), or diglyme. The temperature of the reaction is between 60° and 120° C. The reaction is completed within 12-72 hours.

The various intermediate products obtained, that is,

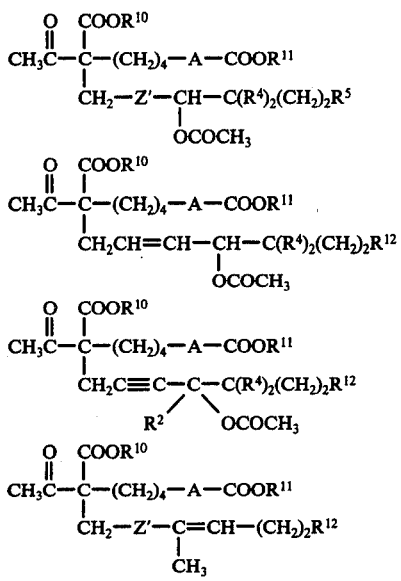

VIII A

VIII B

VIII C

VIII D are then further treated as follows to yield the final product I.

For instance, compound VIII A in which R¹⁰ is tert-butyl, is heated in solution (preferably higher boiling inert solvents are used, i.e., toluene or xylenes) with a trace of acid to effect elimination and decarboxylation. This process yields the intermediate compound IX:

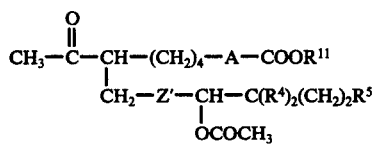

IX which is submitted to mild basic hydrolysis (preferably a dilute solution of NaOH in aqueous methanol or ethanol) to yield compounds of formula I.

Further, compound VIII A in which R¹⁰ is a primary or secondary lower alkyl group (e.g., methyl, ethyl, or butyl) can be subjected to basic hydrolysis to effect cleavage of the ester linkages and decarboxylation and to obtain compounds of formula I, i.e., X:

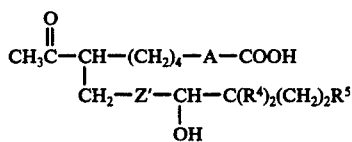

X

The compound VIII B (in which R¹⁰ must be a primary or secondary lower alkyl group, i.e., methyl, ethyl, or butyl), is submitted to basic hydrolytic conditions to effect hydrolysis and decarboxylation and obtain compounds of formula I, i.e., XI:

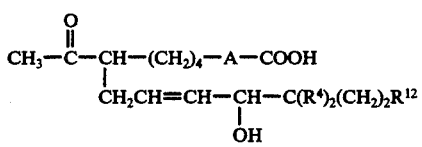

XI

The compound VIII C (in which R¹⁰ must be a primary or secondary lower alkyl group, i.e., methyl, ethyl, or butyl) is submitted to basic hydrolytic conditions to effect hydrolysis and decarboxylation and obtain compounds of formula I, i.e., XII:

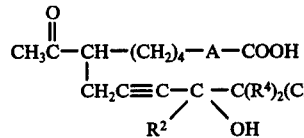

XII

Catalytic hydrogenation of compounds XII produces compounds of formula I, i.e., XIII:

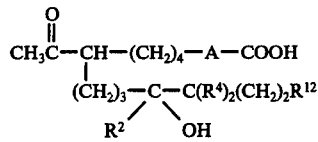

XIII

In the case of compound VIII D, if R¹⁰ is tert-butyl, the compound is first heated in an inert solvent with a trace of acid to effect elimination and decarboxylation and obtain compound XIV:

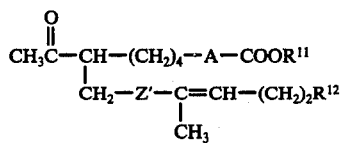

XIV

The compound XIV is hydrated by the oxymercuration-demercuration process in which XIV is treated with mercuric acetate in aqueous tetrahydrofuran for a prolonged period to effect oxymercuration followed by treatment of the reaction mixture with sodium borohydride to effect demercuration. The product of this process is compound XV:

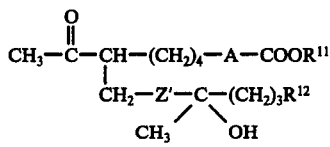

XV

Mild basic hydrolysis (NaOH in aqueous methanol or ethanol) of the ester function of compound XV yields compounds of formula I, i.e., XVI:

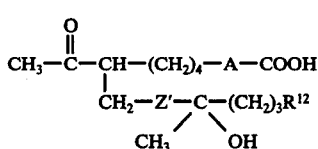

XVI

In the case of compound VIII D, if R¹⁰ is a primary or secondary alkyl group, the compound is first subjected to basic hydrolysis to cleave ester linkages and effect decarboxylation and yield compound XVII:

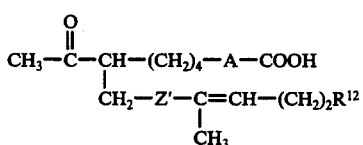

XVII

The compound XVII is hydrated by the oxymercuration-demercuration process described above to yield compounds of formula I, i.e., XVI.

It should be pointed out that the exact order of reacting compound IV with compound V or any of compounds VII is not critical; either V or VII can be the first reactant. Subsequently, the other of the reactants is reacted with the recovered intermediate. The order described above is our preferred route, however.

MALONIC ESTER PROCESS:

Another major route useful in preparing compounds of this invention is the Malonic Ester Process. This process is used to prepare a sub-group (formula XVIII) of compounds of formula I wherein

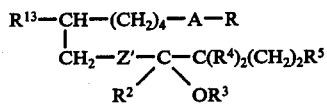
XVIII $R^{13}$ is propionyl, formyl, hydroxyacetyl, or hydroxymethyl, or following subsequent reactions, where $R^{13}$ is 1-hydroxyethyl or 1,2-dihydroxyethyl; and R, A, Z', $R^2$, $R^3$, $R^4$, and $R^5$ are as defined previously.

This process utilizes as starting material di-tert-butyl malonate.

This ester is alkylated first with compound V and then with either of compounds VII A or VII D. The basic reagents used and the reaction conditions for these alkylations are essentially the same as in the alkylations described in the acetoacetic ester process. At this point, the compounds XIX and XX are obtained:

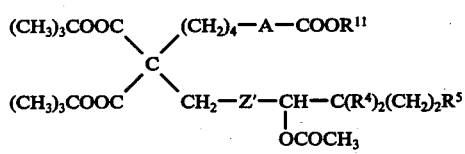
XIX

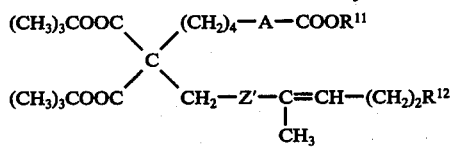
XX

Either of these compounds is heated in an inert solvent with a trace of acid to effect elimination of isobutylene and decarboxylation. Compounds XXI and XXII are obtained, respectively:

$$HOOC-CH-(CH_2)_4-A-COOR^{11} \quad \text{XXI}$$
$$\begin{vmatrix} \\ CH_2-Z'-CH-C(R^4)_2(CH_2)_2R^5 \\ | \\ OCOCH_3 \end{vmatrix}$$

$$HOOC-CH-(CH_2)_4-A-COOR^{11} \quad \text{XXII}$$
$$\begin{vmatrix} \\ CH_2-Z'-C=CH-(CH_2)_2R^{12} \\ | \\ CH_3 \end{vmatrix}$$

In turn, either of these compounds is heated with thionyl chloride at 60° to 120° C. for 2 to 6 hours in an inert solvent (e.g., benzene, toluene) to yield the acid chloride intermediates XXIII and XXIV:

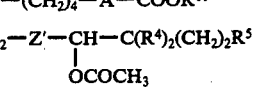
XXIII

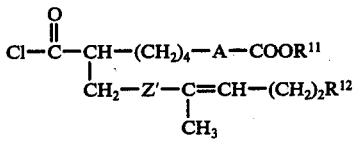
XXIV

The compounds XXIII and XXIV are key intermediates in that a variety of $R^{13}$ groups can be introduced by the reaction of reagents with the chlorocarbonyl functional group. (1) To prepare compounds where $R^{13}$ is propionyl, intermediates XXIII and XXIV are made to react with diethylcadmium. (2) To prepare compounds where $R^{13}$ is hydroxymethyl, the chlorocarbonyl function is reduced with sodium borohydride in a suitable non-protic solvent such as diglyme. (3) To prepare compounds where $R^{13}$ is formyl, the chlorocarbonyl function is reduced with lithium tri-tert-butoxyaluminum hydride. (4) To prepare compounds where $R^{13}$ is hydroxyacetyl, the intermediate XXIII or XXIV is treated with diazomethane in ether to obtain the diazomethyl ketone which on acid hydrolysis (2N $H_2SO_4$ in dioxane, preferably) gives the hydroxy-acetyl-substituted compound.

When any of these derivatives are prepared from XXIV, a hydration step is needed in which the elements of water are added across the double bond. This is effected by the oxymercuration-demercuration process described previously.

A final step in the preparation of the compounds of this invention is basic hydrolysis (sodium hydroxide, preferably, in methanol and ethanol) to hydrolyze the protecting ester functions and obtain compounds of formula I, i.e., XXV:

$$R^{13}-CH-(CH_2)_4-A-COOH \quad \text{XXV}$$
$$\begin{vmatrix} \\ CH_2-Z'-C-C(R^4)_2(CH_2)_2R^5 \\ / \quad \backslash \\ R^2 \quad OH \end{vmatrix}$$

It is frequently advantageous from a therapeutic standpoint to prepare compounds of this invention (formula I) in which the asymmetric carbon atom which bears $R^2$ and $OR^3$ is exclusively in the R or S configuration. The compounds of the instant invention, in which the $C_{12}$ carbon is in the S-configuration, have greated biological activity than those in which the $C_{12}$-carbon is in the R-configuration. The relative biopotency of either isomer is readily determined in any particular instance by use of the in vitro or in vivo assays referred to hereinabove.

In our series of 11,12-secoprostaglandins, compounds exclusively R or S at this center can be produced by employing in the acetoacetic or malonic processes, intermediates VII A or VII B which are optically active, i.e., resolved into their R and S isomeric forms.

We have found it particularly advantageous to employ an optically active reagent VII E:

$$\underset{R^2}{\overset{*}{BrCH_2C\equiv C-C-C(R^4)_2(CH_2)_2R^{12}}} \quad \text{VII E}$$
$$\text{\phantom{BrCH}}\diagdown\text{OCOCH}_3$$

in which $R^2$ and $R^{12}$ are as defined previously and the carbon atom marked with an asterisk is exclusively in either the R or S configuration.

The use of VII E in the acetoacetic ester process gives intermediates VIII E:

$$\underset{\underset{R^2}{\overset{*}{CH_2C\equiv C-C-C(R^4)_2(CH_2)_2R^{12}}}}{\overset{O\quad COOR^{10}}{\underset{\phantom{x}}{CH_3C-C-(CH_2)_4-A-COOR^{11}}}} \quad \text{VIII E}$$

in which $R^{10}$ must be a primary or secondary lower alkyl group, i.e., ethyl or methyl.

Basic hydrolysis of intermediates VIII E accompanied by decarboxylation give products of formula I, i.e., XII A, in which the carbon bearing $R^2$ and OH $$\underset{\underset{R^2}{\overset{*}{CH_2C\equiv C-C-C(R^4)_2(CH_2)_2R^{12}}}}{\overset{O}{CH_3C-CH-(CH_2)_4-A-COOH}} \quad \text{XII A}$$

is exclusively in the R or S configuration.

Catalytic hydrogenation of products XII a gives compounds of formula I, i.e., XIII a in which $$\underset{\underset{R^2}{\overset{}{(CH_2)_3-C-C(R^4)_2(CH_2)_2R^{12}}}}{\overset{O}{CH_3C-CH-(CH_2)_4-A-COOH}} \quad \text{XIII A}$$

the carbon atom bearing $R^2$ and OH is likewise exclusively in either the R or S configuration.

THE WITTIG ROUTE:

A third, major process for preparing compounds of this invention is termed the "Wittig route" since a key step therein involves the condensation of a triphenyl phosphorane with a ketone. This process permits the preparation of compounds of formula I in which Z is ethylene, $R^2$ and $R^3$ are hydrogen and R, A, $R^1$, $R^4$, and $R^5$ are defined as in formula I except when $R^1$ is hydroxyacetyl or 1,2-dihydroxyethyl.

The starting materials for this process are acid halides of the following formula:

$$X-\overset{O}{\overset{\|}{C}}-(CH_2)_4-A-COOR^{11} \quad \text{XXVI}$$

wherein $R^{11}$ is a lower alkyl group having 1-5 carbon atoms, preferably methyl or ethyl, and X is a halogen, preferably chloro.

Compounds of formula XXVI are allowed to react with the anions derived from a lower alkyl ester of acetoacetic acid, $$CH_3-\overset{O}{\overset{\|}{C}}-CH_2-COOR^{11} \quad \text{IV A}$$

wherein $R^{11}$ is a lower alkyl group having 1-5 carbon atoms, preferably methyl or ethyl; said anions are generated from reagents of type IV A via treatment with a strong base such as sodium hydride, sodium ethoxide, sodium amide or the like. This process is effected in an inert solvent, preferably benzene, toluene or the like, at a temperature of 0° to 25° for a period ranging from 2 to 24 hours and affords substitution products of formula XXVII:

$$\underset{\underset{COOR^{11}}{CH_3C-CH}}{\overset{O\quad\overset{O}{\overset{\|}{C}}-(CH_2)_4A-COOR^{11}}{\phantom{x}}} \quad \text{XXVII}$$

Treatment of compounds XXVII with an alkali metal alkoxide, preferably sodium methoxide, in an alcoholic medium, preferably methanol, at a temperature of about 0° to 25° for a period of 2 to 24 hours yields a β-keto ester of formula XXVIII:

$$\underset{\underset{COOR^{11}}{CH_2}}{\overset{O}{\overset{\|}{C}-(CH_2)_4A-COOR^{11}}} \quad \text{XXVIII}$$

Reagents of formula XXVIII are converted to their anions with an equivalent of a strong base such as sodium hydride, sodium amide, sodium methoxide or the like, and allowed to react in an inert solvent, preferably benzene, benzene-dimethylformamide (1:1) or the like, at a temperature ranging from 25° to 120° for a period of 48 to 120 hours and in the presence of a catalyst, preferably sodium iodide, with compounds of the following formula:

$$\underset{OCH_2-\phi}{X-Z''-CH-C(R^4)_2(CH_2)_2-R^5} \quad \text{XXIX}$$

where X=halogen, preferably chlorine or bromine and Z" is ethylene.

The above process provides compounds of formula XXX:

$$\underset{R^{11}OOC\diagup\phantom{xx}\diagdown Z''-\underset{OCH_2-\phi}{CH}-C(R^4)_2(CH_2)_2-R^5}{\overset{O}{\overset{\|}{C}-(CH_2)_4A-COOR^{11}}} \quad \text{XXX}$$

Treatment of compounds XXX with dilute aqueous alkali at a temperature ranging from 0° to 40° for a period of 12 to 74 hours followed by acidification and subsequent decarboxylation yields compounds of formula XXXI:

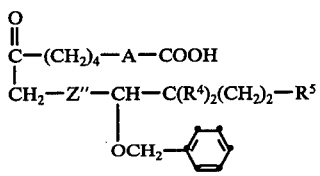

XXXI

The latter are converted to their sodium salts via treatment with a suitable base, preferably sodium hydride or sodium amide, in an inert solvent, preferably hexamethylphosphoric triamide or dimethyl sulfoxide, and allowed to react at 25° to 140° for 24 to 120 hours with the triphenyl phosphorane (Wittig reagent) derived by treatment of any one of the phosphonium salts represented by formula XXXII with a suitable strong base such as sodium hydride:

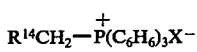

XXXII

In compounds XXXII, $R^{14}$ is methyl, ethyl, benzyloxyethyl or methoxy and X is a halide, preferably bromide or iodide. The Wittig condensation yields alkenes of formula XXXIII:

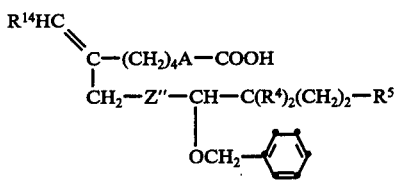

XXXIII

The latter, except where $R^{14}$ is methoxy, are treated with m-chloroperbenzoic acid in methylene chloride at 0°–5° to yield oxiranes of the type represented by formula XXXIV:

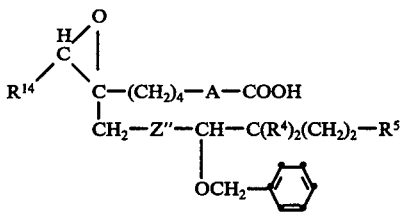

XXXIV

These compounds are then treated with boron trifluoride etherate in an inert solvent, preferably ether or the like, at 0°–5° C. to yield intermediate compounds XXXV:

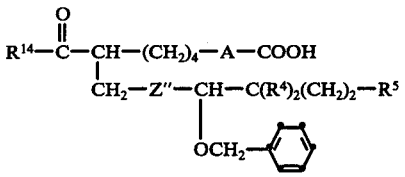

XXXV wherein $R^{14}$ is methyl, ethyl, or benzyloxyethyl.

Following removal of the benzyl blocking group by catalytic hydrogenolysis using hydrogen over palladium on charcoal, the following final products of structural formula I are obtained; namely, where R is carboxyl, $R^1$ is acetyl, propionyl or 3-hydroxypropionyl, Z is ethylene, $R^2$ and $R^3$ are hydrogen and A, $R^4$, and $R^5$ as defined previously.

Additional final products of structural formula I wherein $R^1$ is 1,3-dihydroxypropyl and R, A, Z, $R^2$, $R^3$, $R^4$, and $R^5$ are as defined above are obtained by selective ketone reduction of compounds of formula XXXV wherein $R^{14}$ is 3-benzyloxypropynyl followed by subsequent debenzylation of the resulting carbinol diethers.

Final products of structural formula I in which $R^1$ is acryloyl and R, A, Z, $R^2$, $R^3$, $R^4$, and $R^5$ are as defined above are obtained by exposure of their counterparts in which $R^1$ is 3-hydroxypropionyl to mild acidic conditions, preferably silicic acid.

Treatment of compounds of formula XXXIII wherein $R^{14}$ is methoxy under acidic conditions followed by catalytic debenzylation provides final products of formula I in which $R^1$ is formyl and R, A, Z, $R^2$, $R^3$, $R^4$, and $R^5$ are as defined above.

DERIVATIZATION OF PRODUCTS FROM THE MAJOR PROCESSES

The directly obtained products of the acetoacetic, malonic and Wittig processes described supra can be derivatized in a variety of ways to yield other products of formula I.

1. The fundamental processes yield compounds where R is carboxy. To obtain carboxy salts the acid products are dissolved in a solvent such as ethanol, methanol, glyme and the like and the solution treated with an appropriate alkali or alkaline earth hydroxide or alkoxide to yield the metal salt, or with an equivalent quantity of ammonia, amine or quaternary ammonium hydroxide to yield the amine salt. In each instance, the salt either separates from the solution and may be separated by filtration, or, when the salt is soluble it may be recovered by evaporation of the solvent. Aqueous solutions of the carboxylic acid salts can be prepared by treating an aqueous suspension of the carboxylic acid with an equivalent amount of an alkaline earth hydroxide or oxide, alkali metal hydroxide, carbonate or bicarbonate, ammonia, an amine or a quaternary ammonium hydroxide.

To obtain carboxy esters (i.e., compounds where R is alkoxycarbonyl) the acid products are treated in ether with an ethereal solution of the appropriate diazoalkane. For example, methyl esters are produced by reaction of the acid products with diazomethane. To obtain products where R is carbamoyl, substituted carbamoyl or carbazoyl the acid product is first converted to an active Woodward ester. For example, the acid product can be made to react with N-tert-butyl-5-methylisoxazolium perchlorate in acetonitrile in the presence of a base such as triethylamine to yield an active ester in which R is

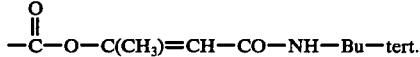

Active esters of this type can be reacted with ammonia to yield products of formula I where R is carbamoyl, with primary or secondary amines or di-loweralkylaminoalkylamines to yield products where R is substituted carbamoyl, i.e, —$CONR^6R^7$, and with hydrazine to yield products where R is carbazoyl.

2. The fundamental processes yield products where $R^3$ is hydrogen. In compounds containing no additional hydroxy group and in which $R^2$ is hydrogen, reaction with formic acid, acetic anhydride, propionic anhydride, butyric anhydride, isobutyric anhydride, valeric anhydride, pivalic anhydride and the like, without solvent and at temperatures from 25° to 60° C., gives compounds wherein $R^3$ is formyl, acetyl, propionyl, butyryl, isobutyryl, valeryl, and pivaloyl, respectively.

3. It is to be noted that in the carboxylic acid products of the fundamental processes, R' is acyl; that is, R' contains a ketone or aldehyde carbonyl group; this group can be reduced to an alcoholic functional group by the action of sodium or potassium borohydride. The following transformations are hereby effected in R': acetyl becomes 1-hydroxyethyl, hydroxyacetyl becomes 1,2-dihydroxyethyl, formyl becomes hydroxymethyl, and 3-hydroxypropionyl becomes 1,3-dihydroxypropyl. This reduction can be advantageously carried out by dissolving the acyl-containing compound in an aqueous or alcoholic solution of a base such as sodium hydroxide, sodium bicarbonate and the like and adding a 20 to 100% excess of sodium or potassium borohydride. The reaction is allowed to proceed at a temperature of from 20° to 60° for a period of 2 to 24 hours.

4. A related useful method of derivatization consists of treatment of the products of the fundamental processes with a large excess of a Grignard reagent, for example, methylmagnesium bromide. The carbonyl group of R' is thereby converted to an alcohol functional group. The following transformations in R' take place, for example, with methylmagnesium bromide: acetyl becomes 1-hydroxy-1-methylethyl; propionyl becomes 1-hydroxy-1-methylpropyl; formyl becomes 1-hydroxyethyl.

In addition, products of the fundamental processes where R' is formyl, acetyl or propionyl and $R^2$ is hydrogen can be treated with an oxidizing agent, for example, chromium trioxide, to oxidize the secondary alcoholic functional group (—C($R^2$)(OH)—) to a ketone carbonyl functional group. The resulting diketone is treated with a large excess of Grignard reagent, for example, methylmagnesium bromide. The Grignard reagent reacts at both ketone carbonyl groups. For example, when methylmagnesium bromide is employed, a methyl $R^2$ group is introduced and R', if acetyl, is transformed to 1-hydroxy-1-methylethyl.

PREPARATION OF REAGENTS

1. The reagents VII A which have the following general formula wherein X, Z', $R^4$ and $R^5$ are as described previously are prepared by two related processes:

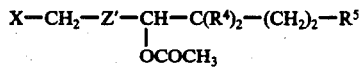   VII A a. When Z' is methylene, a Grignard reagent $R^5$—$(CH_2)_2$—$C(R^4)_2$—MgBr(or I) is allowed to react in ether or tetrahydrofuran with 3-chloro- or 3-bromopropional-dehyde to give, after hydrolysis, the alcohols X—$CH_2CH_2CH(OH)$—$C(R^4)_2$—$(CH_2)_2$—$R^5$. Treatment of the alcohols with acetyl chloride or preferably acetic anhydride with or without an inert solvent and at 25°-100° C. gives the reagents VII A where Z' is methylene.

b. When Z' is ethylene, trimethylene or tetramethylene, a Grignard reagent $R^5$—$(CH_2)_2$—$C(R^4)_2$—MgBr(or I) is allowed to react in ether or tetrahydrofuran with a nitrile X—$CH_2$—Z'—CN. The immediately resulting imine is hydrolyzed in aqueous acidic solution to give ketones of the formula X—$CH_2$—Z'—C(=O)—$C(R^4)_2$—$(CH_2)_2$—$R^5$. The ketones are reduced to the alcohols X—$CH_2$—Z'—CH(OH)—$C(R^4)_2$—$(CH_2)_2$—$R^5$ with sodium or potassium borohydride in a suitable solvent such as methanol, ethanol or diglyme. Acetylation of these alcohols preferably with acetic anhydride as described previously gives the reagents VII A where Z' is ethylene, trimethylene, or tetramethylene.

A variant of this process that is particularly useful when both $R^4$ groups are methyl consists in reacting Grignard reagents $R^5$—$(CH_2)_2$—$C(CH_3)_2$—MgCl with acid chlorides X—$CH_2Z'$—C(=O)—Cl. The resulting ketones X—$CH_2$—Z'—C(=O)—$C(CH_3)_2$—$(CH_2)_2$—$R^5$ are reduced to the alcohols X—$CH_2$—Z'—CH(OH)—$C(CH_3)_2$—$(CH_2)_2$—$R^5$ with sodium or potassium borohydride and acetylated with acetic anhydride to give the reagents VII A where Z' is ethylene, trimethylene or tetramethylene. 2. The reagents VII B which have the following general formula wherein $R^4$ and $R^{12}$ are as described previously are prepared as follows:

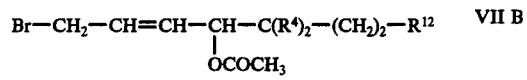   VII B

A Grignard reagent $R^{12}$—$(CH_2)_2$—$C(R^4)_2$MgBr(or I or Cl) is allowed to react with crotonaldehyde to give, after hydrolysis, the alcohols $CH_3CH$=CH—CH(OH)—$C(R^4)_2(CH_2)_2$—$R^{12}$. These alcohols are acetylated, preferably with acetic anhydride without solvent at 30°-100° C. for 2-12 hours, to give the intermediates $CH_3CH$=CH—CH(OCOCH$_3$)—$C(R^4)_2$—$(CH_2)_2$—$R^{12}$. These intermediates are allowed to react with N-bromosuccinimide in chloroform at 50°-70° C. for 2.5 to 5 hours to effect allylic bromination and give the reagents of formula VII B.

3. The reagents VI C which have the following general formula wherein $R^2$, $R^4$ and $R^{12}$ are as described previously are prepared as follows:

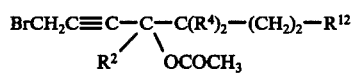   VI C

The starting materials for the process are aldehydes (when $R^2$ is hydrogen) or ketones with the structure $R^2$—C(=O)—$C(R^4)_2$—$R^{12}$. Examples of such aldehydes and ketones are hexanal, 2-methylhexanal, 2-heptanone, and (when $R^{12}$ is joined either with $R^2$ when $R^2$ is methyl or with the carbon bearing $R^2$ when $R^2$ is hydrogen as earlier specified) cyclohexanone or cyclooctanone. Such aldehydes or ketones are caused to react with lithium acetylide or ethynylmagnesium bromide to give alcohols of the structure HC≡C—$C(R^2)(OH)$—$C(R^4)_2$—$(CH_2)_2$—$R^{12}$. These alcohols are acetylated preferably with acetic anhydride in pyridine solution. The resulting acetates are heated with formaldehyde (preferably introduced in the form of paraformaldehyde) and dimethylamine or diethylamine to give amines $(Me)_2N$— or $(Et)_2NCH_2C$≡C—$C(R^2)(OCOCH_3)$—$C(R^4)_2$—$(CH_2)_2$—$R^{12}$. The amines are caused to react with cyanogen bromide preferably in ether solution at 25°-35° C. and for from 8 to 24 hours to give the reagents VI C.

The optically active reagents VII E with the following general formula in which $R^2$, $R^4$ and $R^{12}$ are as defined previously and the carbon atom marked with an asterisk is exclusively in either the R or S configuration are prepared by following exactly the procedures described immediately above. However, it is

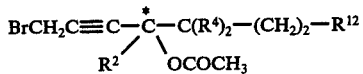    VII E necessary in these cases to resolve into their R and S enantiomers the alcohols $HC{\equiv}C-C(R^4)(OH)-C(R^4)_2-(CH_2)_2-R^{12}$ and then carry the R and S enantiomers separately through the remaining steps of the procedure. In a particularly advantageous example the alcohol arising from the reaction of lithium acetylide and hexanal, 1-octyn-3-ol, $HC{\equiv}C-CHOH-C_5H_{11}$ is resolved into its enantiomers according to published procedures and these enantiomers according to published procedures and these enantiomers converted to the R and S enantiomers of compound of formula VII E, i.e., $BrCH_2C{\equiv}C-\overset{*}{C}H(OCOCH_3)-C_5H_{11}$. The employment of these optically active reagents in the acetoacetic ester process gives rise to optically active products of formula I, i.e.,

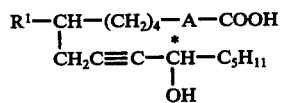

where the resolved asymmetric carbon atom is marked with an asterisk. Hydrogenation of such products give rise to further optically active products of formula I, i.e.,

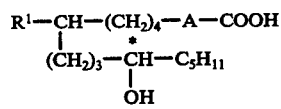

4. The reagents VII D which have the following general formula wherein X, Z' and $R^{12}$ are as

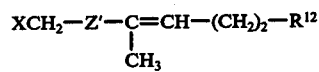    VII D described previously are prepared as follows: A grignard reagent $R^{12}(CH_2)_2CH_2MgBr$ or $R^{12}(CH_2)_2CH_2MgI$ is allowed to react with haloketones $XCH_2-Z'-C(=O)CH_3$ to give, after hydrolysis, the tertitary alcohols $X-CH_2Z'-C(OH)(CH_3)-CH_2(CH_2)_2R^{12}$. These alcohols can be dehydrated by treatment with a variety of acidic reagents and with heat to give the reagents VII C. A preferred method of dehydration involves acetylation of the alcohols with acetic anhydride, and then heating the resulting esters in an inert solvent (benzene, toluene or the like) at from 80° to 140° in the presence of a trace of an acid such as sulfuric or p-toluenesulfonic acid to effect elimination of acetic acid.

5. The preparation of reagents of formula V has been described in the scientific and patent

    V literatures in instances where A is ethylene, trimethylene, α-methylethylene, β-methylethylene, α,α-dimethylethylene, β,β-dimethylethylene. To prepare reagents where A is oxymethylene, an ester of glycolic acid, $HOCH_2COOR^{11}$ is treated with a strong base, preferably sodium hydride, in a non-protic solvent (dimethylformamide, glyme and the like) and the resulting anion caused to react with a 1,4-dihalobutane, preferably 1,4-dibromobutane. The glycolic ester and base are employed in approximately equimolar quantities, a 1.5 to 2 molar excess of the dihalobutane is advantageously used.

6. The reagents of formula XXVI

    XXVI wherein $R^{11}$, A and X are as previously defined, can be conveniently prepared from reagents V (see preceeding section, 5) via conversion of V to the 2-substituted dithianes:

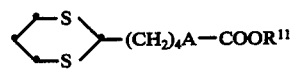

employing 2-lithiodithiane in an inert solvent, preferably ether or tetrahydrofuran, at a temperature of $-78°$ to $-20°$ for a period of 2 to 24 hours. Oxidative cleavage of the latter in an inert aqueous medium provides half acids $HOOC-(CH_2)_4-A-COOR^{11}$ which are transformed to reagents of formula XXVI employing suitable acid halide forming reagents which can be used without a solvent, preferably oxalyl or thionyl chloride, at 20° to 100° for a period of 1 to 15 hours.

7. The reagents illustrated by formula XXIX

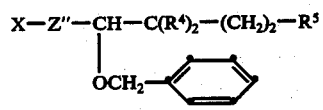    XXIX in which $R^4$, $R^5$, $Z''$ and $Z$ are as previously defined in the section describing the Wittig route, are readily prepared by the following transformations. Condensation of the Grignard reagents $BrMg-C(R^4)_2-(CH_2)_2-R^5$ with 3-chloropropionaldehyde provides alcohols

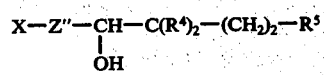

which may be reacted, without solvent, with s-trioxane and dry hydrogen chloride (g) at temperatures of $-10°$ to 20° for a period of 2 to 12 hours to yield chloromethyl ethers:

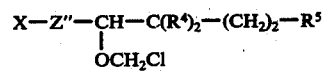

The latter, upon metathesis with phenylmagnesium bromide in an inert solvent, preferably benzene, ether or tetrahydrofuran, at a temperature of 0° to 40° for 2 to 24 hours, provide reagents XXIX.

8. The phosphonium salts of formula XXXII
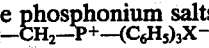    XXXII
can be prepared by allowing halides $R^{14}-CH_2-X$, where $R^{14}$ and X are as defined in the section describing the Wittig route, to react in the absence of a solvent with triphenylphosphine at a temperature of 60° to 120° for 12 to 200 hours. When R[14] is 2-benzyloxyethyl, the corresponding halide,

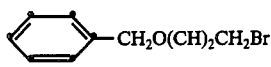

may be prepared by transformation of 3-bromopropanol to the corresponding chloromethyl ether followed by treatment of the latter with phenylmagnesium bromide; these processes were described previously in section 7.

Methods for obtaining optical antipodes of the compounds of this invention have been described supra [sections dealing with malonic acid process and preparation of intermediates (4)] whereby one of the components of the molecule is preresolved prior to its assembly into the whole molecule. Other methods also can be employed; for example, mixtures of racemates may be separated by taking advantage of the physiochemical differences between the components using chromatography and/or fractional crystallization. The racemic products and intermediates of this invention can be resolved into their optically active components by any one of a number of methods of resolution which are well described in the chemical literature.

Those compounds which are carboxylic acids can be converted to the diastereoisomeric salts by treatment with an optically active base such as + or − α-methylbenzylamine, + or − α-(1-naphthyl)-ethylamine, bromine, cinchonine, cinchonidine, or quinine. These diastereoisomeric salts can be separated by fractional crystallization.

The carboxylic acids of this invention also can be converted to esters using an optically active alcohol, such as, estradiol-3-acetate, or d- or l-menthol and the diastereoisomeric esters resolved by crystallization or by chromatographic separation.

Racemic carboxylic acids also may be resolved by reverse phase and absorption chromatography using an optically active support and absorbent.

Compounds of this invention which contain free hydroxyl groups can be esterified with acid chlorides or anhydrides derived from optically active acids, such as, (+)-10-camphorsulfonic acid, (+)-α-bromocamphor-π-sulfonic acid, or d- or 1-6,6'-dinitrodiphenic acid to form esters which can be resolved by crystallization.

Another method of obtaining pure optical isomers involves incubation of the racemic mixture with certain microorganisms such as fungi, by processes well established in the art, and recovering the product formed by the enzymatic transformation.

The methods described supra are especially effective if one applies the process to a compund where one asymmetric center has been preresolved by the techniques already described.

EXAMPLE 1

Preparation of 8-Acetyl-12-hydroxyheptadecanoic Acid

Step A: Preparation of Ethyl 8-Tert.-butoxycarbonyl-9-oxodecanoate

A suspension of 57% sodium hydride in mineral oil (37.05 g. net wt.; 0.88 mole) in a solvent mixture of benzene (400 ml.) and dimethylformamide (400 ml.) is treated, dropwise, over 30 minutes with tert.-butyl acetoacetate (126.56 g.; 0.80 mole). Stirring is continued for an additional 30 minutes. Then ethyl 7-bromoheptanoate (208.50 g.; 0.88 mole) is added, dropwise, over 30 minutes and the mixture is heated at 100° C. for 2½ hours.

The cooled reaction mixture is treated with water (1600 ml.) and the organic layer is separated. The aqueous layer is extracted with ether. The combined organic solutions are washed with saturated sodium chloride solution and then dried over anhydrous sodium sulfate. The solvents are removed under vacuum and the residual oil is distilled to give 158.6 g. (63%) of yellow oil, b.p. 175°–177°/0.5 mm.

Step B: Preparation of 1-Chloro-4-nonanone

To the Grignard reagent prepared from a mixture of amyl bromide (226.59 g.; 1.5 moles) and magnesium (36.48 g.; 1.5 moles) in ether (1000 ml.) is added, dropwise, during one hour, 4-chlorobutyronitrile (155.34 g.; 1.5 moles). Stirring is continued for an additional one hour. The reaction mixture is poured into a mixture of finely crushed ice (1000 g.) and concentrated hydrochloric acid (750 ml.). The ether layer is separated quickly and discarded. The aqueous layer is heated on a steam bath for one hour to hydrolyze the intermediate imine and cause the separation of the ketone as an oil. After cooling, the oil is extracted with ether and the combined extracts are washed with saturated sodium chloride solution and dried over anhydrous sodium sulfate. The solvent is removed under vacuum and the residual oil is distilled to give 69.0 g. (26%) of colorless oil, b.p. 115°–117°/14 mm.; pmr (CDCl$_3$) δ0.90 (3H,t), 3,56 (2H,t,CH$_2$Cl).

Step B(2): Preparation of 1-Chloro-4-nonanol

A suspension of sodium borohydride (6.62 g.; 0.175 mole) and sodium hydroxide (1.3 g.) in ethanol (310 ml.) is treated, dropwise, over 1 hour with 1-chloro-4-nonanone (61.40 g.; 0.349 mole) while the temperature is maintained at 45°–50°. Stirring is continued for one hour, longer without external cooling.

The reaction mixture is acidified with concentrated hydrochloric acid to the Congo red endpoint and then the ethanol is removed under reduced pressure. The residue is treated with water (200 ml.) and the resulting oil is extracted with ether. The combined extracts are washed with saturated sodium chloride solution and dried over anhydrous sodium sulfate. The solvent is removed under vacuum to give the title compound as a light yellow residual oil, yield 58.85 g.; ir (neat) 3400 cm$^{-1}$.

Step B(3): Preparation of 1-Chloro-4-acetoxynonane

A mixture of 1-chloro-4-nonanol (111.99 g.; 0.627 mole) and acetic anhydride (128.0 g.; 1.254 moles) is heated on a steam bath for 1½ hours.

The volatile materials are removed under reduced pressure and the residual oil is distilled to give 88.6 g. (64%) of colorless oil, b.p. 130°–133°/14 mm.; pmr (CDCl$_3$) δ0.89 (3H,t), 2.02 (3H, s CH$_3$COO), 3,53 (2H,t CH$_2$Cl), 4.89 (1H,m).

Anal. Calcd. for C$_{11}$H$_{21}$ClO$_2$: C, 59.85; H, 9.59; Found: C, 59.87; H, 9.67.

Step B(4): Preparation of Ethyl 8-Acetyl-8-tert.-butoxycarbonyl-12-acetoxyheptadecanoate A suspension of 57% sodium hydride in mineral oil (3.03 g. net wt., 0.072 mole) in a solvent mixture of benzene (40 ml.) and dimethylformamide (40 ml.) is treated, dropwise, over a period of 30 minutes with ethyl 8-tert.-butoxycarbonyl-9-oxodecanoate (20.41 g., 0.065 mole). Stirring is continued for an additional period of 30 minutes. Then 1-chloro-4-acetoxynonane (15.80 g., 0.072 mole) is added, dropwise, over 30 min. Potassium iodide (50 mg.) is added and the mixture heated at 100° for 66 hours.

The reaction mixture is cooled, treated with water (160 ml.) and the organic layer separated. The aqueous layer is extracted with ether. The combined organic extracts are washed with a saturated aqueous sodium chloride solution and then dried over anhydrous sodium sulfate. The solvents are removed by evaporation in vacuo to give a residual oil of ethyl 8-acetyl-8-tert.-butoxycarbonyl-12-acetoxyheptadecanoate. The yield is 32.04 g.; pmr (CDCl$_3$) $\delta$0.90 (3H,t), 1.45 (9H,s), 2.02 (3H,s CH$_3$COO), 2.12 (3H,s CH$_3$CO), 4.13 (2H,q).

Step C: Preparation of Ethyl 8-Acetyl-12-acetoxyheptadecanoate

A mixture of ethyl 8-acetyl-8-tert.-butoxycarbonyl-12-acetoxyheptadecanoate (32.04 g.; 0.0643 mole), p-toluenesulfonic acid monohydrate (1.10 g.) and toluene (110 ml.) is heated under reflux for 18–22 hours. The CO$_2$ evolved is indicated by bubbling the gas into aqueous Ba(OH)$_2$.

The cooled reaction mixture is washed with saturated sodium bicarbonate solution (25 ml.), saturated sodium chloride solution (2 × 25 ml.) and then dried over anhydrous sodium sulfate. The solvent is removed under vacuum to give 26.69 g. (theory 25.63 g.) of a residual oil. The oil is purified by column chromatography on silica gel with chloroform as an eluant. There is obtained 9.6 g. (38%) of ethyl 8-acetyl-12-acetoxyheptadecanoate, pmr (CDCl$_3$) $\delta$0.90 (3H,t), 2.02 (3H,s CH$_3$COO), 2.12 (3H, s CH$_3$CO), 4.13 (2H,q), 4.84 (1H, m HCOCOCH$_3$).

Anal. Calcd. for C$_{23}$H$_{42}$O$_5$: C, 69.31; H, 10.62, Found: C, 69,.47; H, 10.83

Step D: Preparation of 8-Acetyl-12-hydroxyheptadecanoic Acid

Ethyl 8-acetyl-12-acetoxyheptadecanoate (12.21 g., 0.0306 mole) is added to a solution of sodium hydroxide (3.67 g., 0.0918 mole) in water (17 ml.) and methanol (153 ml.). The resulting solution is allowed to stand for 72 hours at 25° C. Most of the methanol is removed by evaporation in vacuo. The residual solution is diluted with water (150 ml.) and extracted with ether. The aqueous layer is acidified to Congo red paper with concentrated hydrochloric acid. The product, which separates as a viscous liquid, is extracted with ether. The ether extract is washed with water.

The ether extract is dried over anhydrous sodium sulfate and evaporated in vacuo to produce 9.65 g. (95%) of 8-acetyl-12-hydroxyheptadecanoic acid as a viscous yellow liquid. This material is purified by column chromatography on silica gel with 2% methanol in chloroform as the eluant. There is obtained 6.9 g. (69%) of pure 8-acetyl-12-hydroxyheptadecanoic acid as a colorless liquid, pmr (CDCl$_3$) $\delta$0.88 (3H,t), 2.12 (3H, S CH$_3$CO), 3.64 (1H, m $\underline{H}$COH), 6.65 (2H, s OH and COOH).

Anal. Calcd. for C$_{19}$H$_{36}$O$_4$: C, 69.47; H, 11.05; Found: C, 69.55; H, 11.22

EXAMPLE 2

Preparation of 8-Acetyl-12-hydroxyheptadecanoic Acid

Step A: 1-Nonen-4-ol

Magnesium (60.6 g., 2.5 moles) is suspended by stirring in ether (500 ml.) and the mixture cooled in an ice bath while allyl chloride (91.8 g., 1.2 moles) is added dropwise during 2.5 hours. Hexanal (100 g., 1.0 mole) is then added dropwise to the suspension of allyl magnesium chloride during one hour. The reaction mixture is then stirred without cooling for an additional 1.5 hours.

The mixture is poured onto ice acidified with concentrated hydrochloric acid. The ether layer is separated, washed with water, and dried over sodium sulfate. The ether is evaporated and the crude product is distilled to obtain 102.3 g. (72%) of colorless oil, b.p. 88°–90°/15 mm.

Step B: 4-Acetoxy-1-nonene

A mixture of 1-nonen-4-ol (87.5 g., 0.616 mole) and acetic anhydride (125.8 g., 1.23 moles) is heated at 100° for 1.5 hours. Distillation of the reaction mixture yields 93.2 g. (82%) of 4-acetoxy-1-nonene, a colorless oil, b.p. 89°–91°/14 mm.

Step C: 1-Bromo-4-acetoxynonane

A solution of 4-acetoxy-1-nonene (18.4 g., 0.1 mole) and benzoyl peroxide (200 mg.) in hexane (125 ml.) is stirred and cooled in an ice bath. Hydrogen bromide gas is bubbled into the solution until 9.0 g. (0.11 mole) is absorbed. This uptake of hydrogen bromide takes place in 50 minutes. The solution is allowed to stand without cooling for 1.5 hours. It is then washed with dilute sodium bicarbonate solution and water and dried over sodium sulfate. The hexane is evaporated and the residual oil distilled to obtain 13.8 g. (52%) of 1-bromo-4-acetoxynonane, a colorless oil, b.p. 98°–100°/0.3 mm.; pmr (CDCl$_3$) $\delta$0.87 (3H,t), 2.02 (3H,s, CH$_3$COO), 3.42 (2H,t, BrCH$_2$), 4.91 (1H,m,HC-O).

Step D: Preparation of Ethyl 8-Acetyl-8-tert.-butoxycarbonyl-12-acetoxyheptadecanoate The preparation of this compound is carried out as described in Example 1, Step B(4), except that an equimolar quantity of 1-bromo-4-acetoxynonane is used instead of the 1-chloro-4-acetoxynonane.

Step E: Preparation of Ethyl 8-Acetyl-12-acetoxyheptadecanoate

This preparation is carried out as described in Example 1, Step C.

Step F: Preparation of 8-Acetyl-12-hydroxyheptadecanoic Acid

This preparation is carried out as described in Example 1, Step D.

EXAMPLE 3

Preparation of 8-Acetyl-13-hydroxyheptadecanoic Acid

Step A: Preparation of 1-Chloro-5-nonanone

This compound is prepared essentially by the same procedure as described in Example 1, Step B, using the following reagents:

| | |
|---|---|
| 1-Bromobutane | 51.66 g. (0.377 mole) |
| Magnesium | 9.17 g. (0.377 mole) |
| Ether | 380 ml. |
| 5-Chlorovaleronitrile | 44.19 g. (0.377 mole) |

1-Chloro-5-nonanone is obtained as a colorless oil, yield 16.65 g. (25%), b.p. 125°–127°/13 mm.; pmr (CDCl$_3$) δ0.90 (3H,t), 3.53 (2H, t CH$_2$Cl).

Anal. Calcd. for C$_{19}$H$_{17}$ClO: C, 61.18; H, 9.70; Found: C, 60.96; H, 9.63

Step A(2): Preparation of 1-Chloro-5-nonanol

This compound is prepared essentially by the same procedure as described in Example 1, Step B(2), using the following reagents:

| | |
|---|---|
| Sodium Borohydride | 5.17 g. (0.136 mole) |
| Sodium Hydroxide | 1.00 g. |
| Ethanol | 240 ml. |
| 1-Chloro-5-nonanone | 48.10 g. (0.272 mole) |

1-Chloro-5-nonanol is obtained as a colorless residual oil, yield 48.61 g.; ir (neat) 3400 cm$^{-1}$.

Step A(3): Preparation of 1-Chloro-5-acetoxynonane

This compound is prepared essentially by the same procedure as described in Example 1, Step B(3), using the following reagents:

| | |
|---|---|
| 1-Chloro-5-nonanol | 48.61 g. (0.272 mole) |
| Acetic anhydride | 55.49 g. (0.544 mole) |

1-Chloro-5-acetoxynonane is obtained as a colorless oil, yield 52.0 g. (87%), b.p. 130–134°/13 mm.; pmr (CDCl$_3$) δ0.90 (3H,t), 2.03 (3H, s CH$_3$COO), 3.53 (2H,t CH$_2$Cl), 4.89 (1H, m).

Anal. Calcd. for C$_{11}$H$_{21}$ClO$_2$: C, 59.85; H, 9.59; Found: C, 59.98; H, 9.95

Step A(4): Preparation of Ethyl 8-Acetyl-8tert.-butoxycarbonyl-13-acetoxyheptadecanoate This compound is prepared essentially by the same procedure as described in Example 1, Step B(4) (except a trace of potassium iodide is added just prior to heating and then the heating period at 100° is continued for 67 hours), using the following reagents:

| | |
|---|---|
| Sodium hydride (57% in mineral oil) | 5.90 g. net wt. (0.140 mole) |
| Benzene | 65 ml. |
| Dimethylformamide | 65 ml. |
| Ethyl 8-tert.-butoxycarbonyl-9-oxodecanoate | 39.93 g. (0.127 mole) |
| 1-Chloro-5-acetoxynonane | 30.90 g. (0.140 mole) |
| Potassium iodide | Trace |

Ethyl 8-acetyl-8-tert.-butoxycarbonyl-13-acetoxyheptadecanoate is obtained as a residual oil, yield, 62.15 g.; pmr (CDCl$_3$) δ0.89 (3H,t), 1.45 (9H,s), 2.20 (3H, s CH$_3$COO), 2.10 (3H, s CH$_3$CO), 4.13 (2H,q).

Step B: Preparation of Ethyl 8-Acetyl-13-acetoxyheptadecanoate

This compound is prepared essentially by the same procedure as described in Example 1, Step C (except reflux time is 48 hours), using the following reagents:

| | |
|---|---|
| Ethyl 8-acetyl-8-tert.-butoxycarbonyl-13-acetoxyheptadecanoate | 62.15 g. (0.125 mole) |
| p-Toluenesulfonic acid monohydrate | 2.20 g. |
| Toluene | 220 ml. |

Ethyl 8-acetyl-13-acetoxyheptadecanoate is obtained as a residual oil, yield 48.3 g. The oil is purified by column chromatography on silica gel with chloroform as an eluant; pmr (CDCl$_3$) δ0.90 (3H,t), 2.03 (3H,s CH$_3$COO), 2.10 (3H, s CH$_3$CO), 4.13 (2H,q).

Step C: Preparation of 8-Acetyl-13-hydroxyheptadecanoic Acid

This compound is prepared essentially by the same procedure as described in Example 1, Step D, using the following reagents:

| | |
|---|---|
| Ethyl 8-acetyl-13-acetoxyheptadecanoate | 8.70 g. (0.0219 mole) |
| Sodium hydroxide | 2.63 g. (0.0657 mole) |
| Water | 12.5 ml. |
| Methanol | 112.5 ml. |

8-Acetyl-13-hydroxyheptadecanoic acid is obtained as a yellow oil, yield 5.12 g. (71%); pmr (CDCl$_3$) δ0.90 (3H,t) 2.10 (3H,s CH$_3$CO), 7.52 (2H, s OH, COOH).

Anal. Calcd. for C$_{19}$H$_{36}$O$_4$: C, 69.47; H, 11.05; Found: C, 69.81; H, 11.03

EXAMPLE 4

Preparation of 8-Acetyl-14-hydroxyheptadecanoic Acid

Step A(1): Preparation of 1-Bromo-6-nonanone

This compound is prepared essentially by the same procedure as described in Example 1, Step B(1), using the following reagents:

| | |
|---|---|
| 1-Bromopropane | 36.90 g. (0.30 mole) |
| Magnesium | 7.30 g. (0.30 mole) |
| Ether | 300 ml. |
| 6-Bromocepronitrile | 52.81 g. (0.30 mole) |

1-Bromo-6-nonanone is obtained as a light yellow oil, yield 14.36 g. (23%), b.p. 133°–135°/13 mm.; pmr (CDCl$_3$) δ0.90 (3H,t), 3.43 (2H,t CH$_2$Br).

Step A(2): Preparation of 1Bromo-6nonanol

This compound is prepared essentially by the same procedure as described in Example 1, Step B(2), using the following reagents:

| | |
|---|---|
| Sodium borohydride | 3.82 g. (0.101 mole) |
| Sodium hydroxide | 0.75 g. |
| Ethanol | 180 ml. |
| 1-Bromo-6-nonanone | 44.74 g. (0.202 mole) |

1-Bromo-6-nonanol is obtained as a light yellow residual oil, yield, 42.76 g.; ir (neat) 3400 cm$^{-1}$.

Step A(3): Preparation of 1-Bromo-6-acetoxynonane

This compound is prepared essentially by the same procedure as described in Example 1, Step B(3), using the following reagents:

| | |
|---|---|
| 1-Bromo-6-nonanol | 42.76 g. (0.192 mole) |
| Acetic anhydride | 39.17 g. (0.384 mole) |

1-Bromo-6-acetoxynonane is obtained as a colorless oil, yield 32.2 g. (63%), b.p. 142°–145°/13 mm.; pmr (CDCl$_3$) δ0.90 (3H,t), 2.03 (3H,s, CH$_3$COO), 3.45 (2H,t CH$_2$Br), 4.93 (1H, m).

Step A(4): Preparation of Ethyl 8-Acetyl-8-tert.-butoxycarbonyl-14-acetoxyheptadecanoate This compound is prepared essentially by the same procedure as described in Example 1, Step B(4) (except a trace of potassium iodide is added just prior to heating and then the heating period at 100° is continued for 21 hours), using the following reagents:

| | |
|---|---|
| Sodium hydride (57% in mineral oil) | 5.10 g. net wt. (0.121 mole) |
| Benzene | 55 ml. |
| Dimethylformamide | 55 ml. |
| Ethyl 8-tert.-butoxycarbonyl-9-oxodecanoate | 34.59 g. (0.110 mole) |
| 1-Bromo-6-acetoxynonane | 32.20 g. (0.121 mole) |
| Potassium iodide | Trace |

Ethyl 8-acetyl-8-tert.-butoxycarbonyl-14-acetoxyheptadecanoate is obtained as a residual oil, yield, 54.86 g.; pmr (CDCl$_3$)δ0.90 (3H,t), 2.01 (3H,s CH$_3$COO), 2.0 (3H,s CH$_3$CO), 4.10 (2H, q).

Step B: Preparation of Ethyl 8-Acetyl-14-acetoxyheptadecanoate

This compound is prepared essentially by the same procedure as described in Example 1, Step C (except reflux time is 23 hours), using the following reagents:

| | |
|---|---|
| Ethyl 8-acetyl-8-tert.-butoxycarbonyl-14-acetoxyheptadecanoate | 54.86 g. (0.110 mole) |
| p-Toluenesulfonic acid monohydrate | 1.95 g. |
| Toluene | 195 ml. |

Ethyl 8-acetyl-14-acetoxyheptadecanoate is obtained as a residual oil, yield 43.84 g. The oil is purified by column chromatography on silica gel with chloroform as an eluant, pmr (CDCl$_3$) δ0.90 (3H,t), 2.03 (3H,s CH$_3$COO), 2.10 (3H,s CH$_3$CO), 4.12 (2H,q).

Step C: Preparation of 8-Acetyl-14-hydroxyheptadecanoic Acid

This compound is prepared essentially by the same procedure as described in Example 1, Step D, using the following reagents:

| | |
|---|---|
| Ethyl 8-acetyl-14-acetoxyheptadecanoate | 9.20 g. (0.0231 mole) |
| Sodium hydroxide | 2.80 g. (0.0700 mole) |
| Water | 15 ml. |
| Methanol | 140 ml. |

8-Acetyl-14-hydroxyheptadecanoic acid is obtained as a yellow oil, yield 6.1 g. (80%); pmr (CDCl$_3$) δ0.90 (3H,t), 2.10 (3H,s CH$_3$CO), 6.90 (2H,s OH,COOH).

Anal. calcd. for C$_{19}$H$_{36}$O$_4$: C, 69.47; H, 11.05; Found: C, 69.46; H, 11.04

EXAMPLE 5

Preparation of 8-Acetyl-11-hydroxyheptadecanoic Acid

Step A(1): Preparation of 1-Chloro-3-nonanol

To the Grignard reagent prepared from a mixture of 1-bromohexane (73.90 g.; 0.460 mole) and magnesium (11.04 g.; 0.460 mole) in ether (450 ml.), is added, dropwise, during one hour, a solution of 3-chloropropanol (37.40 g.; 0.400 mole) in ether (200 ml.). Stirring and refluxing are continued for an additional one hour.

The reaction mixture is poured into a mixture of finely crushed ice (600 g.) and concentrated hydrochloric acid (225 ml.). The ether layer is separated washed well with water and dried over anhydrous sodium sulfate. The solvent is removed under vacuum and the residual oil is distilled to give 25.0 g. (35%) of yellow oil, b.p. 123–126°/14 mm.; pmr (CDCl$_3$) δ0.88 (3H,t), 2.07 (1H,s OH), 3.67 (2H,t CH$_2$Cl).

Step A(2): Preparation of 1-Chloro-3-acetoxynonane

This compound is prepared essentially by the same procedure as described in Example 1, Step B(3), using the following reagents:

| | |
|---|---|
| 1-Chloro-3-nonanol | 106.70 g. (0.60 mole) |
| Acetic anhydride | 122.40 g. (1.20 moles) |

1-Chloro-3-acetoxynonane is obtained as a colorless oil, yield 115.9 g. (87%), b.p. 133°–135°/14 mm.; pmr (CDCl$_3$) δ0.88 (3H,t), 2.03 (3H,s CH$_3$COO), 3.53 (2H,t CH$_2$Cl), 5.02(1H,m).

Anal. Calcd. for C$_{11}$H$_{21}$ClO$_2$: c, 59.85; H, 9.59; Found: C, 59.78; H, 9.64

Step A(3): Preparation of Ethyl 8-Acetyl-8-tert.-butoxycarbonyl-11-acetoxyheptadecanoate This compound is prepared essentially by the same procedure as described in Example 1, Step B(4), (except a trace of potassium iodide is added just prior to heating and then the heating period at 100° is continued for 20 hours), using the following reagents: j

| | |
|---|---|
| Sodium hydride (57% in mineral oil) | 5.90 g. net wt. (0.140 mole) |
| Benzene | 65 ml. |
| Dimethylformamide | 65 ml. |
| Ethyl 8-tert.-butoxycarbonyl-9-oxodecanoate | 39.93 g. (0.127 mole) |
| 1-Chloro-3-acetoxynonane | 30.90 g. (0.140 mole) |
| Potassium iodide | Trace |

Ethyl 8-acetyl-8tert.-butoxycarbonyl-11-acetoxyheptadecanoate is obtained as a residual oil, yield 61.30 g.; pmr (CDCl$_3$) δ0.88 (3H,t), 2.03 (3H,s CH$_3$COO), 2.12 (3H,s CH$_3$CO), 4.15 (2H,q).

Step B: Preparation of Ethyl 8-Acetyl-11-acetoxyheptadecanoate

This compound is prepared essentially by the same procedure as described in Example 1, Step C (except reflux time is 65 hours), using the following reagents:

| | |
|---|---|
| Ethyl 8-acetyl-8-tert.-butoxy-carbonyl-11-acetoxyheptadecanoate | 61.30 g. (0.123 mole) |
| p-Toluenesulfonic acid monohydrate | 2.20 g. |
| Toluene | 220 ml. |

Ethyl 8-acetyl-11-acetoxyheptadecanoate is obtained as a residual oil, yield 48.6 g. The oil is purified by column chromatography on silica gel with chloroform as an eluant; pmr (CDCl$_3$) δ0.88 (3H,t), 2.02 (3H,s CH$_3$COO), 2.10 (3H,s CH$_3$CO), 4.13 (2H,q).

Step C: Preparation of 8-Acetyl-11-hydroxyheptadecanoic Acid

Ethyl 8-acetyl-11-acetoxyheptadecanoate (6.5 g., 0.016 mole) is added to a solution of sodium hydroxide (2.0 g., 0.05 mole) in water (9 ml.) and methanol (81 ml.). The resulting solution is allowed to stand at room temperature for 71 hours.

Most of the methanol is then evaporated in vacuo. The residual solution is diluted with water (80 ml.) and extracted with ether. The aqueous layer is acidified with concentrated hydrochloric acid to the Congo Red endpoint. The product precipitates as an oil. It is purified by column chromatography on silica gel with 4% methanol in chloroform as eluant. There is obtained 1.3 g. of colorless oil showing a single spot, Rf 0.05, on thin-layer chromatography on silica gel with 5% methanol in chloroform as eluant. The nmr spectrum indicates that 8-acetyl-11-hydroxyheptadecanoic acid exists in equilibrium with its hemiketal, 2-methyl-2-hydroxy-3-(6-carboxyhexyl)-6-hexyltetrahydropyran. pmr (CDCl$_3$) δ0.88 (3H,t), 2.13 (less than 2H,s, CH$_3$CO), 3.6 (1H,m CH—O), 6.62 (2H,s, COOH, OH).

Anal. Calcd. for C$_{19}$H$_{36}$O$_4$: C, 69.47; H, 11.05; Found: C, 69.50; H, 11.23

EXAMPLE 6

Preparation of 8-Acetyl-12-hydroxy-(E)-10-heptadecenoic Acid

Step A: Preparation of Diethyl 2-Acetylazelate

This compound is prepared essentially by the same procedure as described in Example 1, Step A, using the following reagents:

| | |
|---|---|
| Sodium hydride (57% in mineral oil) | 3.58 g. net wt. (0.085 mole) |
| Benzene | 40 ml. |
| Dimethylformamide | 40 ml. |
| Ethyl acetoacetate | 10.02 g. (0.077 mole) |
| Ethyl 7-bromoheptanoate | 20.16 g. (0.085 mole) |

Diethyl 2-acetylazelate is obtained as a light yellow oil, yield 15.4 g. (70%), b.p. 155°–157°/0.05 mm.; pmr (CDCl$_3$)δ2.20 (3H,s), 3.40 (1H,t), 4.15 (4H,m).

Step B(1): Preparation of 1-Bromo-4-acetoxy-2-nonene

A mixture of 4-acetoxy-2-nonene (73.5 g., 0.4 mole), N-bromosuccinimide (80.0 g., 0.45 mole), and carbon tetrachloride (500 ml.) is boiled under reflux for 3 hours. The mixture is then cooled and the suspended succinimide, removed by filtration. The carbon tetrachloride solution is washed with dilute sodium bicarbonate solution and water, and is dried over sodium sulfate. The carbon tetrachloride is evaporated in vacuo and the residual oil is distilled to yield 62 g. (59%) of 1-bromo-4-acetoxy-2-nonene as a light yellow oil, b.p. 110°–112°/0.1 mm.

Step B(2): Preparation of Diethyl 2-Acetyl-2-(4-acetoxy-2-nonen-1-yl)azelate This compound is prepared essentially by the same procedure as described in Example 1, Step B(4) (except heating period at 100° is one hour), using the following reagents:

| | |
|---|---|
| Sodium hydride (57% in mineral oil) | 2.49 g. net wt. (0.0592 mole) |
| Benzene | 30 ml. |
| Dimethylformamide | 30 ml. |
| Diethyl 2-acetylazelate | 15.40 g. (0.0538 mole) |
| 1-Bromo-4-acetoxy-2-nonene | 15.57 g. (0.0592 mole) |

Diethyl 2-acetyl-2-(4-acetoxy-2-nonen-1-yl)azelate is obtained as a residual oil, yield 25.21 g.; pmr (CDCl$_3$) δ2.02 (3H,s CH$_3$COO), 2.12 (3H,s CH$_3$CO), 4.16 (4H,m), 5.26 (1H,m), 5.50 (2H,m, CH=CH).

Step C: Preparation of 8-Acetyl-12-hydroxy-(E)-10-heptadecenoic Acid

A solution of diethyl 2-acetyl-2-(4-acetoxy-2-nonen-1-yl)azelate (22.9 g., 0.049 mole) and sodium hydroxide (15.7 g., 0.392 mole) in water (150 ml.) and ethanol (150 ml.) is boiled under reflux for 2 hours. Solvents are removed under reduced pressure, the residue is dissolved in water, and the solution extracted with ether. The aqueous layer is acidified with concentrated hydrochloric acid to the Congo Red endpoint. The crude product separates as an oil, weight 18.9 g. 8-Acetyl-12-hydroxy-(E)-10-heptadecenoic acid is isolated in pure condition from the crude product by chromatography on silica gel with 4% methanol in chloroform as the eluant. There is obtained 3.5 g. of yellow oil showing a single spot, Rf 0.63, in thin layer chromatography (silica gel, 1% acetic acid in ether); pmr (CDCl$_3$) δ0.88 (3H,t), 2.10 (3H,s, CH$_3$C=O), 4,03 (1H,m HCO), 5.50 (2H,m, HC=CH), 6.58 (2H,s COOH, OH).

Anal. Calcd. for C$_{19}$H$_{34}$O$_4$: C, 69.90; H, 10.50; Found: C, 70.17; H, 10.70

EXAMPLE 7

Preparation of 8-Propionyl-12-hydroxyheptadecanoic Acid

Step A: Preparation of Di-tert.-butyl (6-ethoxycarbonylhexyl)malonate

This compound is prepared by a procedure somewhat similar to that described in Example 1, Step A (except heating period at 100° is 4½ hours), using the following reagents:

| | |
|---|---|
| Sodium hydride (57% in mineral oil) | 8.84 g. net wt. (0.21 mole) |
| Benzene | 95 ml. |
| Dimethylformamide | 95 ml. |
| Di-tert.-butyl (6-ethoxycarbonylhexyl)malonate | 41.09 g. (0.19 mole) |
| Ethyl 7-Bromoheptanoate | 49.80 g. (0.21 mole) |

Di-tert.-butyl (6-ethoxycarbonylhexyl)-malonate is obtained as a residual oil, yield 70.78 g.

Step B: Preparation of Di-tert.-butyl 2-(4-acetoxynonyl)-2-(6-ethoxycarbonylhexyl)malonate This compound is prepared essentially by the same procedure as described in Example 1, Step B(4) (except heating period at 100° is 42 hours), using the following reagents:

| | |
|---|---|
| Sodium hydride (57% in mineral oil) | 8.84 g. net wt. (0.21 mole) |
| Benzene | 95 ml. |
| Dimethylformamide | 95 ml. |
| Di-tert.-butyl (6-ethoxycarbonylhexyl)malonate | 69.70 g. (0.187 mole) |
| 1-Chloro-4-acetoxynone | 46.35 g. (0.21 mole) |

Di-tert.-butyl 2-(4-acetoxy nonyl)-2-(6-ethoxycarbonylhexyl)malonate is obtained as a residual oil, yield 104.12 g.; pmr (CDCl$_3$) $\delta$0.88 (3H,t), 1.45 (18H,s), 2.00 (3H,s CH$_3$COO), 4.12 (2H,q).

Step C: Preparation of Ethyl 8-Carboxy-12-acetoxyheptadecanoate

This compound is prepared essentially by the same procedure as described in Example 1, Step C (except reflux time is 9½ hours), using the following reagents:

| | |
|---|---|
| Di-tert.-Butyl 2-(4-acetoxynonyl)-2-(6-ethoxycarbonylhexyl)malonate | 104.12 g. (0.187 mole) |
| p-Toluenesulfonic acid monohydrate | 3.30 g. |
| Toluene | 330 ml. |

Ethyl 8-carboxy-12-acetoxyheptadecanoate is obtained as a residual oil, yield 74.90 g. The oil is purified by column chromatography on silica gel with 2% methanol in chloroform as an eluant; pmr (CDCl$_3$)$\delta$0.88 (3H,t), 2.02 (3H,s CH$_3$COO), 4.12 (2H,q), 10.97 (1H,s COOH).

Anal. Calcd. for C$_{22}$H$_{40}$O$_6$: C, 65.97; H, 10.07; Found: C, 66.24; H, 10.29

Step D: Preparation of Ethyl 8-Chlorocarbonyl-12-acetoxyheptadecanoate

A solution of ethyl 8-carboxy-12-acetoxyheptadecanoate (12.0 g., 0.03 mole) and thionyl chloride (7.2 g., 0.06 mole) in benzene (50 ml.) is refluxed for 2.5 hours. Volatile materials are removed by using a rotary evaporator in vacuo. The residual product, ethyl 8-chlorocarbonyl-12-acetoxyheptadecanoate, is a viscous liquid weighing 12.5 g. (100%), ir (neat) 1790 cm$^{-1}$(acid chloride C=O), 1730 cm$^{-1}$ (ester C=O). This material is used directly in the next step.

Step E: Preparation of Ethyl 8-Propionyl-12-acetoxyheptadecanoate

A solution of ethylmagnesium bromide in ether (100 ml.) is prepared in the usual manner from ethyl bromide (5.5 g.; 0.05 mole) and magnesium (1.2 g.; 0.05 mole). The solution is chilled to 5° and cadmium chloride (5.5 g.; 0.03 mole) is added. The mixture is stirred 10 minutes without cooling and then boiled under reflux for 30 min. Most of the ether is then allowed to distill; benzene (100ml.) is added and about half of this solvent is allowed to distill. The mixture is then diluted with benzene (50 ml.), heated to reflux, and ethyl 8-chlorocarbonyl-12-acetoxyheptadecanoate (12.5 g.; 0.03 mole) is added, dropwise, during 20 minutes. After a further reflux period of 2 hours, the mixture is cooled and treated with a 10% solution of sulfuric acid. The benzene layer is separated, washed with water and dried over sodium sulfate. The benzene is evaporated leaving a residual oil.

The product, a yellowish oil, is purified not by distillation but by column chromatography on silica gel with chloroform as eluant. There is obtained 6.2 g. of ethyl 8-propionyl-12-acetoxyheptadecanoate, showing a single spot, Rf 0.23, on thin layer chromatography (silica gel-chloroform); pmr (CDCl$_3$) $\delta$ 2.04 (3H,s, CH$_3$COO), 2.32 (5H,m) 4.15 (2H,g), 4.87 (1H,m,HCO). Anal Calcd. for C$_{24}$H$_{44}$O$_5$: C, 69.86; H, 10.75 Found: C, 69.57; H, 10.83.

Step F: Preparation of 8-Propionyl-12-hydroxyheptadecanoic Acid

This compound is prepared essentially by the same procedure described in Example 1, Step D, using the following reagents:

| | |
|---|---|
| Ethyl 8-propionyl-12-acetoxyheptadecanoate | 6.0 g. (0.146 mole) |
| Sodium hydroxide | 1.0 g. (0.025 mole) |
| Water | 10 ml. |
| Methanol | 70 ml. |

8-Propionyl-12-hydroxyheptadecanoic acid is purified by column chromatography on silica gel with chloroform as eluant. There was obtained 2.4 g. of 8-propionyl-12-hydroxyheptadecanoic acid as a light yellow oil showing a single spot, Rf 0.18, in thin layer chromatography (silica gel-3% methanol in chloroform); pmr (CDl$_3$)67 2.35 (5H,m), 3.55 (1H,m,HCO), 6.70 (2H,s,COOH,OH).

Anal. Calcd. for C$_{20}$H$_{38}$O$_4$: C, 70.13; H, 11.18; Found: C, 70.34; H, 11.69

EXAMPLE 8

Preparation of 8-(3-Hydroxypropionyl)-12-hydroxyheptadecanoic Acid

Step A: Preparation of Dimethyl 3-Oxosebacoate

Methyl acetoacetate (81 g., 0.7 mole) is added dropwise at 60° to a suspension of 57% sodium hydride in mineral oil (25.8 g., 0.6 mole) in dry benzene (1.2 l.). After standing at 25° for 1½ hours, the reaction mixture is treated with 7-carbomethoxyheptanoyl chloride (103.33 g., 0.5 mole), added over 178 hour. The resulting colorless mixture is stored at 25° overnight, cooled to 0° and diluted with water. After separating the layers, the aqueous phase is acidified and extracted with benzene. The combined organic extract is washed with water until the washings are neutral, dried over magnesium sulfate and evaporated in vacuo leaving a pale yellow oil (154 g.).

The pale yellow oil is added to a solution of sodium methoxide (29.72 g., 0.55 mole) in methanol (500 ml.) and allowed to stand at 25° for 48 hours. After concentrating the reaction mixture in vacuo, the residual mass is partitioned between ether and water; the aqueous phase is acidified with 10% sulfuric acid. The organic extract is washed with water until the washings are neutral, dried over magnesium sulfate and distilled; the fraction with b.p. 137°–155°/0.2–0.3 mm. is redistilled to yield the title compound as a colorless liquid (64.5 g., 53%), b.p. 150°–153°/0.2–0.3 mm.

Anal. Calcd. for $C_{12}H_{20}O_5$: C, 59.00; H, 8.25; Found: C, 58.98; H, 8.42

Step B(1): 1-Chloro-3-octanol

To the Grignard reagent prepared from a mixture of 1-bromopentane (66.50 g., 0.44 mole) and magnesium (10.7 g., 0.44 mole) in ether (450 ml.) is added, dropwise with stirring during one hour, 3-chloropropanal (4.1 g., 0.44 mole) in ether (200 ml.) Stirring and refluxing are continued for an additional hour.

The reaction mixture is cooled and poured into a mixture of finely crushed ice (600 g.) and concentrated hydrochloric acid (225ml.). The ether layer is separated, washed well with water, and dried over anhydrous sodium sulfate. The solvent is removed by evaporation in vacuo and the residual oil distilled to give 36.0 g. (50%) of colorless liquid, b.p. 113°–114°/14 mm. Hg. pressure; pmr $(CDCl_3)$ δ0.88 (3H,t), 1.87 (2H,q), 2.18 (H,s), 3.67 (2H,t), and 3.76 (H,s).

Anal. Calcd. for $C_8H_{16}ClO$: Cl, 21.66; Found: Cl, 21.15

Step B(2): 3-Chloromethoxy-1-chlorooctane

A slow stream of hydrogen chloride gas is passed into a mixture of 1-chloro-3-octanol (35.5 g., 0.218 mole) and s-trioxane (6.55 g., 0.073 mole) in a conical flask cooled to 0° C. and protected from atmospheric moisture. The process requires about 3½ hours. The resulting two-phase mixture is treated with anhydrous calcium chloride at 25° C. for 64 hours. The upper aqueous phase is removed by this action. The solid material is removed by filtration and the filtrate distilled to give the 3-chloromethoxy-1-chlorooctane as a colorless liquid (28.2 g., 61%), b.p. 128°–130°/15 mm.; pmr $(CDCl_3)$δ0.88 (3H,t), 1.98 (2H,q), 3.61 (2H,t), 3.92 (H,m), and 5.51 (2H,s).

Anal. Calcd. for $C_9H_{18}Cl_2O$: C, 50.72; H, 8.51; Cl, 33.26; Found: C, 50.27; H, 8.58; Cl, 33.48

Step B(3): Preparation of 3-Benzyloxy-1-chlorooctane

To the Grignard reagent prepared from bromobenzene (46.5 g., 0.296 mole) and magnesium (7.2 g., 0.296 mole) in ether (150 ml.) is added, dropwise with stirring, 3-chloromethoxy-1-chlorooctane (63.0 g., 0.296 mole) in ether (100 ml.). The resulting solution is stirred at 25° C. for 16 hours, then refluxed for 1¼ hours, cooled to 0° and cautiously treated with ice water (200 ml.) with vigorous stirring. After separating the phases, the aqueous layer is extracted with ether (200 ml.) The combined organic phases are washed with water, then 5% aqueous potassium carbonate and finally with saturated aqueous sodium chloride solution.

The organic phase is dried over sodium sulfate and evaporated in vacuo leaving the crude product which is distilled in vacuo to give pure 3-benzyloxy-1-chlorooctane, (61.4 g., 81% yield), b.p. 127° at 0.2 mm. Hg. pressure; pmr $(CDCl_3)$δ0.88 (3H,t), 1.92 (2H,q), 3.61 (2H,t; H,b), 4.50 (2H,s) and 7.29 (5H,s).

Anal. Calcd. for $C_{15}H_{23}ClO$: C, 70.71; H, 9.10; Found: C, 70.91; H, 9.25

Step B(4): Preparation of Methyl 8-Oxo-9-methoxycarbonyl-12-benzyloxyheptadecanoate This compound is prepared essentially by the same procedure as described in Example 1, Step B(4), (except sodium iodide is used as an alkylation catalyst and the reaction period is extended to 44–45 hours,) employing the following reagents:

The title compound is obtained as a pale yellow oil (46.0 g., 100%); pmr $(CDCl_3)$δ0.88 (3H,t), 3.55 (8H, 25 and m), 4.50 (2H,s) and 7.29 (3H,s).

Step C: Preparation of 8-Oxo-12-benzyloxyheptadecanoic Acid

A dispersion of methyl 8-oxo-9-carbomethoxy-12-benzyloxyheptadecanoate (46.0 g., 0.1 mole) and potassium hydroxide (12.9 g., 23.0 mole) in water (150 ml.) is maintained at 5° for 41 hours. To the resulting mixture is added 2N hydrochloric acid (200 ml.) over one hour at 0°. The mixture is stored at 5° for one week, then diluted with water (150 ml.) and extracted with ether (2 × 300 ml.).

The organic extract is washed with saturated brine, dried over sodium sulfate and evaporated in vacuo leaving a semi-solid residue which is suspended in chloroform (50 ml.). The insoluble solid is collected, washed with chloroform (2 × 25 ml.) and dried at 65° for 2 hours to provide 3-oxosebacic acid (2.5 g.), 110°–111°.

The combined organic filtrate and washings is evaporated in vacuo to a yellow oil (42 g.) which is treated with a solution of potassium hydroxide (16.8 g., 0.3 mole) in methanol (300 ml.). The resulting solution is stirred at 25° for 17 hours and filtered to remove a trace of insoluble material. The filtrate is evaporated in vacuo to a yellow residue which is suspended in water (200 ml.). The resulting suspension is cooled to 0°, vigorously stirred and treated with concentrated HCl (30 ml.) added dropwise over 10 min. which initiates smooth decarboxylation. The mixture is stirred at ambient temperature for ¼ hour, diluted with water (600 ml.) and extracted with ether (3 × 200 ml.). The organic extract is washed with saturated brine, dried over sodium sulfate and evaporated in vacuo to a pale yellow oil which is applied to a silica gel column (500 g.) with chloroform. Elution with chloroform (2.175 l.) provides impure material; continued elution with the same eluant (3.1 l.) gives the title compound as a colorless oil (12.3 g., 32%); pmr $(CDCl_3)$δ0.88 (3H,t), 4.50 (2H,s), 7.29 (5H,s) acid 7.89 (H, b.s.).

Anal. Calcd. for $C_{29}H_{38}O_4$: C, 73.80; H, 9.80; Found: C, 73.13; H, 10.00

Step D(1): Preparation of 3-Chloromethoxy-1-bromopropane

A slow stream of dry hydrogen chloride (g) is passed into a mixture of 3-bromo-1-propanol (83.4 g., 0.6 mole) and s-trioxane (18.0 g., 0.2 mole) contained in a conical flask cooled at 0° for 3½ hours. The resulting two-phase mixture is dried over calcium chloride (upper, aqueous phase is consumed by the drying agent) at 25° for 64 hours., filtered and distilled to give the title compound (55.2 g., 50%) as a colorless liquid, b.p. 78°–80°/15 mm.; pmr $(CDCl_3)$δ2.15 (2H,p), 3.49 (2H,t), 3.82 (2H,t), and 5.49 (2H,s).

Anal. Calcd. for $C_4H_8BrClO$: C, 25.63; H, 4.30; Found: C, 25.85; H, 4.36

Step D(2): Preparation of 3-Benzyloxy-1-bromopropane

To the Grignard reagent prepared from bromobenzene (46.3 g., 0.294 mole) and magnesium (7.15 g., 0.294 mole) in ether (150 ml.) is added, dropwise over one hour at 0°, a solution of 3-chloromethoxy-1-bromopropane (55.0 g., 0.294 mole) in ether (50 ml.). The resulting solution is stirred at 25° for 16 hours, then heated at reflux for ¼ hour, cooled to 0° and cautiously treated with ice water (200 ml.) with vigorous stirring. After separating the phases, the aqueous layer is extracted with ether (200 ml.). The combined organic extract is washed with water, 5% potassium carbonate, water and saturated brine, dried over sodium sulfate and evaporated in vacuo leaving a pale yellow oil (64.4 g., 96%) which is distilled to provide the title compound as a colorless liquid (92% recovery), b.p. 140°–141°/14 mm.; pmr (CDCl$_3$)$\delta$2.12 (2H,p), 3.51 (2H,t), 3.60 (2H,t), 4.50 (2H,t) and 7.31 (5H,s).

Anal. Calcd. for $C_{10}H_{13}BrO$: Br, 34.88 Found: Br, 35.26

Step D(3): Preparation of 3-Benzyloxypropyltriphenylphosphonium Bromide

A solution of 3-benzyloxy-1-bromopropane (41.0 g., 0.18 mole) and triphenylphosphine (52.4 g., 0.2 mole) in benzene (500 ml.) is stirred and heated at reflux for 92 hours. After removing the solvent in vacuo, the residual gum is dissolved in acetonitrile (50 ml.) providing a pale yellow solution which is diluted with ethyl acetate (400 ml.) to incipient cloudiness and stirred at 25° for 48 hours. Deposited crystals are collected; the yield is 48 g. (53%). Recrystallization from ethyl acetate-acetonitrile (4:1) provides colorless needles, m.p. 151°–152°; pmr (CDCl$_3$)$\delta$2.0 (2H,m), 3.78 (4H,m), 4.49 (2H,s), 7.29 (5H,s) and 7.70 (15H,m).

Anal. Calcd. for $C_{25}H_{28}BrOP$: C, 68.44; H, 5.74; Found: C, 68.28; H, 5.83

Step D(4): Preparation of 8-(3-Benzyloxypropylidenyl)-12benzyloxyheptadecanoic Acid A suspension of 57% sodium hydride in mineral oil (1.68 g., 40 millimoles) and 3-benzyloxypropyltriphenylphosphonium bromide (9.83 g., 20 millimole) in hexamethylphosphoric triamide (HMPT) (60 ml.) is stirred at 25° C. for 30 minutes. The resulting yellow suspension is vigorously stirred and cautiously treated with a solution of 8-oxo-12-benzyloxyheptadecanoic acid (7.81 g., 20 millimole) in HMPT (40 ml.) over a period of 40 minutes at 25° C. The temperature for another hour, then slowly warmed to 100° and then kept at 100° for 64 hours.

After cooling to 0°, the reaction mixture is partioned between ice water (2 liters) containing concentrated hydrochloric acid (6 ml.) and ether (3 × 400 ml.). The combined organic extracts are washed with water and then saturated brine. After drying over anhydrous sodium sulfate, the extract is evaporated in vacuo to give a liquid residue (13.8 g.) which is applied to a silica gel column (250 g. 0.05–0.2 mesh, E. Merck material) with chloroform. After eluting with chloroform (1825 ml.) the 8-(3-benzyloxypropylidenyl)-12-benzyloxyheptadecanoic acid is obtained as a colorless liquid (2.5 g., 23% yield); pmr (CDCl$_3$)$\delta$0.88 (3H,t), 3.47 (2H,t: H bs.), 4.50 (2H,s), 5.15 (H,t) and 7.29 (5H,s).

Step E: Preparation of 8-(4-Benzyloxy-1-nonyl)-8,9-oxido-11-benzyloxyundecanoic Acid A solution of m-chloroperbenzoic acid (0.98 g., 4.84 millimole) in methylene chloride (12 ml.) is added over 5 minutes to a solution of 8-(3-benzyloxypropylidenyl)-12-benzyloxyheptadecanoic acid (2.3 g., 4.4 millimoles) in methylene chloride (8 ml.). After stirring at 15° C. for 4 hours, the resulting suspension is cooled to −15° C. and filtered. The filtrate is diluted with methylene chloride (40 ml.), washed with 10% aqueous sodium sulfate, water, saturated aqueous sodium chloride and then dried over anhydrous sodium sulfate for 15 hours at 25° C. The solution is filtered and the filtrate is removed by evaporation in vacuo, leaving the 8-(4-benzyloxy-1-nonyl)-8,9-oxido-11-benzyloxyundecanoic acid as a colorless liquid in quantitative yield; pmr (CDCl$_3$) $\delta$2.86 (H,t).

Step F: Preparation of 8-(3-Benzyloxypropionyl)-12-benzyloxyheptadecanoic Acid Boron trifluoride etherate (5.6 ml., 44 millimole) is added to a solution of 8-(4-benzyloxy-1-nonyl)-8,9-oxido-11-benzyloxyheptadecanoic acid (2.37 g., 4.4 millimole) in ether (40 ml.) at 0° C. After stirring at 0° C. for 45 minutes, the resulting solution is partitioned between ether (160 ml.) and saturated aqueous ammonium chloride (3 × 40 ml.). The organic extract is dried over anhydrous sodium sulfate, filtered and evaporated in vacuo to give 8-(3-benzyloxypropionyl)-12-benzyloxyheptadecanoic acid (2.37 g., 100% yield); pmr (CDCl$_3$)$\delta$2.67 (2H,t, J=6 cps.) and 3.73 (2H,t, J=6 cps.).

Step G: Preparation of 8-(3-Hydroxypropionyl)-12-hydroxyheptadecanoic Acid . ⅓ Chloroformate A magnetically stirred solution of 8-(3-benzyloxypropionyl)-12-benzyloxyheptadecanoic acid (2.37 g., 4.4 millimole) in ethanol (50 ml.) is subjected to hydrogenation at atmospheric pressure at 23° C. in the presence of a 10% palladium on charcoal catalyst (0.3 g.) for one hour. The hydrogen uptake is 2.4 ml. (100% theory). The catalyst is removed by filtration and the solvent is removed by evaporation in vacuo to give 8-(3-hydroxypropionyl)-12-hydroxyheptadecanoic acid . 1/3 chloroformate as a viscous, colorless liquid (1.55 g., 97% yield); pmr (CDCl$_3$) $\delta$0.88 (3H,t), 2.03 (H,m), 2.32 (2H,t), 2.68 (2H,t, J=5.5 cps.), 3.65 (H, b.s.), 3.86 (2H,t, J=5.5 cps.), 5.50 (3H, exchangeable s) and 7.32 (1/3H,s).

Anal. Calcd. for $C_{20}H_{38}O_5$·1/3CHCl$_3$: C, 61.29; H, 9.70; Found: C, 61.21; H, 9.48 C, 61.02; H, 9.69

EXAMPLE 9

Preparation of 8-(1-hydroxyethyl)-12-hydroxyheptadecanoic Acid

Sodium borohydride (57% in mineral oil) (0.76 g., 0.02 mole) is dissolved in a solution of 8-acetyl-12-hydroxyheptadecanoic acid (Example 1) (7.2 g., 0.022 mole) and sodium hydroxide (1.2 g., 0.03 mole) in water (80 ml.). The resulting solution is allowed to stand at room temperature for 23 hours, and is then acidified to Congo Red with concentrated hydrochloric acid. The oily product is taken up in ether, washed with water, and dried over sodium sulfate. The ether is evaporated leaving 6.5 g. (90%) of 8-(1-hydroxyethyl)-12-hydroxyheptadecanoic acid as a yellow oil.

The product is purified by chromatograpy on a column containing 120 g. of silica gel made up with chloroform. The column is eluted with 2% methanol in chloroform and finally with 4% methanol in chloroform. Fractions are pooled and evaporated to yield a fraction with Rf 0.17 on silica gel thin layer plates with an eluant of chloroform-methanol-acetic acid (97:2:1) (iodine vapor development). The purified product, a nearly colorless oil, weighs 4.1 g. (57%).

Anal. Calcd. for $C_{19}H_{38}O_4$: C, 69.04; H, 11.59 Found: C, 68.74; H, 12.03 pmr (CDCl$_3$) δ 0.88 (3H, t), 1.13 (3H, d, $\underline{CH_3}$CHOH), 2.30 (2H, t, $\underline{CH_2}$COOH), 3.70 (2H,m, $\underline{H}$COH), 5.56 (3H, s, OH and COOH).

EXAMPLE 10

Preparation of
8-Hydroxymethyl-12-hydroxyheptadecanoic Acid

Step A: Ethyl 8-Hydroxymethyl-12-acetoxyheptadecanoate

Ethyl 8-chlorocarbonyl-12-acetoxyheptadecanoate (Example 7, Step D) (14.0 g., 0.0335 mole) is added all at once to a solution of sodium borohydride (2.7 g., 0.07 mole) in dry diglyme (75 ml.). An exothermic reaction occurs with foaming and a rise in temperature to 55°. After 2 hours, the reaction mixture is cooled in an ice bath and 10% hydrochloric acid is added dropwise until the mixture is acidic to Congo Red. Water (250 ml.) is then added; the oily product is extracted into ether, washed with after, and dried over sodium sulfate. The ether is evaporated to leave 12.2 g. of 8-hydroxymethyl-12-acetoxyheptadecanoate as a yellow oil. The product is used in the next step without further purification.

Step B: 8-Hydroxymethyl-12-hydroxyheptadecanoic Acid

Ethyl 8-hydroxymethyl-12-acetoxyheptadecanoate (12.2 g., 0.0316 mole) is dissolved in a solution of sodium hydroxide (4.0 g., 0.10 mole) in water (20 ml.) and methanol (100 ml.), and the resulting solution is allowed to stand 64 hours at 25°. The methanol is then evaporated at reduced pressure, and the residual solution is diluted with water (150 ml.) and extracted with ether. The aqueous solution is acidified to Congo Red with concentrated hydrochloric acid. The oily acid which separates is taken up in ether, washed with water, and dried over sodium sulfate. The ether is evaporated to leave 6.6 g. of 8-hydroxymethyl-12-hydroxyheptadecanoic acid as a yellow oil.

The product is purified by column chromatography on silica gel (110 g.) with elution first with 2% methanol in chloroform followed by 4% methanol in chloroform. There is obtained 3.7 g. of 8-hydroxymethyl-12-hydroxyheptadecanoic acid as a colorless oil showing a single spot, Rf 0.14, on silica gel thin layer chromatography with chloroform-methanol-acetic acid, 96:3:1, elution.

pmr (CDCl$_3$) δ0.90 (3H,t), 2.32 (2H,t, $\underline{CH_2}$COOH), 3.55 (3H,m, $\underline{CHOH}$ and $\underline{CH_2}$OH), 5.1 (3H,m, OH and COOH).

Anal. Calcd. for $C_{18}H_{36}O_4$: C, 68.31; H, 11.47; Found: C, 68.72; H, 11.53

EXAMPLE 11

Preparation of
8-Acetyl-12-hydroxy-16-methylheptadecanoic Acid

Step A: Preparation of 1-Chloro-8-methyl-4-nonanone

To the Grignard reagent prepared from a mixture of 1-bromo-4-methylpentane (200.00 g.; 1.21 mole) and magnesium (29.43 g.; 1.21 mole) in ether (800 ml.) is added, dropwise during one hour, 4-chlorobutyronitrile (125.30 g., 1.21 mole). Stirring is continued for an additional one hour.

The reaction mixture is poured into a mixture of finely crushed ice (800 g.) and concentrated hydrochloric acid (600 ml.). The ether layer is separated quickly and discarded. The aqueous layer is heated on a steam bath for one hour to hydrolyze the intermediate imine and cause the separation of the ketone as an oil. After cooling, the oil is extracted with ether and the combined extracts are washed with saturated sodium chloride solution and dried over anhydrous sodium sulfate. The solvent is removed under vacuum and the residual oil is distilled to give 23.3 g. (10%) of colorless oil, b.p. 121°-122°/15 mm.; pmr (CDCl$_3$) δ0.89 (6H,d), 3.57 (2H,t CH$_2$Cl).

Anal. Calcd. for $C_{10}H_{19}ClO$: C, 62.98; H, 10.04; Found: C, 62.86; H, 10.20

Step B: Preparation of 1-Chloro-8-methyl-4-nonanol

A suspension of sodium borohydride (2.31 g.; 0.061 mole) and sodium hydroxide (0.5 g.) in ethanol (110 ml.) is treated dropwise, over one hour, with 1-chloro-8-methyl-4-nonanone (23.0 g., 0.121 mole) while the temperature is maintained at 45-50. Stirring is continued for one hour longer without external cooling.

The reaction mixture is acidified with concentrated hydrochloric acid to the Congo Red endpoint and then the ethanol is removed under reduced pressure. The residue is treated with water (70 ml.) and the resulting oil is extracted with ether. The combined extracts are washed with saturated sodium chloride solution and dried over anhydrous sodium sulfate. The solvent is removed under vacuum to give the title compound as a light yellow residual oil, yield 22.73 g.; ir (neat) 3400 cm$^{-1}$.

Step C: Preparation of 1-Chloro-4-acetoxy-8-methylnonane

A mixture of 1-chloro-8-methyl-4-nonanol (22.73 g.; 0.118 mole) and acetic anhydride (24.07 g.; 0.236 mole) is heated on a steam bath for 1½ hours.

The volatile materials are removed under reduced pressure and the residual oil is distilled to give 14.58 g. (58%) of colorless oil, b.p. 138°-139°/15 mm.; pmr (CDCl$_3$) δ0.85 (6H,d), 2.02 (3H,s CH$_3$COO), 3.53 (2H, t CH$_2$Cl), 4.92 (1H,m).

Step D: Preparation of Ethyl 8-Acetyl-8-tert.-butoxycarbonyl-12-acetoxy-16-methylheptadecanoate This compound is prepared essentially by the same procedure as described in Example 1, Step B(4) (except a trace of potassium iodide is added just prior to heating and the heating period at 100° is continued for 69 hours), using the following reagents:

| | |
|---|---|
| Sodium hydride (57% in mineral oil) | 2.56 net wt. (0.0607 mole) |
| Benzene | 30 ml. |
| Dimethylformamide | 30 ml. |
| Ethyl 8-tert.-butoxycarbonyl-9-oxodecanoate | 17.36 g. (0.0552 mole) (Example 1, Step A) |
| 1-Chloro-4-acetoxy-8-methylnonane | 14.21 g. (0.0607 mole) |
| Potassium iodide | Trace |

The title compound is obtained as a residual oil, yield 28.30 g.; pmr (CDCl$_3$) δ0.87 (6H,d), 1.45 (9H,s), 2.01 (3H,s CH$_3$COO), 2.10 (3H,s CH$_3$CO), 4.15 (2H,q).

Step E: Preparation of Ethyl 8-Acetyl-12-acetoxy-16-methylheptadecanoate

This compound is prepared essentially by the same procedure as described in Example 1, Step C (except reflux time is 19 hours), using the following reagents:

| | |
|---|---|
| Ethyl 8-acetyl-8-tert.-butoxycarbonyl-12-acetoxy-16-methylheptadecanoate | 28.30 g. (0.0552 mole) |
| p-Toluenesulfonic acid monohydrate | 1.00 g. |
| Toluene | 100 ml. |

The title compound is obtained as a residual oil, yield 22.78 g. The oil is purified by column chromatography on silica gel with chloroform as an eluant, pmr (CDCl$_3$) $\delta$0.83 (6H,d), 2.02 (3H,s CH$_3$COO), 2.10 (3Hs, CH$_3$CO), 4.07 (2H,q).

Anal. Calcd. for C$_{24}$H$_{44}$O$_5$: C, 69.86; H, 10.75; Found: C, 70.00; H, 10.97

Step F: Preparation of 8-Acetyl-12-hydroxy-16-methylheptadecanoic acid

This compound is prepared essentially by the same procedure as described in Example 1, Step D (except reaction solution is allowed to stand at 60° for 16-½ hours), using the following reagents:

| | |
|---|---|
| Ethyl 8-acetyl-12-acetoxy-16-methylheptadecanoate | 11.2 g. (0.0272 mole) |
| Sodium hydroxide | 3.2 g. (0.080 mole) |
| Water | 20 ml. |
| Methanol | 150 ml. |

The title compound is obtained as a residual oil, yield 8.4 g. The oil is purified by column chromatography on silica gel with 2% methanol in chloroform as an eluant, pmr (CDCl$_3$) $\delta$0.88 (6H,d), 2.12 (3H,s CH$_3$CO), 3.62 (1H,m HCOH), 7.55 (2H,s OH, COOH).

Anal. Calcd. for C$_{20}$H$_{38}$O$_4$: C, 70.13; H, 11.18; Found: C, 70.01; H, 11.08

EXAMPLE 12

Preparation of 8-Acetyl-12-hydroxynonadecanoic acid

Step A: Preparation of 1-Chloro-4-undecanone

This compound is prepared essentially by the same procedure as described in Example 1, Step B(1), using the following reagents:

| | |
|---|---|
| 1-Bromoheptane | 214.94 g. (1.2 mole) |
| Magnesium | 29.18 g. (1.2 mole) |
| Ether | 800 ml. |
| 4-Chlorobutyronitrile | 124.27 g. (1.2 mole) |

The title compound is obtained as a colorless oil, yield 60.4 g. (15%), b.p. 135°–140°/15 mm.; pmr (CDCl$_3$) $\delta$0.93, (3H,t), 3.57 (2H,t CH$_2$Cl).

Step B: Preparation of 1-Chloro-4-undecanol

This compound is prepared essentially by the same procedure as described in Example 1, Step B(2), using the following reagents:

| | |
|---|---|
| Sodium borohydride | 5.56 g. (0.147 mole) |
| Sodium hydroxide | 1.12 g. |
| Ethanol | 265 ml. |
| 1-Chloro-4-undecanone | 60.00 g. (0.294 mole) |

The title compound is obtained as a yellow residual oil, yield 60.02 g.

Step C: Preparation of 1-Chloro-4-acetoxyundecane

This compound is prepared essentially by the same procedure as described in Example 1, Step B(3), using the following reagents:

| | |
|---|---|
| 1-Chloro-4-undecanol | 60.02 g. (0.29 mole) |
| Acetic anhydride | 59.16 g. (0.58 mole) |

The title compound is obtained as a colorless oil, yield 44.6 g. (62%), b.p. 155°–158°/15 mm.; pmr (CDCl$_3$) $\delta$0.88 (3H,t), 2.02 (3H,s CH$_3$COO), 3.53 (2H,t CH$_2$Cl), 4.92 (1H,m).

Anal. Calcd. for C$_{13}$H$_{25}$ClO$_2$: C, 62.76, H, 10.13; Found: C, 63.03; H, 10.40

Step D: Preparation of Ethyl 8-Acetyl-8-tert.-butoxycarbonyl-12-acetoxynonadecanoate This compound is prepared essentially by the same procedure as described in Example 1, Step B(4), (except a trace of potassium iodide is added just prior to heating and then the heating period at 100° is continued for 69 hours), using the following reagents:

| | |
|---|---|
| Sodium hydride (57% in mineral oil) | 3.47 net wt. (0.0825 mole) |
| Benzene | 38 ml. |
| Dimethylformamide | 38 ml. |
| Ethyl 8-Tert.-Butoxycarbonyl-9-oxodecanoate | 23.58 g. (0.075 mole) (Example 1, Step A) |
| 1-Chloro-4-acetoxyundecane | 20.53 g. (0.0825 mole) |
| Potassium iodide | Trace |

The title compound is obtained as a residual oil, yield 39.52 g.; pmr (CDCl$_3$) $\delta$0.88 (3H,t), 1.45 (9H,s), 2.02 (3H,s CH$_3$COO), 2.11 (3H,s CH$_3$CO), 4.13 (2H,q).

Step E: Preparation of Ethyl 8-Acetyl-12-acetoxynonadecanoate

This compound is prepared essentially by the same procedure as described in Example 1, Step C (except reflux time is 22 hours), using the following reagents:

| | |
|---|---|
| Ethyl 8-acetyl-8-tert.-butoxycarbonyl-12-acetoxynonadecanoate | 39.52 g. (0.075 mole) |
| p-Toluenesulfonic acid monohydrate | 1.35 g. |
| Toluene | 135 ml. |

The title compound is obtained as a residual oil, yield 30.1 g. The oil is purified by column chromatography on silica gel with chloroform as an eluant, pmr (CDCl$_3$) $\delta$ 0.88 (3H,t), 2.02 (3H,s CH$_3$COO), 2.10 (3H,s CH$_3$CO), 4.13 (2H,q).

Anal. Calcd. for C$_{25}$H$_{46}$O$_5$: C, 70.38; H, 10.87; Found: C, 70.17; H, 11.04

Step F: Preparation of 8-Acetyl-12-hydroxynonadecanoic acid

This compound is prepared essentially by the same procedure as described in Example 1, Step D (except reaction solution is allowed to stand at 60° for 16 hours), using the following reagents:

| | |
|---|---|
| Ethyl 8-acetyl-12-acetoxy-nonadecanoate | 14.00 g. (0.0329 mole) |
| Sodium hydroxide | 3.95 g. (0.0987 mole) |
| Water | 18.5 ml. |
| Methanol | 166.5 ml. |

The title compound is obtained as a residual oil, yield 10.57 g. The oil is purified by column chromatography on silica gel with 2% methanol in chloroform as an eluant, pmr (CDCl$_3$) δ 0.90 (3H,t), 2.11 (3H,s CH$_3$CO), 7.13 (2H,s OH, COOH).

Anal. Calcd. for C$_{21}$H$_{40}$O$_4$: C, 70.74; H, 11.31; Found: C, 71.01; H, 11.34

EXAMPLE 13

Preparation of 2-Methyl-8-acetyl-12-hydroxyheptadecanoic accid

Step A: 5-Acetoxypentyl chloride

Acetic anhydride (102 g., 1 mole) is added dropwise with stirring to pentamethylene chlorohydrin (90 g., 0.74 mole). The resulting solution is heated on the steam bath for one hour and allowed to stand overnight at room temperature. The reaction mixture is distilled to yield 83.6 g. (69%) of 5-acetoxypentyl chloride, b.p. 101°–104°/20 mm.

Step B: Diethyl (5-Acetoxypentyl)methylmalonate

Sodium hydride (4.8 g., 0.2 mole) as a 50% suspension in mineral oil is washed with petroleum ether under nitrogen to remove the mineral oil, suspended in dry benzene (150 ml.), and the suspension cooled in an ice bath. Diethyl methylmalonate (34.8 g., 0.2 mole) dissolved in sieve dried DMF (150 ml.) is added to the suspension of sodium hydride dropwise. The mixture is allowed to stand overnight at room temperature. Potassium iodide (0.4 g.) and 5-acetoxypentyl chloride (32.9 g., 0.2 mole) are then added, and the mixture is heated for 24 hours at 125° in an oil bath. The reaction mixture is concentrated in vacuo, diluted with ether (200 ml.), and filtered to remove sodium chloride. The filtrate is washed with brine, dried over anhydrous magnesium sulfate and concentrated to yield 39.6 g. (66%) of oily product.

Step C: 7-Bromo-2-methylheptanoic acid

A mixture of the crude diethyl (5-acetoxypentyl)methylmalonate (68 g. 0.23 mole) and 48% aqueous hydrobromic acid (100 ml.) is refluxed for 20 hours. The mixture is then concentrated by distillation until the internal temperature rises to 120° ; 96 ml. of distillate (2 layers) is collected. The residual liquid is cooled, dissolved in ether, washed with brine, dried over magnesium sulfate, and the solution concentrated in vacuo to yield 54 g. of crude 7-bromo-2-methylheptanoic acid as a dark viscous liquid.

Step D: Methyl 7-Bromo-2-methylheptanoate

A solution of crude 7-bromo-2-methylheptanoic acid (54 g., 0.24 mole) and concentrated sulfuric acid (2 drops) in absolute methanol (300 ml.) is refluxed for 5 hours. After standing overnight at room temperature, the solution is concentrated in vacuo and diluted with water. The mixture is made basic by the addition of saturated sodium carbonate solution and the product taken up in ether. The ether extract is washed with water, dried over anhydrous magnesium sulfate and distilled to yield 11.8 g. (16%) of methyl 7-bromo-2-methylheptanoate, b.p. 67°–70°/0.05 mm.; pmr (CDCl$_3$) δ1.13 (3H,d 2-CH$_3$), 2.42 (1H,m CHCOOCH$_3$), 3.38 (2H,t CH$_2$Br), 3.65 (3H,s CH$_3$O).

Step E: Preparation of Methyl 2-Methyl-8-tert.-butoxycarbonyl-9-oxodecanoate This compound is prepared essentially by the same procedure as described in Example 1, Step A (except the heating period at 100° is continued for 5-¾ hours), using the following reagents:

| | |
|---|---|
| Sodium hydride (57% in mineral oil) | 3.75 g. net wt. (0.089 mole) |
| Benzene | 40 ml. |
| Dimethylformamide | 40 ml. |
| Tert.-Butyl Acetoacetate | 12.81 g. (0.081 mole) |
| Methyl 7-Bromo-2-Methyl-heptanoate | 21.01 g. (0.089 mole) |

The title compound is obtained as a light yellow oil, yield 13.35 g. (52%), b.p. 168°–170°/0.05 mm.; pmr (CDCl$_3$) δ1.13 (3H,d 2-CH$_3$), 1.45 (9H,s), 2.20 (3H,s CH$_3$CO), 3.27 (1H,t), 3.67 (3H,s CH$_3$O).

Step F: Preparation of Methyl 2-Methyl-8-acetyl-8-tert.-butoxycarbonyl-12-acetoxyheptadecanoate This compound is prepared essentially by the same procedure as described in Example 1, Step B(4) (except a trace of potassium iodide is added just prior to heating and the heating period at 100° is continued for 65 hours), using the following reagents:

| | |
|---|---|
| Sodium hydride (57% in mineral oil) | 1.90 g. net wt. (0.0453 mole) |
| Benzene | 25 ml. |
| Dimethylformamide | 25 ml. |
| Methyl 2-methyl-8-tert.-butoxycarbonyl-9-oxodecanoate | 12.95 g. (0.0412 mole) |
| 1-Chloro-4-acetoxynonane (Example 1, Step B(3)) | 10.00 g. (0.0453 mole) |
| Potassium iodide | Trace |

The title compound is obtained as a residual oil, yield 20.55 g.; pmr (CDCl$_3$) δ1.13 (3H,d 2-CH$_3$), 1.45 (9H,s), 2.02 (3H,s CH$_3$COO), 2.12 (3H,S CH$_{23}$CO), 3.67 (3H,s CH$_3$O).

Step G: Preparation of Methyl-2-Methyl-8-acetyl-12-acetoxyheptadecanoate

This compound is prepared essentially by the same procedure as described in Example 1, Step C (except reflux time is 22 hours), using the following reagents:

| | |
|---|---|
| Methyl 2-methyl-8-acetyl-8-tert.-butoxycarbonyl-12-acetoxyheptadecanoate | 20.55 g. (0.0412 mole) |
| p-Toluenesulfonic acid monohydrate | 700 mg. |
| Toluene | 70 ml. |

The title compound is obtained as a residual oil, yield 16.42 g. The oil is purified by column chromatography on silica gel with chloroform as an eluant, pmr (CDCl$_3$) δ 1.13 (3H,d 2-CH$_3$), 2.02 (3H,s CH$_3$COO), 2.10 (3H,s CH$_3$CO), 3.67 (3H,s CH$_3$O), 4.82 (1H,m HCOCOCH$_3$).

Anal. Calcd. for C$_{23}$H$_{42}$O$_5$: C, 69.31; H, 10.62; Found: C, 69.32; H, 10.53

Step H: Preparation of 2-Methyl-8-acetyl-12-hydroxyheptadecanoic acid

This compound is prepared essentially by the same procedure as described in Example 1, Step D (except reaction solution is allowed to stand at 25° for 70 hours), using the following reagents:

| | |
|---|---|
| Methyl 2-Methyl-8-Acetyl-12-acetoxyheptadecanoate | 11.0 g. (0.0277 mole) |
| Sodium hydroxide | 3.4 g. (0.085 mole) |
| Water | 35 ml. |
| Methanol | 200 ml. |

The title compound is obtained as a residual oil, yield 7.5 g. The oil is purified by column chromatography on silica gel with 2% methanol in chloroform as an eluant, pmr (CDCl$_3$), δ 0.88 (3H,t), 1.17 (3H,d 2-CH$_3$), 2.12 (3H,s CH$_3$CO), 3.60 (1H,m HCOH), 6.77 (2H,s OH, COOH).

Anal. Calcd. for C$_{20}$H$_{38}$O$_4$: C, 70.13; H, 11.18; Found: C, 70.17; H, 11.06

EXAMPLE 14

Preparation of 8-(1,3-Dihydroxypropyl)-12-hydroxyheptadecanoic acid

Step A: Preparation of 8-(3-Benzyloxy-1-hydroxy-1-propyl)-12-benzyloxyheptadecanoic Acid A clear, yellow solution of 8-(3-benzyloxypropionyl)-12-benzyloxyheptadecanoic acid (2.55 g., 4.73 millimole) (Example 8, Step F) and potassium hydroxide (0.3 g., 5.2 millimole) in 90% aqueous methanol (20 ml.) is treated with potassium borohydride (0.26 g., 4.73 millimole) providing a clear, pale yellow solution which is stirred at 25° for 24 hours under nitrogen.

The reaction solution is heated at reflux for 2 hours and evaporated in vacuo at 40° leaving a pale yellow oil which is treated with water (100 ml.). The resulting turbid solution is cooled to 5°, acifified cautiously (excess hydride is present) with concentrated HCl (5 ml.), stirred at ambient temperature for 15 minutes and extracted with ether (200 ml.). The organic extract is washed with saturated aqueous brine (2 × 100 ml.) dried over sodium sulfate, filtered and evaporated in vacuo at 40° providing a crude oil (2.35 g., 92.3%); pmr (CDCl$_3$) δ0.88 (3H,t), 2.28 (2H,t), 3.28-3.92 (4H,m), 4.50, 4.63 (4H, 2s), 5.13 (2H, bs) and 7.32 (10H,s).

A sample of the oil (2.25 g.) is applied to a silica gel column (30 g., 0.05-0.2 mm., E. Merck, Darmstadt) with chloroform. Non-polar impurities (trace) are eluted with chloroform (85 ml.). Continued elution with the same eluant (20 ml.) provides oil A (0.5 g.). Further elution with the same eluant (125 ml.) followed by chloroform-methanol (95:5, 25 ml.) yields oil B (0.8 g.). Continued elution with the latter eluant (125 ml.) gives oil C (1.04 g.). Pmr (CDCl$_3$) and tlc evaluation of oils A, B, and C indicate that they are essentially pure 8-(3-benzyloxy-1-hydroxy-1-propyl)-12-benzyloxyheptadecanoic acid contaminated with only small amounts of impurities and this material is adequate for use in the next step.

Step B: Preparation of 8-(1,3-Dihydroxypropyl)-12-hydroxyheptadecanoic acid

This compound is prepared essentially by the same procedure as described in Example 8, Step G, employing the following reagents:

| | |
|---|---|
| 8-(3-Benzyloxy-1-Hydroxy-1-propyl)-12-benzyloxy-heptadecanoic acid, Oils A, B, and C described in Step A | 2.2 g., 4.1 mmole |
| 10% Palladium on Carbon | 230 mg. |
| Hydrogen (g) (uptake) | 210.3 ml. |
| Ethanol | 34 ml. |

The crude reduction mixture (1.55 g.) is applied to a silica gel column (30 g., 0.05-0.2 mm.; E. Merck, Darmstadt) with chloroform. Impurities are eluted with chloroform (260 ml.) followed by chloroform-methanol (98:2, 145 ml.) and chloroform-methanol (95:5, 60 ml.). Continued elution with the latter eluant (225 ml.) provides oil A (0.5 g.) which is a mixture of 8-(3-methoxy-1-hydroxy-1-propyl)-12-hydroxyheptadecanoic acid and 8,12-dihydroxyheptadecanoic acid.

Elution with chloroform-methanol (95:5, 125ml.) followed by chloroform-methanol (9:1, 700 ml.) provides the crude title compound as viscous oil B (0.21 g.). Oil B is purified via application to a preparative thin layer plate (silica gel GF, 2,000 microns, Analtech) with chloroform. The plate is eluted with chloroform-methanol-acetic acid (8:1:1), air-dried and the separated components, visualized with a u.v. lamp (u.v.s.-11, Mineral light). A band with RF=0.47-0.57 is removed and extracted with refluxing chloroform-methanol (9:1, 3 × 100 ml.). The combined organic extract is evaporated in vacuo at 40°-60° providing the pure title compound as a viscous, pale yellow oil (80 mg.); pmr (CDCl$_3$) δ0.90 (3H,t), 1.37 (27H,e), 2.31 (2H, bs), 3.80 (4H, bs) and 5.63 (4H, exchangeable, bs).

Anal. Calcd. for C$_{20}$H$_{40}$O$_5$: C, 66.62; H, 11.19; Found: C, 66.58; H, 11.29

EXAMPLE 15

Preparation of 9-Acetyl-12-hydroxyheptadecanoic Acid

Step A: Preparation of Ethyl 9-Tert.-butoxycarbonyl-10-oxoundecanoate

This compound is prepared essentially by the same procedure as described in Example 1, Step A (except a trace of potassium iodide is added just prior to heating and then the heating period at 100° is continued for 10 hours), using the following reagents:

| | |
|---|---|
| Sodium hydride (57% in mineral oil) | 17.85 g. net wt. (0.424 mole) |
| Benzene | 193 ml. |
| Dimethylformamide | 193 ml. |
| Tert.-Butyl acetoacetate | 60.19 g. (0.385 mole) |
| Ethyl 8-Bromooctanoate | 106.30 g. (0.424 mole) |
| Potassium iodide | Trace |

The title compound is obtained as a residual oil, yield 126.45 g; pmr (CDCl$_3$) δ1.47 (9H,s), 2.22 (3H,s CH$_3$CO), 3.33 (1H,t), 4.15 (2H,q).

Preparation of 1-Chloro-3-acetoxyoctane

Step 1: Preparation of 1-chloro-3-octanol

This compound is prepared essentially by the same procedure as described in Example 5, Step A(1), using the following reagents:

| 1-Bromopentane | 113.71 g. (0.753 mole) |
| Magnesium | 18.31 g. (0.753 mole) |
| Ether | 1100 ml. (total) |
| 3-Chloropropanol | 69.70 g. (0.753 mole) |

The title compound is obtained as a light yellow oil, yield 48.0 g. (39%), b.p. 110°–113°/14 mm.

Step B(2): Preparation of 1-Chloro-3-acetoxyoctane

This compound is prepared essentially by the same procedure as described in Example 1, Step B(3), using the following reagents:

| 1-Chloro-3-octanol | 48.00 g. (0.29 mole) |
| Acetic Anhydride | 59.16 g. (0.58 mole) |

The title compound is obtained as a colorless oil, yield 47.0 g. (78%), b.p. 118°–120°/14 mm.; pmr (CDCl$_3$) $\delta$0.90 (3H,t), 2.05 (3H,s CH$_3$COO), 3.59 (2H,t CH$_2$Cl), 5.07 (1H,m).

Anal. Calcd. for C$_{10}$H$_{19}$ClO$_2$: C, 58.10; H, 9.26; Found: C, 58.68; H, 9.45

Step B(3): Preparation of Ethyl 9-Acetyl-9-tert.-butoxycarbonyl-12-acetoxyheptadecanoate This compound is prepared essentially by the same procedure as described in Example 1, Step B(4) (except a trace of potassium iodide is added just prior to heating and then the heating period at 100° is continued for 67 hours), using the following reagents:

| Sodium hydride (57% in mineral oil) | 9.60 g net wt. (0.228 mole) |
| Benzene | 100 ml. |
| Dimethylformamide | 100 ml. |
| Ethyl 9-tert.-butoxycarbonyl-10-oxoundecanoate | 67.99 g. (0.207 mole) |
| 1-Chloro-3-acetoxyoctane | 47.00 g. (0.228 mole) |
| Potassium iodide | Trace |

The title compound is obtained as a residual oil, yield 97.1 g.; pmr (CDCl$_3$) $\delta$0.88 (3H,t), 1.45 (9H,s), 2.03 (3H,s CH$_3$COO), 2.12 (3H,s CH$_3$CO), 4.15 (2H,q).

Step C: Preparation of Ethyl 9-Acetyl-12-acetoxyheptadecanoate

This compound is prepared essentially by the same procedure as described in Example 1, Step C (except reflux time is 44 hours) using the following reagents:

| Ethyl 9-Acetyl-9-tert.-butoxycarbonyl-12-acetoxyheptadecanoate | 97.10 g. (0.195 mole) |
| p-Toluenesulfonic acid monohydrate | 3.40 g. |
| Toluene | 340 ml. |

The title compound is obtained as a residual oil, yield 77.44 g. The oil is purified by column chromatography on silica gel with chloroform as an eluant; pmr (CDCl$_3$) $\delta$0.88 (3H,t), 2.03 (3H,s CH$_3$COO), 2.12 (3H,s CH$_3$CO), 4.16 (2H,q).

Step D: Preparation of 9-Acetyl-12-hydroxyheptadecanoic Acid

Ethyl 9-acetyl-12-acetoxyheptadecanoate (13.5 g., 0.034 mole) is dissolved in a solution of sodium hydroxide (4.0 g., 0.10 mole) in water (40 ml.) and methanol (180 ml.). The resulting solution is heated at 60° for 20 hours. The methanol is then evaporated at reduced pressure. The residual solution is treated with 100 ml. water, extracted with ether, and the ether extract discarded. The aqueous solution is acidified with concentrated hydrochloric acid. The oily product which separates is taken up in ether, washed with water and dried over sodium sulfate. The ether is evaporated leaving 9.5 g. of product as a viscous light yellow oil.

The product is purified by chromatography on a column containing 250 g. silica gel made up in chloroform. The product is eluted with 2% methanol in chloroform. There is obtained 4.0 g. of pure 9-acetyl-12-hydroxyheptadecanoic acid exhibiting a single spot Rf 0.30 on silica gel thin layer plates with chloroformmethanol-acetic acid, 98:1:1 as eluant. The nmr spectrum indicates that this compound exists in equilibrium with its cyclic hemiketal.

Anal. Calcd. for C$_{19}$H$_{36}$O$_4$: C, 69.47; H, 11.05; Found: C, 60.93; H, 11.26

EXAMPLE 16

Preparation of 3-Methyl-8-acetyl-12-hydroxyheptadecanoic Acid

By replacing the ethyl 7-bromoheptanoate used in Example 1, Step A, with an equimolar quantity of methyl 3-methyl-7-iodoheptanoate then conducting the synthesis as described in Example 1, Steps A, B(4), C, and D, there is obtained in sequence methyl 3-methyl-8-tert.-butoxycarbonyl-9-oxodecanoate, methyl 3-methyl-8-acetyl-8-tert.-butoxycarbonyl-12-acetoxyheptadecanoate, methyl 3-methyl-8-acetyl-12-acetoxyheptadecanoate, and 3-methyl-8-acetyl-12-hydroxyheptadecanoic acid.

EXAMPLE 17

Preparation of 2,2-Dimethyl-8-acetyl-12-hydroxyheptadecanoic Acid

By replacing the ethyl 7-bromoheptanoate used in Example 1, Step A, with an equimolar quantity of methyl 2,2-dimethyl-7-iodoheptanoate then conducting the synthesis as described in Example 1, Steps A, B(4), C, and D, there is obtained in sequence methyl 2,2-dimethyl-8-tert.-butoxycarbonyl-9-oxodecanoate, methyl 2,2-dimethyl-8-acetyl-8-tert.-butoxycarbonyl-12-acetoxyheptadecanoate, methyl 2,2-dimethyl-8-acetyl-12-acetoxyheptadecanoate, and 2,2-dimethyl-8-acetyl-12-hydroxyheptadecanoic acid.

EXAMPLE 18

Preparation of 3,3-Dimethyl-8-acetyl-12-hydroxyheptadecanoic Acid

By replacing the ethyl 7-bromoheptanoate used in Example 1, Step A with an equimolar quantity of methyl 3,3-dimethyl-7-iodoheptanoate then conducting the synthesis as described in Example 1, Steps A, B(4), C, and D, there is obtained in sequence methyl 3,3-dimethyl-8-tert.-butoxycarbonyl-9-oxodecanoate, methyl 3,3-dimethyl-8-acetyl-8-tert.-butoxycarbonyl-12-acetoxyheptadecanoate, methyl 3,3-dimethyl-8-acetyl-12-acetoxyheptadecanoate, and 3,3-dimethyl-8-acetyl-12-hydroxyheptadecanoic acid.

EXAMPLE 19

Preparation of 8-Acetyl-12-hydroxy-16,16-dimethylheptadecanoic Acid

The synthesis of this compound was carried out as described in Example 1, except that in Step B(1), an equivalent amount of 1-bromo-4,4-dimethylpentane is substituted for the amyl bromide. Thus, there is obtained in order: ethyl 8-tert.-butoxycarbonyl-9-oxodecanoate (Step A), 1-chloro-8,8-dimethyl-4-nonanone (Step B(1)), 1-chloro-8,8-dimethyl-4-nonanol (Step B(2)), 1-chloro-8,8-dimethyl-4-acetoxynonane (Step B(3)), ethyl 8-acetyl-8-tert.-butoxycarbonyl-12-acetoxy-16,16-dimethylheptadecanoate (Step B(4)), ethyl 8-acetyl-12-acetoxy-16,16-dimethylheptadecanoate (Step C), and 8-acetyl-12-hydroxy-16,16-dimethylheptadecanoic acid.

EXAMPLE 20

Preparation of 8-Acetyl-12-hydroxy-17,17,17-trifluoroheptadecanoate

The synthesis of this compound was carried out as described in Example 1, except that in Step B(1), an equivalent amount of 1,1,1-trifluoro-5-bromopentane is substituted for the amyl bromide. Thus, there is obtained in order: ethyl 8-tert.-butoxycarbonyl-9-oxodecanoate (Step A), 1-chloro-9,9,9-trifluoro-4-nonanone (Step B(1)), 1-chloro-9,9,9-trifluoro-4-nonanol (Step B(2)), 1-chloro-9,9,9-trifluoro-4-acetoxy nonane (Step B(3)), ethyl 8-acetyl-8-tert.-butoxycarbonyl-12-acetoxy-17,17,17-trifluoroheptadecanoate (Step B(4)), ethyl 8-acetyl-12-acetoxy-17,17,17-trifluoroheptadecanoate, (Step C); and 8-acetyl-12-hydroxy-17,17,17-trifluoroheptadecanoic acid (Step D).

EXAMPLE 21

Preparation of 8-Acetyl-12-hydroxy-16-heptadecenoic Acid

The synthesis of this compound is carried out as described in Example 1, except that in Step B(1), and equivalent amount of 5-bromo-1-pentene is used in place of the amyl bromide. Thus, there is obtained in order: ethyl 8-tert.-butoxycarbonyl-9-oxodecanoate (Step A), 1-chloro-8-nonen-4-one (Step B(1)), 1-chloro-8-nonen-4-ol (Step B(2)), 1-chloro-4-acetoxy-8-nonene Step B(3)), ethyl 8-acetyl-8-tert.-butoxycarbonyl-12-acetoxy-16-heptadecenoate (Step B(4)), ethyl 8-acetyl-12-acetoxy-16-heptadecenoate (Step C), and 8-acetyl-12-hydroxy-16-heptadecenoic acid.

EXAMPLE 22

8-Acetyl-12-acetoxyheptadecanoic Acid

A mixture of 8-acetyl-12-hydroxyheptadecanoic acid (8.2 g., 0.025 mole) and acetic anhydride (6.1 g., 0.06 mole) is heated at 60° for 18 hours. The mixture is then cooled and dissolved in 80 ml. ethyl ether. The solution is extracted with an ice-cold solution of 8 g. sodium hydroxide in 150 ml. water. The basic solution is separated and acidified with concentrated hydrochloric acid. The oily acid which separates is taken up in ether, washed with water and dried over sodium sulfate. The ether is evaporated to leave 9.0 g. of the oily crude product.

The product is purified by chromatography on a column containing 150 g. of silica gel and with 1% methanol in chloroform as the eluting solvent. There is obtained 4.3 g. of 8-acetyl-12-acetoxyheptadecanoic acid, a colorless viscous oil; pmr ($CDCl_3$) $\delta 0.88$ (3H,t), 2.04 (3H,s, $CH_3COO$), 2.10 (3H,s,$CH_3CO$), 4.90 (1H,m, HCO), 10.7 (1H,s,COOH).

By substituting the acetic anhydride used in Example 22 with an equivalent amount of propionic anhydride, butyric, anhydride, isobutyric anhydride, valeric anhydride, or pivalic anhydride and conducting the reaction as described in Example 22, there is obtained 8-acetyl-12-propionyloxyheptadecanoic acid, 8-acetyl-12-butyryloxyheptadecanoic acid, 8-acetyl-12-isobutyryloxyheptadecanoic acid, 8-acetyl-12-valeryloxyheptadecanoic acid, and 8-acetyl-12-pivaloyloxyheptadecanoic acid, respectively.

EXAMPLE 23

8-Acetyl-12-formyloxyheptadecanoic Acid

A mixture of 8-acetyl-12-hydroxyheptadecanoic acid (8.2 g., 0.025 mole) and 97% formic acid (10 ml.) is heated at 60° for 24 hours. The mixture is cooled, dissolved in 100 ml. ether, washed with 3 portions of water and dried over sodium sulfate. Evaporation of the ether leaves the product 8-acetyl-12-formyloxyheptadecanoic acid as a slightly yellowish viscous oil.

EXAMPLE 24

Preparation of (5-Acetyl-9-hydroxytetradecyloxy)acetic Acid

Step A: Ethyl 4-Bromobutoxyacetate

Sodium hydride (9.0 g., 0.375 mole) is suspended in 1,2-dimethoxyethane. The mixture is stirred and cooled in an ice bath while ethyl glycollate (39.0 g., 0.375 mole) is added dropwise during one hour. 1,4-Dibromobutane (108 g., 0.5 mole) is added all at once to the resulting thick suspension. The mixture is warmed gently to initiate a strongly exothermic reaction; then the mixture is heated 3 hours on the steam bath. The mixture is poured into cold water. The heavy oil layer is taken up in ether, washed with three portions of water, and dried over sodium sulfate.

Evaporation of the ether and distillation of the residual oil yields 21.3 g. (24%) of ethyl 4-bromobutoxyacetate, a colorless oil, b.p. 99°–103°/0.2 mm.

Step B: Preparation of Ethyl (5-Tert.-butoxycarbonyl-6-oxoheptyloxy)acetate

This compound is prepared essentially by the same procedure as described in Example 1, Step A (except a trace of potassium iodide is added just prior to heating and then the heating period at 100° is continued for 4 hours), using the following reagents:

| | |
|---|---|
| Sodium hydride (57% in mineral oil) | 3.75 g. net wt. (0.0887 mole) |
| Benzene | 40 ml. |
| Dimethylformamide | 40 ml. |
| Tert.-butyl acetoacetate | 12.75 g. (0.0806 mole) |
| Ethyl (4-bromobutoxy) acetate | 21.20 g. (0.0887 mole) |
| Potassium iodide | Trace |

The title compound is obtained as a light yellow oil, yield 15.35 g. (60%), b.p. 166°-168°/0.3 mm; pmr (CDCl$_3$) δ1.48 (9H,s), 2.23 (3H,s CH$_3$CO), 4.07 (2H,s OCH$_2$CO), 4.25 (2H,q).

Step C: Preparation of Ethyl (5-Acetyl-5-tert.-butoxycarbonyl-9-acetoxytetradecyloxy)acetate This compound is prepared essentially by the same procedure as described in Example 1, Step B(4) (except a trace of potassium iodide is added just prior to heating and then the heating period at 100° is continued for 69 hours) using the following reagents:

| Sodium hydride (57% in mineral oil) | 2.23 g. net wt. (0.0530 mole) |
|---|---|
| Dimethylformamide | 25 ml. |
| Benzene | 25 ml. |
| Ethyl (5-tert.-butoxycarbonyl-6-oxoheptyloxy)acetate | 15.24 g. (0.0482 mole) |
| 1-Chloro-4-acetoxy nonane | 11.70 g. (0.0530 mole) |
| Potassium iodide | Trace |

The title compound is obtained as a residual oil, yield 24.13 g.; pmr (CDCl$_3$)δ0.88 (3H,t), 1.45 (9H,s), 2.00 (3H,s CH$_3$COO), 2.12 (3H,s CH$_3$CO), 4.05 (2H,s OCH$_2$CO), 4.23 (2H,q).

Step D: Preparation of Ethyl (5-Acetyl-9-acetoxytetradecyloxy)acetate

This compound is prepared essentially by the same procedure as described in Example 1, Step C (except reflux time is 46 hours), using the following reagents:

| Ethyl (5-acetyl-5-tert.-butoxycarbonyl-9-acetoxytetradecyloxy)acetate | 24.13 g. (0.0482 mole) |
|---|---|
| p-Toluenesulfonic acid monohydrate | .85 g. |
| Toluene | 85 ml. |

The title compound is obtained as a residual oil, yield 17.15 g. The oil is purified by column chromatography on silica gel with chloroform as an eluant; pmr (CDCl$_3$) δ0.88 (3H,t), 2.02 (3H,s CH$_3$COO), 2.11 (3H,s CH$_3$CO), 4.05 (2H,s OCH$_2$CO), 4.23 (2H,q).

Step E: Preparation of (5-Acetyl-9-hydroxytetradecyloxy)acetic Acid

This compound is prepared essentially by the same procedure as described in Example 1, Step D (except reaction solution is allowed to stand at 60°-65° for 17½ hours), using the following reagents:

| Ethyl (5-Acetyl-9-acetoxytetradecyloxy)acetate | 13.30 g. (0.0332 mole) |
|---|---|
| Sodium hydroxide | 3.98 g. (0.0996 mole) |
| Water | 19 ml. |
| Methanol | 171 ml. |

The title compound is obtained as a residual oil, yield, 6.66 g. The oil is purified by column chromatography on silica gel with 2% methanol in chloroform as an eluant, pmr (CDCl$_3$) δ0.90 (3H,t), 2.13 (3H,s CH$_3$CO), 4.08 (2H,s OCH$_2$CO), 7.27 (2H,s OH, COOH).

Anal. Calcd. for C$_{18}$H$_{34}$O$_5$: C, 65.42; H, 10.37; Found: C, 65.52; H, 10.55

EXAMPLE 25

Methyl 8-Acetyl-12-hydroxyheptadecanoate

A solution of diazomethane (approx. 2.5 g., 0.06 mole) in order (100 ml.) is mixed with a solution of 8-acetyl-12-hydroxyheptadecanoic acid (9.9 g., 0.03 mole) in ether (50 ml.). The resulting solution is allowed to stand 4 hours at room temperature. Acetic acid is then added to destroy the excess diazomethane and the solution is washed with dilute sodium bicarbonate solution and water and dried over sodium sulfate. Evaporation of volatile materials at reduced pressure yields methyl 8-acetyl-12-hydroxyheptadecanoate, a colorless viscous oil.

EXAMPLE 26

Decyl 8-Acetyl-12-hydroxyheptadecanoate

Using the method of Example 25 but substituting an ether solution 1-diazodecane for the ether solution of diazomethane there is obtained decyl 8-acetyl-12-hydroxyheptadecanoate, a colorless viscous oil.

EXAMPLE 27

Preparation of N-[(2-Dimethylaminoethyl)]8-acetyl-12-hydroxyheptadecanamide.0.1 chloroformate A solution of 8-acetyl-12-hydroxyheptadecanoic acid (3.29 g., 10 millimole), Example 1, Step D, triethylamine (1.74 ml., 12.5 millimole) and distilled water (18 ml., 1.0 mole) in acetonitrile (100 ml.) is treated with N-t-butyl-5-methylisoxazolium perchlorate (3.0 g., 12.5 millimole). The resulting solution is evaporated in vacuo (water aspirator) at 20°-23° for 4 hours providing a tacky residue which is triturated with water (150 ml.) at 0°-5° for 15 minutes. After decanting the aqueous phase, the oily residue is dissolved in benzene-ether [(1:1), 200 ml.]. The organic extract is dried oveer sodium sulfate, filtered and evaporated in vacuo at 35°-40° providing the desired "active ester", N-t-butyl-3-(8-acetyl-12-hydroxyheptadecanoyloxy)crotonamide, as a pale yellow oil.

A solution of 2-dimethylaminoethylamine (0.88 g., 10 millimole) in acetonitrile (25 ml.) is added to a solution of the "active ester" in acetonitrile (25 ml.) providing a clear solution which is stirred at 25° for 17 hours. The solvent is removed in vacuo at 40°-50° leaving a residual oil which is partitioned between ether (200 ml.) and water (2 × 100 ml.). The organic extract is washed with saturated brine (2 × 100 ml.), dried over sodium sulfate, filtered and evaporated in vacuo at 40°-50° providing a tan, crude oil.

The oil is partitioned between 5% hydrochloric acid (100 ml.) and ether (2 × 100 ml.). The aqueous acid phase is slowly basicified with sodium bicarbonate (16.8 g., 0.2 mole), then with 40% aqueous sodium hydroxide (10 ml.) providing a heterogeneous mixture which is extracted with ether (200, 100 ml.). The organic extract is washed with saturated brine (200 ml.), dried over sodium sulfate, filtered and evaporated in vacuo at 40°-50° leaving the title compound as a pale yellow oil (2.8 g., 76%); pmr (CDCl$_3$) δ0.88 (3H,t), 2.10 (3H,s), 2.22 (6H,s), 3.38 (5H,m), 4.09 (H,s) and 7.11 (H, bt).

Anal. Calcd. for C$_{23}$H$_{46}$N$_2$O$_3$.0.1 CHCl$_3$: C, 67.57; H, 11.32; N, 6.84; Found: C, 67.63; H, 11.38; N, 6.66.

EXAMPLE 28

Preparation of 8-Acetyl-12-hydroxyheptadecanoic Acid Hydrazide

This compound is prepared essentially by the same procedure as described in Example 19 except hydrazine is used rather than an aliphatic amine and the acid-hydrazine conjugation is effected at −15° employing the following reagents:

| | |
|---|---|
| 8-Acetyl-12-hydroxy-heptadecanoic Acid (Example 1, Step D) | 3.29 g., 0.01 mole |
| Triethylamine | 1.74 ml., 0.0125 mole |
| Distilled water | 18 ml., 1.0 mole |
| N-t-Butyl-5-methyl-isoxazolium perchlorate | 3.0 g., 0.0125 mole |
| Acetonitrile | 150 ml. |
| Hydrazine.hydrate | 0.5 g., 0.01 mole |

The title compound is obtained as a pale yellow oil.

EXAMPLE 29

Preparation of 8-Glycoloyl-12-hydroxyheptadecanoic Acid

Step A: Preparation of Ethyl 8-Diazoacetyl-12-acetoxyheptadecanoate

Diazomethane (6 g., 0.143 mole) is generated via dropwise addition of a solution of Diazald ® (43 g.) in ether (400 ml.) over 45 minutes to a warm (65%), stirred solution of potassium hydroxide (12 g., 0.214 mole) in carbitol-water (7:2, 90 ml.). The resulting yellow, ethereal diazomethane distillate is cooled to 0° and treated with a solution of ethyl 8-chlorocarbonyl-12-acetoxyheptadecanoate (8.1 g., 0.02 mole) (Example 7, Step D), in ether (40 ml.) added over a period of 15 minutes.

The resulting solution is maintained at 0° for one hour, then allowed to slowly evaporate at 20° over 22 hours to a total volume of 50 ml. Additional ether (200 ml.) is added to the reaction solution and again the solvent is allowed to evaporate at 20° over 15 hours. The title compound is obtained as a deep yellow oil (8.4 g., 100%), $\nu_{max}^{neat}$ 2100, 1730 and 1645 cm$^{-2}$.

Step B: Preparation of Ethyl 8-Glycoloyl-12-acetoxyheptadecanoate

A clear, yellow solution of ethyl 8-diazoacetyl-12-acetoxyheptadecanoate (8.4 g., 0.02 mole) in dioxane (50 ml.) is vigorously stirred at 20° and treated with 2N sulfuric acid (30 ml.) added dropwise over 5 minutes. The resulting turbid solution is warmed to and maintained at 65° for 30 minutes. The reaction solution is cooled to 20°, diluted with water to a total volume of one liter and extracted with ether (5 × 200 ml.). The organic extract is washed with water (2 × 200 ml.), 5% aqueous sodium bicarbonate (200 ml.), water (200 ml.), and saturated brine (2 × 200 ml.), dried over sodium sulfate and filtered. Evaporation (in vacuo at 40°–65°) of the filtrate gives the title compound as a deep yellow oil (7.9 g., 96%), pmr (CDCl₃) δ0.86 (3H,t), 1.28 (27H,e), 2.0 (3H,s), 2.25 (3H,t), 3.36 (H,b), 4.10 (2H,q), 4.21 (2H,s) and 4.84 (H,b).

Step C: Preparation of 8-Glycoloyl-12-hydroxyheptadecanoic Acid

A clear, yellow solution of ethyl 8-glycoloyl-12-hydroxyheptadecanoate (7.9 g., 0.02 mole) and potassium hydroxide (2.24 g., 0.04 mole) in 90% aqueous methanol (50 ml.) is stirred at 25° under nitrogen for 20 hours. The reaction solution is evaporated in vacuo at 40° leaving a residual red oil which is dissolved in water (200 ml.). The resulting solution is acidified with concentrated hydrochloric acid (10 ml.) and extracted with ether (2 × 200 ml.). The organic extract is washed with saturated brine (2 × 200 ml.), dried over sodium sulfate, filtered and evaporated in vacuo at 40°–50° providing the title compound as a slightly impure, deep yellow oil (6.3 g., 92%).

EXAMPLE 30

Preparation of 8-(1,2-Dihydroxyethyl)-12-hydroxyheptadecanoic Acid

This compound is prepared essentially by the same procedure as described in Example 9 employing the following reagents:

| | |
|---|---|
| 8-Glycoloyl-12-hydroxy-heptadecanoic Acid (Example 29, Step C) | 3.83 g., 0.011 mole |
| Sodium borohydride | 0.38 g., 0.01 mole |
| Sodium hydroxide | 0.6 g., 0.015 mole |
| Water | 40 ml. |

The title compound is obtained as a pale yellow oil.

EXAMPLE 31

Preparation of 8-Formyl-12-hydroxyheptadecanoic Acid

Step A: Preparation of 8-Formyl-12-benzyloxyheptadecanoic Acid

This compound is prepared essentially by the same procedure as described in Example 8, Step D(4), employing the following reagents:

| | |
|---|---|
| 8-Oxo-12-benzyloxy-heptadecanoic acid (Example 8, Step C) | 7.81 g., 0.02 mole |
| Methoxymethyltriphenyl-phosphonium bromide | 7.62 g., 0.02 mole |
| 57% Sodium hydride in mineral oil | 1.68 g., 0.04 mole |
| HMPT | 100 ml. |
| Concentrated hydrochloric acid | 6 ml. |
| Water | 2 l. |

The title compound is obtained as a clear, colorless oil.

Step B: Preparation of 8-Formyl-12-hydroxyheptadecanoic Acid

This compound is prepared essentially by the same procedure as described in Example 8, Step G, employing the following reagents:

| | |
|---|---|
| 8-Formyl-12-benzyloxy-heptadecanoic acid | 4.04 g., 0.01 mole |
| Hydrogen (g) | 243 ml., 0.01 mole |
| 10% Palladium on charcoal | 0.4 g. |
| Ethanol | 100 ml. |

The title compound is obtained as a pale yellow oil.

EXAMPLE 32

Preparation of 8-Acryloyl-12-hydroxyheptadecanoic Acid

A solution of 8-(3-hydroxypropionyl)-12-hydroxyheptadecanoic acid . ½ chloroformate (Example 8, Step G) (3.58 g., 0.01 mole) in chloroform (5 ml.) is applied to a silica gel column (100 g., E. Merck, Darmstadt, 0.05–0.2 mm.). The column is allowed to stand at 25° for 24 hours, then eluted with chloroform-methanol (98:2) to slowly elute the title compound as a pale yellow oil.

EXAMPLE 33

Preparation of 8-Acetyl-12-hydroxy-12-methylheptadecanoic Acid

Step A: Ethyl 8-Acetyl-8-tert.-butoxycarbonyl-12-methyl-11-heptadecenoate

This compound is prepared essentially by the same procedure described in Example 1, Step B(4), except that the following reagents are used:

| | |
|---|---|
| Sodium hydride (57% in mineral oil) | 12.0 g. (0.285 mole) |
| Benzene | 130 ml. |
| Dimethylformamide | 130 ml. |
| Ethyl 8-tert.-butoxy-carbonyl-9-oxodecanoate | 81.4 g (0.259 mole) |
| 1-Chloro-4-mmethyl-3-nonene | 62.4 g. (0.285 mole) |

The title compound is obtained as an orangered residual oil, yield 124.4 g.; pmr (CDCL$_3$) δ1.45 (9H,s), 2.12 (3H,s), 4.12 (2H,9), 5.15 (1H,m HC=).

Step B: Ethyl 8-Acetyl-12-methyl-11-heptadecenoate

This compound is prepared essentially by the same procedure described in Example 1, Step C (except reflux time is 21 hours), using the following reagents:

| | |
|---|---|
| Ethyl 8-acetyl-8-tert.-butoxycarbonyl-12-methyl-11-heptadecenoate | 117.2 g. (0.259 mole) |
| p-Toluenesulfonic acid monohydrate | 4.5 g. |
| toluene | 450 ml. |

The title compound is obtained as a residual oil, yield 94.8 g. It is purified by column chromatography on silica gel with chloroform as eluant. The purified product exhibits a single spot, Rf 0.73, on silica gel thin-layer chromatography plates developed with 1% methanol in chloroform; pmr (CDCl$_3$) 2.12 (3H,s), 4.12 (2H,q), 5.12 (1H,m, HC=).

Step C: Ethyl 8-Acetyl-12-hydroxy-12-methylheptadecanoate

Mercuric acetate (3.8 g., 0.012 mole) is dissolved in water (12 ml.) and tetrahydrofuran (20 ml.) is added to give a suspension of a yellow solid. Then, ethyl 8-acetyl-12-methyl-11-heptadecenoate (4.2 g., 0.012 mole) in tetrahydrofuran (20 ml.) is added, and the mixture stirred at room temperature for 24 hours. After 6 hours, the yellow suspended solid has disappeared and a cloudy solution results. To the solution is added 3M sodium hydroxide solution (12 ml.), followed by 0.5M sodium borohydride solution in 3M sodium hydroxide (12 ml.). Liquids are decanted from the precipitated mercury. The organic layer is taken up in ether, washed with three portions of water and dried over sodium sulfate. Evaporation of the ether leaves 4.4 g. of ethyl 8-acetyl-12-hydroxy-12-methylheptadecanoate as a yellowish oil used in the next step without further purification; pmr (CDCl$_3$) δ0.88 (3H,t), 1.13 (3H,s, CH$_3$COH), 1.25 (3H,t, CH$_3$CH$_2$OCO-), 2.12 (3H,s, CH$_3$CO), 4.12 (2H,q).

Step D: 8-Acetyl-12-hydroxy-12-methylheptadecanoic Acid

This compound is prepared essentially by the same procedure described in Example 1, Step D, using the following reagents:

| | |
|---|---|
| Ethyl 8-acetyl-12-hydroxy-12-methyl-heptadecanoate | 4.2 g. (0.011 mole) |
| Sodium hydroxide | 1.0 g. (0.025 mole) |
| Water | 10 ml. |
| Methanol | 50 ml. |

The title compound is obtained as a colorless viscous oil, yield 3.5 g. It is purified by column chromatography on silica gel with chloroform elution; pmr (CDCl$_3$) δ0.88 (3H,t), δ 1.13 (3H,s CH$_3$COH), 2.12 (3H,s,CH$_3$CO), 7.25 (2H,s OH and COOH).

EXAMPLE 34

Preparation of 8-Acetyl-12-hydroxy-13,13-dimethylheptadecanoic Acid

Step A(1): Preparation of 1-Chloro-5,5-dimethyl-4-nonanone

Four hundred ml. of a solution in ether of 1,1-dimethylpentylmagnesium chloride prepared from magnesium (24.3 g., 1.0 mole) and 1-chloro-1,1-dimethylpentane (134.5 g., 1.0 mole) according to the procedure of Whitmore and Badertscher [J. Am. Chem. Soc., 55, 1559 (1933)] is added dropwise with stirring to 4-chlorobutyryl chloride (197 g., 1.4 moles) in ether (400 ml.) during 6 hours. The reaction mixture is stirred for an additional 12 hours. It is then poured into a mixture of ice and dilute hydrochloric acid. The ether layer is separated, washed with water, and dried over sodium sulfate. The ether is evaporated and the residue distilled at aspirator vacuum through a Vigreaux column to yield the product as a colorless oil.

Step A(2): Preparation of 1-chloro-5,5-dimethyl-4-nonanol

By following the procedure described for 1-chloro-4-nonanol (Example 1, Step B(2)) but substituting 1-chloro-5,5-dimethyl-4-nonanone for 1-chloro-4-nonanone and continuing stirring and heating at 50° for 6 hours, there is obtained 1-chloro-5,5-dimethyl-4-nonanol.

Step A(3): Preparation of 1-Chloro-4-acetoxy-5,5-dimethylnonane

By following the procedure described for 1-chloro-4-acetoxynonane (Example 1, Step B(3)) but substituting 1-chloro-5,5-dimethyl-4-nonanol for 1-chloro-4-nonanol and continuing the steam bath heating for 4 hours, there is obtained 1-chloro-4-acetoxy-5,5-dimethylnonane.

Step A(4): Preparation of Ethyl 8-Acetyl-8-tert-butoxycarbonyl-12-acetoxy-13,13-dimethylheptadecanoate This compound is prepared as described in Example 1, Step B(4) except that 1-chloro-4-acetoxy-5,5-dimethylnonane is substituted for 1-chloro-4-acetoxynonane. The product is obtained as a residual oil which is used in the next step without purification.

Step B: Preparation of Ethyl 8-Acetyl-12-acetoxy-13,13-dimethylheptadecanoate This compound is prepared as described in Example 1, Step C except that ethyl 8-acetyl-8-tert-butoxycarbonyl-12-acetoxy-13,13-dimethylheptadecanoate is substituted for ethyl 8-acetyl-8-tert-butoxycarbonyl-12-acetoxyheptadecanoate. The product, a viscous yellowish oil, is purified by chromatography on silica gel with chloroform as eluant.

Step C: Preparation of 8-Acetyl-12-hydroxy-13,13-dimethylheptadecanoic Acid

This compound is prepared as described in Example 1, Step D, except that ethyl 8-acetyl-12-acetoxy-13,13-dimethylheptadecanoate is substituted for ethyl 8-acetyl-12-acetoxyheptadecanoate. The product is purified by chromatography of silica gel with 2% methanol in chloroform as eluant and is obtained as a colorless viscous oil.

EXAMPLE 35

Preparation of 8-Acetyl-12-hydroxy-10-heptadecynoic Acid

Step A(1): Preparation of 3-Acetoxy-1-octyne

1-Octyn-3-ol (100 g., 0.794 mole) is dissolved in pyridine (79 g., 1.0 mole) and acetic anhydride (81.6 g., 0.80 mole) is added dropwise with stirring during one hour. The temperature rises to 45°. The solution is heated at 55° for 1 hour and is then cooled and poured into 200 ml. ice-cold 5% hydrochloric acid. The oily product is taken up in ether, washed with water and brine and dried over sodium sulfate. The ether is evaporated and the residual oil distilled to yield 106.4 g. (80%) of 3-acetoxy-1-octyne, b.p. 91°–92°/15 mm.

Step A(2): Preparation of 1-Diethylamino-4-acetoxy-2-nonyne

A mixture of 3-acetoxy-1-octyne (58.5 g., 0.35 mole), diethylamine (28.5 g., 0.39 mole), paraformaldehyde (13.8 g., 0.46 mole) and p-dioxane (60 ml.) is heated on the steam bath under a reflux condenser for 17 hours. The resulting solution is cooled and diluted with 250 ml. of ether. The solution is extracted with 300 ml. of 5% hydrochloric acid. The acidic aqueous extract is made basic with 10% sodium hydroxide solution. The liberated amine is taken up in ether, washed with water and brine and dried over sodium sulfate. The ether is evaporated and the residual oil distilled to yield 73.1 g. (89%) of 1-diethylamino-4-acetoxy-2-nonyne, b.p. 103°–109°/0.3 mm.

Anal. Calcd. for $C_{15}H_{17}NO_2$: C, 71.10; H, 10.74; N, 5.33; Found; C, 70.73; H, 11.03; N, 5.55.

Step A(3): Preparation of 1-Bromo-4-acetoxy-2-nonyne

A solution of 1-diethylamino-4-acetoxy-2-nonyne (50.6 g., 0.20 mole) and cyanogen bromide (21.2 g., 0.20 mole) in ether (250 ml.) is allowed to stand at 25°–27° for 18 hours. The ether solution is washed with 5% hydrochloric acid solution, water, and brine and dried over sodium sulfate. The ether is evaporated and the residual oil distilled. After a forerun of diethylcyanamide, there is collected 34.1 g. (65%) of 1-bromo-4-acetoxy-2-nonyne, b.p. 97°–105°/0.2 mm.

Anal. Calcd. for $C_{11}H_{17}BrO_2$: C, 50.59; H, 6.56; Found: C, 50.54; H, 6.49.

Step A(4): Preparation of Diethyl 2-Acetyl-2-(4-acetoxy-2-nonyn-1-yl)azelate This compound is prepared essentially by the same procedure described in Example 1, Step B(4) (except heating period at 100° is one hour) using the following reagents:

| | |
|---|---|
| sodium hydride (57% in mineral oil) | 3.4 g. (0.14 mole) |
| benzene | 65 ml. |
| dimethylformamide | 65 ml. |
| diethyl 2-acetylazelate (Ex. 6, Step A) | 36.7 g. (0.128 mole) |
| 1-bromo-4-acetoxy-2-nonyne | 36.7 g. (0.14 mole) |

The product is obtained as a residual oil, yield 59.5 g., which is used in the next step without purification.

Step B: Preparation of 8-Acetyl-12-hydroxy-10-heptadecynoic Acid

A solution of diethyl 2-acetyl-2-(4-acetoxy-2-nonyn-1-yl)azelate (59.7 g., 0.128 mole) and sodium hydroxide (30 g., 0.75 mole) in water (200 ml.) and methanol (800 ml.) is heated at 60° for 16 hours. Most of the methanol is then distilled at reduced pressure and the residue is dissolved in water. The solution is acidified to Congo Red with hydrochloric acid and the oily product taken up in ether and dried over sodium sulfate. Evaporation of the ether leaves 41.1 g. of the crude product as a reddish viscous oil. The product is purified by chromatography on 650 g. of silica gel with 2% methanol in chloroform as eluant. Fifteen grams of pure 8-acetyl-12-hydroxy-10-heptadecynoic acid is obtained as a yellow viscous oil; pmr (CDCl$_3$) δ0.90 (3H,t), 2.20 (3H,s CH$_3$CO), 4.37 (1H,t HCO).

Anal. Calcd. for $C_{19}H_{32}O_4$: C, 70.33; H, 9.94; Found: C, 70.38; H, 9.94.

EXAMPLE 36

Preparation of 8-Acetyl-12-(S)-hydroxyheptadecanoic Acid

Step A(1): Preparation of 3(S)-Acetoxy-1-octyne

This compound is prepared as described in Example 35, Step A(1) except that (S)-1-octyn-3-ol, $[\alpha]_D^{26} - 6.4°$ (C 3.3, CHCl$_3$) is substituted for racemic 1-octyn-3-ol. 3(S)-Acetoxy-1-octyne has $[\alpha]_D^{26} - 79°$ (C 3.0, CHCl$_3$).

Step A(2): Preparation of 1-Diethylamino-4(S)-acetoxy-2-nonyne

This compound is prepared as described in Example 35, Step A(2), except that 3(S)-acetoxy-1-octyne is substituted for racemic 3-acetoxy-1-octyne. 1-Diethylamino-4(S)-acetoxy-2-nonyne has $[\alpha]_D^{26} - 80°$ (C 3.3, CHCl$_3$).

Step A(3): Preparation of 1-Bromo-4(S)-acetoxy-2-nonyne

This compound is prepared as described in Example 35, Step A(3), except that 1-diethylamino-4(S)-acetoxy- 2-nonyne is substituted for racemic 1-diethylamino-4-acetoxy-2-nonyne. 1-Bromo-4(S)-acetoxy-2-nonyne has $[\alpha]_D^{26} -83°$ (C 3.7, CHCl$_3$).

Step A(4): Preparation of Diethyl 2-Acetyl-2-[4(S)-acetoxy-2-nonyn-1yl]azelate

This compound is prepared as described in Example 35, Step A(4), except that 1-bromo-4(S)-acetoxy-2-nonyne is substituted for racemic 1-bromo-4-acetoxy-2-nonyne. The product is obtained as a residual oil with $[\alpha]_D^{26} -48.9°$ (C, 3.9, CHCl$_3$).

Step B: Preparation of 8-Acetyl-12-(S)-hydroxy-10-heptadecynoic Acid

This compound is prepared as described in Example 35, Step B, except that diethyl 2-acetyl-2-[4(S)-acetoxy-2-nonyn-1-yl]azelate is substituted for diethyl 2-acetyl-2-(4-acetoxy-2-nonyl-1-yl)azelate. The product is purified by chromatography on silica gel with 2% methanol in chloroform as eluant. It is obtained as a colorless viscous oil with $[\alpha]_D^{26} -1.94°$ (C, 3.5, CHCl$_3$).

Anal. Calcd. for $C_{19}H_{32}O_4$: C, 70.33; H, 9.94; Found: C, 70.44; H, 10.07.

Step C: Preparation of 8-Acetyl-12-(S)-hydroxyheptadecanoic Acid

8-Acetyl-12-(S)-hydroxy-10-heptadecynoic acid (18.0 g., 0.056 mole) and 5% platinum on charcoal catalyst (2.5 g.) are placed in a mixture of ethyl acetate (50 ml.) and cyclohexane (100 ml.) and hydrogenated in a Parr apparatus with an initial hydrogen pressure of 45 pounds per square inch. The uptake of the required 2 molar equivalents of hydrogen is complete in 10 minutes. The catalyst is removed by filtration and the solvents evaporated to leave the product as a light yellow oil weighing 15 g. It is purified by chromatography on 200 g. of silica gel. There is obtained 10.8 g. of 8-acetyl-12-(S)-hydroxyheptadecanoic acid as a nearly colorless viscous oil, $[\alpha]_D^{26}+ 1.0°$ (C 3.9, CHCl$_3$).

Anal. Calcd. for $C_{19}H_{36}O_4$: C, 69.47; H, 11.05; Found: C, 69.65; H, 11.44.

EXAMPLE 37

Preparation of 8-Acetyl-12-(R)-hydroxyheptadecanoic Acid

By following exactly the same procedures as described in Example 35 but beginning with (R)-1-octyn-3-ol instead of racemic 1-octyn-3-ol, there are obtained successively: Step A(1), 3-(R)-acetoxy-1-octyne, $[\alpha]_D^{26}+ 70°$ (C 3.1, CHCl$_3$); Step A(2), 1-diethylamino-4-(R)-acetoxy-2-nonyne, $[\alpha]_D^{26}+ 74°$ (C 3.2, CHCl$_3$); Step A(3), 1-bromo-4-(R)-acetoxy-2-nonyne, $[\alpha]_D^{26}+ 75°$ (C 3.2, CHCl$_3$); Step A(4), diethyl 2-acetyl-2-[4-(R)-acetoxy-2-nonyl-1-yl]azelate, $[\alpha]_D^{26}+ 46°$ (C 3.7, CHCl$_3$); Step B, 8-acetyl-12-(R)-hydroxy-10-heptadecynoic acid, $[\alpha]_D^{26}+ 2.18°$ (C 3.8, CHCl$_3$);

Anal. Calcd. for $C_{19}H_{32}O_4$: C, 70.33; H, 9.94; found: C, 70.58; H, 9.92; Step C, 8-acetyl-12-(R)-hydroxyheptadecanoic acid, $[\alpha]_D^{26}- 0.79°$ (C 3.8, CHCl$_3$);

Anal. Calcd. for $C_{19}H_{36}O_4$: C, 69.47; H, 11.05; found: C, 69.19; H, 11.34.

EXAMPLE 38

Preparation of 8-(1-Hydroxy-1-methylethyl)-12-hydroxy-12-methylheptadecanoic Acid Step A: Preparation of 8-Acetyl-12-oxoheptadecanoic Acid A solution of 8-acetyl-12-hydroxyheptadecanoic acid (9.85 g., 0.03 mole) in acetone (29 ml.) is cooled to 5°–10° and treated, dropwise, over 2¼ hours with a solution prepared from a mixture of chromium trioxide (2.57 g., 0.0257 mole) water (7.5 ml.) and concentrated sulfuric acid (2.1 ml.). Stirring is continued for an additional 30 minutes.

The reaction mixture is filtered and the filtrate is diluted with water (240 ml.). The resulting oil is extracted with ether and the combined extracts are washed with saturated sodium chloride solution and then dried over anhydrous sodium sulfate. The solvent is removed under vacuum to give the title compound as a light yellow residual oil, yield 9.10 g. (93%); pmr (CDCl$_3$) δ 0.88 (3H,t), 2.12 (3H,s), 2.38 (7H,m), 11.18 (1H,s COOH).

Anal. Calcd. for $C_{19}H_{34}O_4$: C, 69.90; H, 10.50; Found: C, 69.50; H, 10.59.

Step B: Preparation of 8-(1-Hydroxy-1-methylethyl)-12-hydroxy-12-methylheptadecanoic Acid Magnesium (3.4 g., 0.14 mole) is placed in tetrahydrofuran (60 ml.) and methyl bromide gas is bubbled into the mixture until all the magnesium is consumed and a clear solution of methylmagnesium bromide results. This solution is stirred and kept cool by means of a 25° water bath while 8-acetyl-12-oxoheptadecanoic acid (9.3 g., 0.028 mole) in tetrahydrofuran (30 ml.) is added dropwise over a period of 40 min. During this time, a white solid separates and the mixture becomes difficult to stir. The mixture is heated at reflux for 45 minutes, then cooled, and poured into 200 ml. saturated ammonium chloride solution. The oily product which forms is taken up in ether, washed with water, and dried over sodium sulfate. On evaporation of the ether, there is obtained 10.0 g. of yellow oil. The product is isolated by chromatography on 200 g. of silica gel with 4% methanol in chloroform as the eluant. The product isolated shows a single spot of the silica gel thin layer chromatographic plate with chloroform-methanol-acetic acid, 97:2:1, Rf 0.15. The amount of 8-(1-hydroxy-1-methylethyl)-12-hydroxy-12-methylheptadecanoic acid obtained is 4.0 g.; it is a very viscous yellowish oil; pmr (CDCl$_3$) δ0.90 (3H,t), 1.17 (9H, s CH$_3$COH), 2.37 (2H, t CH$_2$COO), 4.76 (3H,s OH and COOH).

Anal. Calcd. for $C_{21}H_{42}O_4$: C, 70.34; H, 11.81; Found: C, 70.61; H, 12.01.

EXAMPLE 39

Preparation of 8-Acetyl-11-(1-hydroxycyclohexyl)-10-undecynoic Acid

Step A(1): Preparation of 1-Acetoxy-1-ethynylcyclohexane

1-Ethynylcyclohexan-1-ol (100 g., 0.8 mole) is added dropwise with stirring to a mixture of acetic anhydride (86.7 g., 0.85 mole) and sulfuric acid (0.25 ml.). The temperature of the reaction mixture is kept at 10°–12° during the addition by means of an ice bath. The mixture is then stirred without cooling for 1.5 hours. It is then poured into 300 ml. of ice water. The oily product is taken up in ether, washed with water, dilute sodium bicarbonate solution and brine and dried over sodium sulfate. Distillation affords 107 g. (80%) of 1-acetoxy-1-ethynylcyclohexane, b.p. 95°–97°/15 mm.

Step A(2): Preparation of
1-Acetoxy-1-(3-diethylamino-1-propynyl)cyclohexane

A mixture of 1-acetoxy-1-ethynylcyclohexane (64.00 g., 0.385 mole), diethylamine (30.95 g., 0.424 mole), paraformaldehyde, (15.00 g.; 0.500 mole), cuprous chloride (1.5 g.) and dioxane (60 ml.) is stirred well. An exothermic reaction gradually results which may require external cooling to prevent spillage. After this initial reaction, the mixture is heated on a steam bath for 1½ hours.

The cooled mixture is treated with ether and the product is extracted into ice-cold 5% hydrochloric acid. This cold aqueous acidic solution is then basified with ice-cold 10% sodium hydroxide. The oily amine is extracted with ether and the combined extracts are washed with saturated sodium chloride solution and then dried over anhydrous sodium sulfate. The solvent is removed under vacuum and the residual oil is distilled to give 72.7 g. (75%) of light yellow oil, b.p. 113°–115°/0.15 mm.; pmr (CDCl$_3$) δ1.07 (6H,t), 2.02 (3H,s CH$_3$COO), 2.60 (4H,q CH$_3$$\underline{CH_2}$N), 3.52 (2H,s CH$_2$C≡).

Step A(3): Preparation of
1-Acetoxy-1-(3-bromo-1-propynyl)cyclohexane

Cyanogen bromide (31.8 g., 0.3 mole) is added to a solution of 1-acetoxy-1-(3-diethylamino-1-propynyl)cyclohexane (61 g., 0.24 mole) and the resulting solution is allowed to stand at 25°–27° for 18 hours. The ether solution is washed with 5% hydrochloric acid solution, water and brine and dried over sodium sulfate. The ether is evaporated and the residual oil distilled. There is obtained 34.8 g. (55%) of 1-acetoxy-1-(3-bromo-1-propynyl)cyclohexane, a slightly yellowish oil, b.p. 114°–120°/0.2 mm.

Step A(4): Preparation of Diethyl
2-Acetyl-2-[3-(1-acetoxycyclohexyl)-2-propyn-1-yl]azelate This compound is prepared essentially by the same procedure described in Example 35, Step A(4) except that 1-acetoxy-(3-bromo-1-propynyl)cyclohexane is substituted for 1-bromo-4-acetoxy-2-nonyne. The product is obtained as an orange residual oil which is used in the next step without purification.

Step B: Preparation of
8-Acetyl-11-(1-hydroxycyclohexyl)-10-undecynoic Acid

This compound is prepared by the same procedure described in Example 35, Step B, except that diethyl 2-acetyl-2-[3-(1-acetoxycyclohexyl)-2-propyn-1-yl]azelate is substituted for diethyl 2-acetyl-2-(4-acetoxy-2-nonyn-1-yl)azelate. The chromatographically purified product is a yellowish viscous oil; pmr (CDCl$_3$) δ2.14 (3H,s CH$_3$CO), 6.50 (2H,s OH and COOH).

Anal. Calcd. for C$_{19}$H$_{30}$O$_4$: C, 70.77; H, 9.38; Found: C, 70.75; H, 9.78.

EXAMPLE 40

Preparation of
8-Acetyl-11-(1-hydroxycyclohexyl)undecanoic Acid

This compound is prepared essentially by the same hydrogenation procedure described in Example 36, Step C, except that 8-acetyl-11-(1-hydroxycyclohexyl)-10-undecynoic acid (Example 39) is substituted for 8-acetyl-12(S)-hydroxy-10-heptadecynoic acid. The product is obtained as a yellowish viscous oil; pmr (CDCl$_3$) δ 2.08 (3H,s CH$_3$CO), δ6.52 (2H, s OH and COOH). Anal. Calcd. for C$_{19}$H$_{34}$O$_4$: C, 69.90; H, 10.50; Found: C, 70.23; H, 10.70.

EXAMPLE 41

Preparation of
8-Acetyl-11-(1-hydroxycyclooctyl)-10-undecynoic Acid

By the use of the procedures described in Example 39 but starting with 1-ethynylcyclooctan-1-ol in Step A(1) instead of 1-ethynylcyclohexan-1-ol, there are obtained successively: Step A(1), 1-acetoxy-1-ethynylcyclooctane; Step A(2), 1-acetoxy-1-(3-diethylamino-1-propynyl)cyclooctane; Step A(3), 1-acetoxy-1-(3-bromo-1-propynyl)cyclooctane; Step A(4), diethyl 2-acetyl-2-[3-(1-acetoxycyclooctyl)-2-propyn-1-yl]azelate; Step B, 8-acetyl-11-(1-hydroxycyclooctyl)-10-undecynoic acid.

EXAMPLE 42

Preparation of
8-Acetyl-11-(1-hydroxycyclooctyl)undecanoic Acid

This compound is prepared essentially by the same hydrogenation procedure described in Example 36, Step C, except that 8-acetyl-11-(1-hydroxycyclooctyl)-10-undecynoic acid (Example 41) is substituted for 8-acetyl-12(S)-hydroxy-10-heptadecynoic acid. The product is obtained as a colorless viscous oil.

EXAMPLE 43

Preparation of
8-(1-hydroxyethyl)-12-hydroxy-(E)-10-heptadecenoic Acid

This compound is prepared by the method described in Example 9 except that 8-acetyl-12-hydroxy-(E)-10-heptadecenoic acid is used instead of 8-acetyl-12-hydroxyheptadecanoic acid. The product is obtained as a yellowish viscous oil.

Anal. Calcd. for C$_{19}$H$_{36}$O$_4$: C, 69.47; H, 11.05; Found: C, 69.54; H, 11.69

EXAMPLE 44

Preparation of
8-(1-Hydroxyethyl)-12-hydroxy-12-methyl-heptadecanoic Acid

This compound is prepared by the method described in Example 9 except that 8-acetyl-12-hydroxy-12-methylheptadecanoic acid is used instead of 8-acetyl-12-hydroxyheptadecanoic acid. The product is obtained as a colorless, very viscous oil; pmr (CDCl$_3$) δ0.90 (3H,t), 2.35 (2H,t, CH$_2$COO), 3.82 (1H,m, HCO), 5.90 (3H,s, OH and COOH).

Anal. Calcd. for C$_{20}$H$_{40}$O$_4$: C, 69.72; H, 11.70; Found: C, 69.42; H, 12.02

EXAMPLE 45

Capsule Formulation

| | |
|---|---|
| 8-Acetyl-11-(1-hydroxycyclohexyl)-undecanoic acid | 50 gm. |
| Stearic Acid (U.S.P. triple pressure) | 125 gm. |
| Pluronic F-68 | 7.5 gm. |
| Corn starch | 125 gm. |

The stearic acid and pluronic are united in a vessel and melted using a water bath at 60°–65° C. The heating is discontinued and the 8-acetyl-12-cyclohexyl-12-hydroxydecanoic acid is dispersed into the mixture and the corn starch is added with stirring which is continued until the mixture cools to ambient temperature. The mixture is reduced to granules by screening and placed in a number 0 hard gelatin containing 307.5 mg. of total solids and 50 mg. of 8-acetyl-11-(1-hydroxycyclohexyl-)undecanoic acid per capsule.

EXAMPLE 46

Parenteral Formulation of a Multidose Solution for Intramuscular and Intravenous Use

| | |
|---|---|
| 8-Acetyl-12-hydroxyheptadecanoic acid | 1 gram |
| Tris(hydroxymethyl)aminomethane (Reagent Grade Tham) | q.s. to adjust solution to pH 7.4 |
| Sodium chloride (U.S.P.) | q.s. to yield isotonic solution |
| Methylparaben | 10 mg. |
| Propylparaben | 1 mg. |
| Distilled water (pyrogen-free) | q.s. to 10 ml. |

The 8-acetyl-12-hydroxyheptadecanoic acid suspended in about 6 ml. of the water is treated with tris(-hydroxymethyl)aminomethane with stirring until the pH reaches 7.4. The methylparaben and propylparaben are added with stirring and sufficient sodium chloride added to produce an isotonic solution. After water is added to bring the final volume to 10 ml., the solution is sterilized by membrane filtration and placed in a vial by an aseptic technique. The solution contains the Tham salt of 8-acetyl-12-hydroxyheptadecanoic acid equivalent to 100 mg./ml. of the free acid.

EXAMPLE 47

Preparation of Suppositories

| | |
|---|---|
| 8-(1-Hydroxyethyl)-12-hydroxyheptadecanoic acid | 200 gm. |
| Butylated hydroxyanisole | 82 mg. |
| Butylated hydroxytoluene | 82 mg. |
| Ethylenediamine tetraacetic acid | 163 mg. |
| Glycerine, U.S.P. 128 gm. | |
| Sodium chloride, microfine | 52.5 gm. |
| Polyethylene glycol 6000 | 128 gm. |
| Polyethylenne glycol 4000 | 1269 gm. |

The polyethylene glycol 4000 and polyethylene glycol 6000 were placed in a surrounded by a water bath at such a temperature required to maintain the melted contents at 60°–65° C. To the melt is added the butylated hydroxyanisole and butylated hydroxytoluene with stirring. Then the ethylenediamine tetraacetic acid and microfine sodium chloride are added to and dispersed in the mixture. The 8-(1-hydroxyethyl)-12-hydroxyheptadecanoic acid is then added and dispersed into the mixture. Finally, the temperature is lowered to 55°–60° C. and the glycerine added and disposed.

While maintaining the temperature of 55°–60° C. and continuous mixing, the melt is dispersed into plastic suppository cavities of a conventional suppository cold-molding device. The suppositories thus prepared contain a total of 1.7778 gm. of contents of which 200 mg. are 8-(1-hydroxyethyl)-12-hydroxyheptadecanoic acid.

What is claimed is:

1. The compound having the following formula:

$$\begin{array}{c} R^1 \\ \diagdown H \\ C-(CH_2)_4-A-R \\ | \\ CH_2-Z-C-C(R^4)_2-(CH_2)_2-R^5 \\ \diagup \diagdown \\ R^2 \quad OR^3 \end{array}$$

wherein

R is carboxy, a carboxy salt, or carboxy having the formula —COOY wherein Y is alkyl having 1–10 carbon atoms, 1-succinimidoethyl, 1-(pivaloyloxy)ethyl, 2-acetamidoethyl, or diloweralkylamino-loweralkyl;

A is ethylene, trimethylene, α-methylethylene, β-methylethylene, α,α-dimethylethylene, or β,β-dimethylethylene;

$R^1$ is formyl, acetyl, propionyl, acryloyl, hydroxyacetyl, 3-hydroxypropionyl, hydroxymethyl, 1-hydroxyethyl, 1,2-dihydroxyethyl, 1,3-dihydroxypropyl, or 1-hydroxy-1-methylethyl;

Z is methylene, ethylene, trimethylene, tetramethylene, vinylene, or ethynylene;

$R^2$ is independently hydrogen or methyl;

$R^3$ is hydrogen;

$R^4$ is selected independently from the group consisting of hydrogen and methyl;

$R^5$ is selected from the group consisting of hydrogen, lower alkyl of 1–4 carbon atoms either straight or branched (e.g., methyl, ethyl, propyl, isopropyl, butyl, tert-butyl), vinyl, and 2,2,2-trifluoroethyl.

2. The compound of claim 1 wherein R is carboxy; a carboxy salt having the formula:

—COO⁻Me⁺ wherein Me is a pharmaceutically acceptable cation derived from a metal or an amine; or carboxy having the formula:

-COOY wherein Y is alkyl having 1–10 carbon atoms, 1-succinimidoethyl, 1-(pivaloyloxy)ethyl, 2-acetamidoethyl, or diloweralkylamino-loweralkyl.

3. The compound of claim 2 wherein R is carboxy or a pharmaceutically acceptable carboxy salt.

4. The compound of claim 3 which has the formula:

$$\begin{array}{c} H \\ R^1-C-(CH_2)_4-A-COOH \\ | \\ CH_2-Z-C-C(R^4)_2-(CH_2)_2-R^5 \\ \diagup \diagdown \\ H \quad OH \end{array}$$

wherein $R^1$ is formyl, acetyl, propionyl, hydroxyacetyl, 1-hydroxyethyl, hydroxymethyl, or 1-hydroxy-1-methylethyl;

A is ethylene, trimethylene, α-methylethylene, β-methylethylene, α,α-dimethylethylene, or β,β-dimethylethylene;

Z is methylene, ethylene, trimethylene, or tetramethylene;

R⁴ is hydrogen or methyl; and

R⁵ is hydrogen, loweralkyl, vinyl, or 2,2,2-trifluoroethyl.

5. The compound of claim 4 wherein A is ethylene and R⁴ is hydrogen.

6. The compound of claim 5 wherein R¹ is acetyl or propionyl.

7. The compound of claim 6 wherein Z and A are ethylene, and R⁵ is ethyl.

8. 8-Acetyl-12-hydroxyheptadecanoic acid, the compound of claim 7 wherein R¹ is acetyl.

9. 8-Acetyl-12-(R)-hydroxyheptadecanoic acid, the compound of claim 7 wherein R¹ is acetyl and the carbon atom bearing the hydroxy group is in the R configuration.

10. 8-Acetyl-12-(S)-hydroxyheptadecanoic acid, the compound of claim 7 wherein R¹ is acetyl and the carbon atom bearing the hydroxy group is in the S configuration.

11. 8-Propionyl-12-hydroxyheptadecanoic acid, the compound of claim 7 wherein R¹ is propionyl.

12. 8-Formyl-12-hydroxyheptadecanoic acid, the compound of claim 7 wherein R¹ is formyl.

13. 8-Acryloyl-12-hydroxyheptadecanoic acid, the compound of claim 6 wherein A and Z are ethylene, R¹ is acryloyl, and R⁵ is ethyl.

14. 8-Acetyl-12-hydroxy-17,17,17-trifluoroheptadecanoic acid, the compound of claim 6 wherein A and Z are ethylene, R¹ is acetyl, and R⁵ is 2,2,2-trifluoroethyl.

15. 8-Acetyl-12-hydroxy-16-heptadecenoic acid, the compound of claim 6 wherein A and Z are ethylene, R¹ is acetyl, and R⁵ is vinyl.

16. The compound of claim 6 wherein R⁵ is straight chain loweralkyl having 2–5 carbon atoms.

17. 8-Acetyl-12-hydroxynonadecanoic acid, the compound of claim 16 wherein A and Z are ethylene, R¹ is acetyl, and R⁵ is butyl.

18. 8-Acetyl-12-hydroxy-16,16-dimethylheptadecanoic acid, the compound of claim 16 wherein A and Z are ethylene, R¹ is acetyl, and R⁵ is tert-butyl.

19. 8-Acetyl-12-hydroxy-13,13-dimethylheptadecanoic acid, the compound of claim 4 wherein R¹ is acetyl, A and Z are ethylene, R⁴ is methyl, and R⁵ is ethyl.

20. The compound of claim 3 which has the formula:

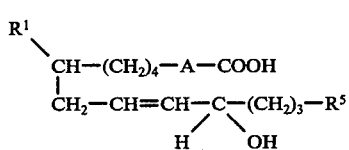

wherein A is ethylene, trimethylene, α-methylethylene, β-methylethylene, α,α-dimethylethylene, β,β-dimethylethylene, or oxymethylene; R¹ is acetyl or 1-hydroxyethyl; and R⁵ is hydrogen, loweralkyl of 1–4 carbon atoms, or 2,2,2-trifluoroethyl.

21. 8-Acetyl-12-hydroxy-(E)-10-heptadecenoic acid, the compound of claim 20 wherein R¹ is acetyl, A is ethylene, and R⁵ is ethyl.

22. 8-(1-Hydroxyethyl)-12-hydroxy-(E)-10-heptadecenoic acid, the compound of claim 20 wherein R¹ is 1-hydroxyethyl, A is ethylene, and R⁵ is ethyl.

23. The compound of claim 3 which has the formula:

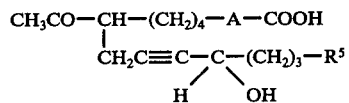

24. 8-Acetyl-12-hydroxy-10-heptadecynoic acid, the compound of claim 23 wherein A is ethylene and R⁵ is ethyl.

25. The compound of claim 3 which has the formula:

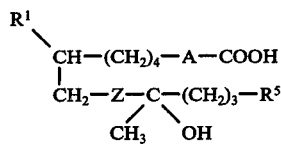

wherein

R¹ is formyl, acetyl, propionyl, hydroxymethyl, 1-hydroxy-1-methylethyl, 1-hydroxyethyl, or hydroxyacetyl;

A is ethylene, trimethylene, α-methylethylene, β-methylethylene, α,α-dimethylethylene, or β,β-dimethylethylene;

Z is methylene, ethylene, trimethylene, tetramethylene, or vinylene; and

R⁵ is hydrogen, loweralkyl of 1–4 carbon atoms, or 2,2,2-trifluoroethyl.

26. 8-Acetyl-12-hydroxy-12-methylheptadecanoic acid, the compound of claim 25 wherein A and Z are ethylene, R¹ is acetyl, and R⁵ is ethyl.

27. 8-(1-Hydroxyethyl)-12-hydroxy-12-methylheptadecanoic acid, the compound of claim 25 wherein A and Z are ethylene, R¹ is 1-hydroxyethyl, and R⁵ is ethyl.

28. 8-(1-Hydroxy-1-methylethyl)-12-hydroxy-12-methylheptadecanoic acid, the compound of claim 25 wherein A and Z are ethylene, R¹ is 1-hydroxy-1-methylethyl, and R⁵ is ethyl.

29. The compound of claim 3 which has the formula:

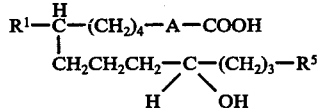

wherein

R¹ is acetyl, propionyl, 3-hydroxypropionyl, acryloyl, formyl;

A is trimethylene, α-methylethylene, β-methylethylene, α,α-dimethylethylene, or β,β-dimethylethylene; and R⁵ is hydrogen, loweralkyl, vinyl, or 2,2,2-trifluoroethyl.

30. 2-Methyl-8-acetyl-12-hydroxyheptadecanoic acid, the compound of claim 29 wherein A is α-methylethylene, R¹ is acetyl, and R⁵ is ethyl.

31. 3,3-Dimethyl-8-acetyl-12-hydroxyheptadecanoic acid, the compound of claim 29 wherein A is β,β-dimethylethylene, R¹ is acetyl, and R⁵ is ethyl.

32. The compound of claim 3 which has the formula:

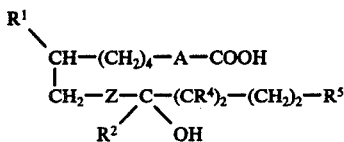

wherein
R[1] is hydroxymethyl, 1-hydroxyethyl, 1-hydroxy-1-methylethyl, 1,2-dihydroxyethyl, or 1,3-dihydroxypropyl;

A is ethylene, trimethylene, α-methylethylene, β-methylethylene, α,α-dimethylethylene, or β,β-dimethylethylene;

z is methylene, ethylene, trimethylene, tetramethylene, vinylene, or ethynylene;

R[2] and R[4] are selected independently from a group consisting of hydrogen and methyl; and R[5] is hydrogen, loweralkyl, vinyl, or 2,2,2-trifluoroethyl.

33. The compound of claim 32 wherein A and Z are ethylene, R[1] is hydroxymethyl or 1-hydroxyethyl, and R[5] is loweralkyl.

34. 8-Hydroxymethyl-12-hydroxyheptadecanoic acid, the compound of claim 33 wherein R[1] is hydroxymethyl, R[2] is hydrogen, and R[5] is ethyl.

35. 8-(1-Hydroxyethyl)-12-hydroxyheptadecanoic acid, the compound of claim 33 wherein R[1] is 1-hydroxyethyl, R[2] is hydrogen, and R[5] is ethyl.

36. The compound of claim 2 which has the formula:

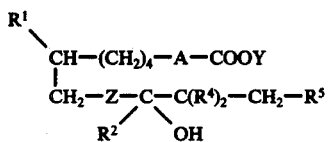

wherein
A is ethylene;
R[1] is acetyl, propionyl, hydroxymethyl, or 1-hydroxyethyl;
R[2] is methyl or hydrogen;
R[4] is selected independently from the group consisting of hydrogen and methyl;
R[5] is selected from the group consisting of hydrogen, lower alkyl of 1-4 carbon atoms either straight or branched (e.g., methyl, ethyl, propyl, isopropyl, butyl, tert-butyl), vinyl, and 2,2,2-trifluroethyl;

and Y is alkyl having 1-10 carbon atoms, 1-succinimidoethyl, 1-(pivaloylethyl), 2-acetamidoethyl, or diloweralkylaminoloweralkyl.

37. Methyl 8-acetyl-12-hydroxyheptadecanoate, the compound of claim 36 wherein R[1] is acetyl, A and Z are ethylene, R[2] and R[4] are hydrogen, R[5] is ethyl, and Y is methyl.

38. A composition comprising the compound of claim 1 in a non-toxic, pharmaceutically-acceptable carrier.

39. The composition of claim 38 which is suitable for oral administration in tablet form.

40. The composition of claim 38 which is suitable for oral administration in capsule form.

41. The composition of claim 38 which is suitable for parenteral administration.

42. The composition of claim 38 which is suitable for use in suppository form.

43. The compound having the following formula:

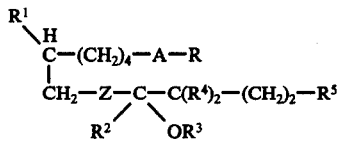

wherein
R is carboxy, a carboxy salt, or derivatized carboxy having the formula -COOY wherein Y is alkyl having 1-10 carbon atoms, 1-succinimidoethyl, 1-(pivaloyloxy)ethyl, 2-acetamidoethyl, or diloweralkylaminoloweralkyl;

A is ethylene, trimethylene, α-methylethylene, β-methylethylene, α,α-dimethylethylene, or β,β-dimethylethylene;

R[1] is formyl, acetyl, propionyl, or acryloyl:

Z is methylene, ethylene, trimethylene, tetramethylene, vinylene, or ethynylene;

R[2] is independently hydrogen or methyl;

R[3] is hydrogen;

R[4] is selected independently from the group consisting of hydrogen and methyl; and R[5] is selected from the group consisting of hydrogen, lower alkyl of 1-4 carbon atoms either straigth or branched (e.g., methyl, ethyl, propyl, isopropyl, butyl, tert-butyl), vinyl, and 2,2,2-trifluoroethyl.

* * * * *